United States Patent [19]

Clark et al.

[11] Patent Number: 4,956,365

[45] Date of Patent: Sep. 11, 1990

[54] DECAHYDRO-8H-ISOQUINO(2,1-G)(1,6)NAPHTHYRIDINE DERIVATIVES AND RELATED COMPOUNDS

[75] Inventors: Robin D. Clark, Palo Alto, Calif.; Andrew T. Kilpatrick, Balerno; Michael Spedding, Edinburgh, both of Scotland

[73] Assignee: Syntex (U.S.A.) Inc., Palo Alto, Calif.

[21] Appl. No.: 257,372

[22] Filed: Oct. 12, 1988

Related U.S. Application Data

[63] Continuation-in-part of Ser. No. 174,750, Mar. 29, 1988, Pat. No. 4,886,798, which is a continuation-in-part of Ser. No. 37,320, Apr. 13, 1987, Pat. No. 4,791,108.

[51] Int. Cl.[5] .................. A61K 31/47; C07D 455/03
[52] U.S. Cl. .................. 514/233.2; 514/255; 514/280; 514/285; 546/48; 546/70; 544/125; 544/361
[58] Field of Search .................. 546/70, 48; 544/125, 544/361; 514/280, 285, 255, 233.2

[56] References Cited

U.S. PATENT DOCUMENTS

| | | | |
|---|---|---|---|
| 4,076,820 | 2/1978 | Archibald et al. | 546/95 |
| 4,454,139 | 6/1984 | Ward et al. | 546/95 |
| 4,550,114 | 10/1985 | White | 514/294 |
| 4,673,680 | 6/1987 | Pendleton | 514/285 |
| 4,690,928 | 9/1987 | Huff et al. | 514/285 |
| 4,791,108 | 12/1988 | Clark | 546/70 |
| 4,886,798 | 12/1989 | Clark | 546/70 |

FOREIGN PATENT DOCUMENTS 0288196 8/1988 European Pat. Off. .............. 546/70

OTHER PUBLICATIONS

*Investigation on the Chemistry of Berbans*, Lajos Szabo, et al. *Nouv. J. Chim* 4(3), 199–202.

*Primary Examiner*—Donald G. Daus
*Attorney, Agent, or Firm*—Brian Lewis; Tom M. Moran; Alan M. Krubiner

[57] ABSTRACT

Compounds of formulas (1) and (2):

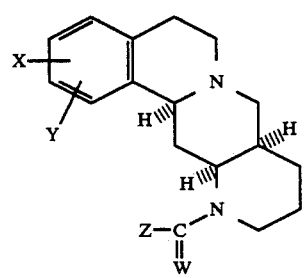

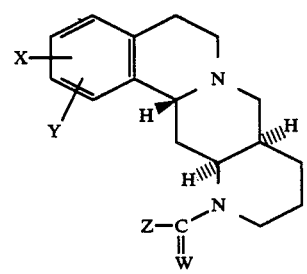

in which:

X and Y are independently hydrogen, hydroxy, lower alkyl, lower alkoxy or halo, or X and Y taken together is methylenedioxy or ethylene-1,2-dioxy;

W is oxygen or sulfur; and

Z is —R$^1$, —OR$^2$ or —NR$^3$R$^4$, wherein

R$^1$ is lower alkyl, lower haloalkyl, cycloalkyl, optionally substituted phenyl or phenyl lower alkyl, or heteroaryl;

R$^2$ is lower alkyl, optionally substituted phenyl or phenyl lower alkyl;

R$^3$ and R$^4$ are independently hydrogen, alkyl, optionally substituted phenyl or phenyl lower alkyl; or R$^3$ and R$^4$ taken together with the nitrogen to which they are attached represent a heterocycle of the formula:

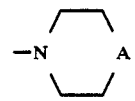

wherein A is —(CH$_2$)$_m$, —N(R$^5$)— or oxygen, in which m is an integer of 0–2 and R$^5$ is hydrogen or lower alkyl;

or a pharmaceutically acceptable salt thereof, are useful as α$_2$-blockers.

38 Claims, No Drawings

DECAHYDRO-8H-ISOQUINO(2,1-G)(1,6)NAPH-THYRIDINE DERIVATIVES AND RELATED COMPOUNDS

BACKGROUND OF THE INVENTION

1. Field of the Invention

This is a continuation-in-part of U.S. patent application Ser. No. 174,750, filed Mar. 29, 1988, now U.S. Pat. No. 4,886,798, which is a continuation-in-part of U.S. patent application Ser. No. 037,320, now U.S. Pat. No. 4,791,108, filed Apr. 13, 1987. The complete disclosures of both Patent Applications are hereby incorporated by reference.

The invention relates to various decahydro-8H-isoquino[2,1-g][1,6]naphthyridine derivatives which exhibit $\alpha_2$-blockade in mammals, and which, therefore, are useful as medicaments for the treatment of physiological conditions affected by such blockade. Such activities include, for example, lowering of blood pressure, amelioration of depression, inhibition of platelet aggregation, palliation of diabetes, alleviation of male impotence, irritable-bowel syndrome, cyclic mood disturbances in females, anxiolytic conditions, weight-loss stimulation, shortened recovery from anasthesia and lowering of intraocular pressure.

2. Previous Disclosures

The novel compounds of this invention are various decahydro-8H-isoquino[2,1-g][1,6]naphthyridine derivatives, useful as $\alpha_2$-blockers. Compounds somewhat structurally related are described in U.S. Pat. Nos. 3,953,598, 4,353,911, 4,454,139, 4,550,114, and in Nouveau J. Chim. 4(3), 199-202 (1980).

SUMMARY OF THE INVENTION

One aspect of the invention concerns novel compounds represented by the formulas:

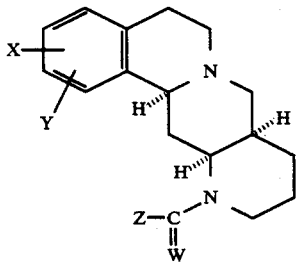
(1)

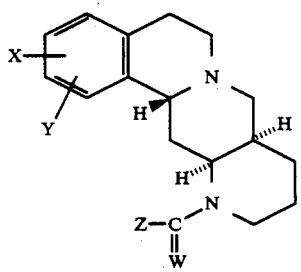
(2)

in which:

X and Y are independently hydrogen, hydroxy, lower alkyl of one to six carbon atoms, lower alkoxy of one to six carbon atoms or halo, or X and Y taken together is methylenedioxy or ethylene-1,2-dioxy;

W is oxygen or sulfur; and

Z is $-R^1$, $-OR^2$ or $-NR^3R^4$, wherein $R^1$ is lower alkyl of one to six carbon atoms, lower haloalkyl of the formula $V(CH_2)_n-$ in which V is bromo, chloro or fluoro and n is an integer of 1-6, cycloalkyl of 3-8 carbon atoms, heteroaryl, phenyl or phenyl lower alkyl in which any phenyl group may be optionally substituted by one or two substituents chosen from halo, lower alkyl of one to four carbon atoms and lower alkoxy of one to four carbon atoms;

$R^2$ is lower alkyl of one to six carbon atoms, phenyl or phenyl lower alkyl in which any phenyl group may be optionally substituted by one or two substituents chosen from halo, lower alkyl of one to four carbon atoms and lower alkoxy of one to four carbon atoms;

$R^3$ and $R^4$ are independently hydrogen, alkyl of one to eight carbon atoms, phenyl or phenyl lower alkyl in which any phenyl group may be optionally substituted by one or two substituents chosen from halo, lower alkyl of one to four carbon atoms and lower alkoxy of one to four carbon atoms; or $R^3$ and $R^4$ taken together with the nitrogen to which they are attached represent a heterocycle of the formula:

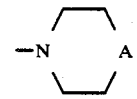

wherein A is $-(CH_2)_m$, $-N(R^5)-$ or oxygen, in which m is an integer of 0-2 and $R^5$ is hydrogen or lower alkyl;

with the proviso that for the compound of formula (2) where X is 2-methoxy, Y is 3-methoxy and W is oxygen Z cannot be methyl;

or a pharmaceutically acceptable salt thereof, are useful as $\alpha_2$-blockers.

Other aspects of the invention relate to the method of preparation of compounds of formulas (1) and (2) as racemic mixtures and as optically pure isomers, to pharmaceutical compositions containing such compounds in admixture with one or more pharmaceutically acceptable, non-toxic carriers, and to methods pertaining to their use.

DETAILED DESCRIPTION OF THE INVENTION

Definitions

As used herein:

"Alkyl" means a branched or unbranched saturated hydrocarbon chain containing 1 to 8 carbon atoms, such as methyl, ethyl, propyl, tert-butyl, n-hexyl, n-octyl and the like.

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated.

"Lower alkoxy" means the group —O—(lower alkyl) wherein lower alkyl is as herein defined.

"Cycloalkyl" as used herein means a saturated monovalent monocyclic hydrocarbon radical containing 3-8 carbon atoms, such as cyclopropyl, cyclobutyl, cyclopentyl, cyclohexyl, cycloheptyl and cyclooctyl.

"Halo" as used herein denotes fluoro, chloro, bromo, or iodo.

"Phenyl" as used herein encompasses all possible isomeric phenyl radicals optionally monosubstituted or disubstituted with a substituent selected from the group consisting of lower alkyl, lower alkoxy, hydroxy, trifluoromethyl and halo.

"Phenyl lower alkyl" as used herein denotes phenyl as defined above attached to a lower alkyl group as defined above.

"Heteroaryl" as used herein denotes a heteroatom containing aromatic radical, for example furan-2-yl, thiophen-2-yl, pyrid-2-yl, pyrid-4-yl, and the like.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl; "optionally followed by converting the free base to the acid addition salt" means that said conversion may or may not be carried out in order for the process described to fall within the invention, and the invention includes those processes wherein the free base is converted to the acid addition salt and those processes in which it is not.

The terms "α and β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn.

The compounds of formula (1) and (2) have three or more asymmetric centers. Accordingly, they may be prepared in either optically active form or as a racemic mixture. The scope of the invention as described and claimed encompasses the individual optical isomers and non-racemic mixtures thereof as well as the racemic forms of the compounds of formula (1) and (2).

The term "(±)" is used to designate a racemic of individual (+) and (−) isomers. When the mixture compound of formula (1) or (2) is a pure enantiomer, the stereochemistry at each chiral carbon atom (8a, 12a and 13a) is specified by either R or S according to the Cahn-Ingold-Prelog R-S system. In this manner relative stereochemistry is conveyed unambiguously.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture.

"Diastereoisomers" are stereoisomers which are not mirror images of each other.

"Epimers" are diastereoisomers which differ only in the configuration of one asymmetric center.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The term "disease state which is treatable with an $\alpha_2$-blocker" as used herein is intended to cover all disease states which are generally acknowledged in the art to be usefully treated with $\alpha_2$-blockers in general, and those disease states which have been found to be usefully treated by the specific $\alpha_2$-blockers of our invention, the compounds of formula (1) and (2). Such disease states include, but are not limited to, depression, anxiety, excessive platelet aggregation, diabetes, elevated intraocular pressure, male impotence, irritable bowel syndrome, hypertension, obesity, shortened recovery from anasthesia and cyclic mood disturbances in females.

The compounds of the invention will be named using the numbering system shown below.

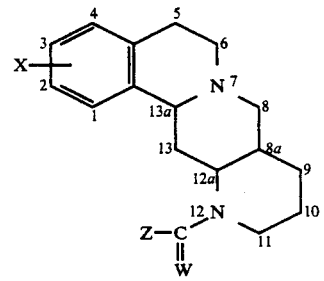

Following are examples of how representative compounds of formula (1) and (2) are named:

A racemic compound of formula (1) wherein W is oxygen, X and Y are hydrogen and Z is $R^1$, wherein $R^1$ is n-butyl is named:

(±) 12-pentanoyl-5,6,8aα,9,10,11,12,12aα,13,13aα-decahydro-8H-isoquino[2,1-g][1,6]naphthyridine.

One enantiomer of a compound of formula (1) wherein W is oxygen, X is 3-methoxy, Y is hydrogen and Z is —$OR^2$, wherein $R^2$ is ethyl is named:

(8aR,12aS,13aS)-3-methoxy-12-ethoxycarbonyl-5,6,8a,9,10,11,12,12a,13,13a-decahydro-8H-isoquino[2,1-g][1,6]naphthyridine A racemic compound of formula (2) wherein W is oxygen, X and Y taken together is 2,3-methylenedioxy and Z is —$NR^3R^4$, wherein $R^3$ and $R^4$ are both methyl, is named:

(±)-2,3-methylenedioxy-12-(N,N-dimethylamino)-carbonyl-5,6,8aα,9,10,11,12,12aβ,13,13aα-decahydro-8H-isoquino[2,1-g][1,6]naphthyridine.

Preferred Embodiments

Among the family of compounds of the present invention, a preferred group includes compounds of formula (1). Within this group a preferred subgroup includes the compounds in which X and Y are independently hydrogen or lower alkoxy, or X and Y taken together is methylenedioxy. One preferred class within this subgroup includes compounds in which W is oxygen and Z is —$R^1$, especially where $R^1$ is lower alkyl or $V(CH_2)_n$—. A second preferred class within this subgroup includes compounds in which W is oxygen and Z is —$OR^2$, especially where $R^2$ is benzyl. A third preferred class within this subgroup includes compounds in which W is oxygen and Z is —$NR^3R^4$, especially where $R^3$ and $R^4$ are independently hydrogen or lower alkyl, in particular where $R^3$ and $R^4$ are both methyl, or where $R^3$ is phenyl, benzyl or (R)-(+)-1-phenylethyl and $R^4$ is hydrogen.

A second preferred group includes compounds of formula (2). Within this group a preferred subgroup includes the compounds in which X and Y are independently hydrogen or lower alkoxy, or X and Y taken together is methylenedioxy, especially where W is oxygen and Z is —$NR^3R^4$.

At present, the preferred compounds are:
(8aR,12aS,13aS)-12-N,N-dimethylaminocarbonyl-5,6,8a,9,10,11,12,12a,13,13a-decahydro-8H-isoquino[2,1-g][1,6]naphthyridine hydrochloride;
(8aR,12aS,13aS)-3-methoxy-12-N,N-dimethylaminecarbonyl-5,6,8a,9,10,11,12,12a,13,13a-decahydro-8H-isoquino[2,1-g][1,6]naphthyridine hydrochloride;
(8aR,12aS,13aS)-2,3-methylenedioxy-12-N,N-dimethylaminocarbonyl-5,6,8a,9,10,11,12,12a,13,13a-decahydro-8H-isoquino[2,1-g][1,6]naphthyridine hydrochloride;
(8aR,12aS,-13aS)12-benzylaminocarbonyl-5,6,8a,9,10,11,12,12a,13,13a-decahydro-8H-isoquino[2,1-g][1,6]naphthyridine hydrochloride;
(8aR,12aS,13aS)-3-methoxy-12-phenylaminocarbonyl-5,6,8a,9,10,11,12,12a,13,13a-decahydro-8H-isoquino[2,1-g][1,6]naphthyridine hydrochloride;
(8aR,12aS,13aS)-12-benzoyl-5,6,8a,9,10,11,12,12a,13,13a-decahydro-8H-isoquino[2,1-g][1,6]naphthyridine hydrochloride;
(8aR,12aS,13aS)-3-methoxy-12-bromoacetyl-5,6,8a,9,10,11,12,12a,13,13a-decahydro-8H-isoquino[2,1-g][1,6]naphthyridine hydrochloride; and
(8aR,12aS,13aS)-3-methoxy-12-(2,2-dimethylpropanoyl-5,6,8a,9,10,11,12,12a,13,13a-decahydro-8H-isoquino[2,1-g][1,6]naphthyridine hydrochloride.

Methods of the Preparation

The racemic compounds of formula (1) and (2) are prepared from the intermediates of formula (VII) and (VIII), the preparation of which is illustrated below in Reaction Scheme I.

It should be understood that the structures illustrated in Reaction Scheme I are intended to represent racemic mixtures although, for the sake of clarity, only one enantiomer is shown.

REACTION SCHEME I

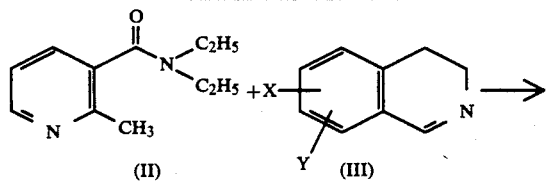

-continued
REACTION SCHEME I

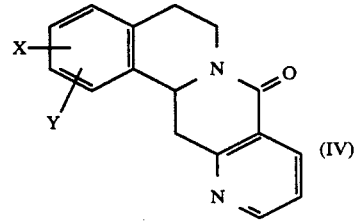

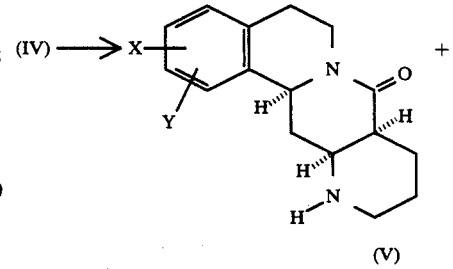

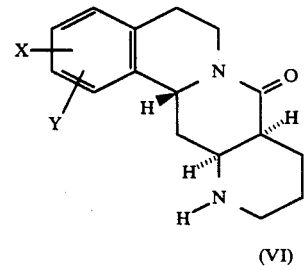

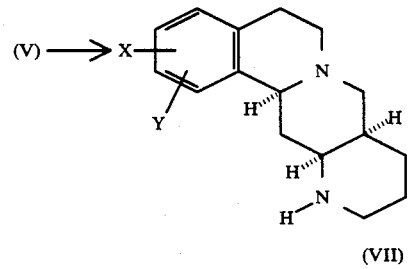

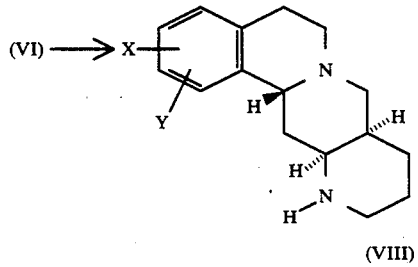

The intermediate of formula (II), 2-methylnicotinic acid diethylamide, is prepared according to the method disclosed in Ber., 72B, 563 (1939). The intermediates of formula (III), optionally substituted dihydroisoquinolines, are prepared according to the method of Bischler-Napieralski, disclosed in Organic Reactions, Vol. VI, p 74 (1951), by the cyclization of formamides of commercially available optionally substituted phenylethylamines. To prepare the compounds of formula (IV), the compounds of formula (II) and (III) are reacted together in the presence of a strong base, for example potassium t-butoxide, sodamide, sodium triphenylmethane, lithium diethylamide or preferably lithium diisopropylamide. The reaction is preferably carried out in an ethereal solvent, for example diethyl ether, dimethoxyethane, dioxane or tetrahydrofuran, at a temperature of about 0° C. to −50° C., preferably at about −10° C. to −40° C., for about 30 minutes to 4 hours. For example, diisopropylamine is dissolved in an ethereal solvent, preferably tetrahydrofuran, and cooled to temperature of about −20° to −80° C., preferably about −65° C. To the cooled solution about 1 molar equivalent of an alkyl lithium, preferably 1.6M n-butyllithium, is added. To this cold solution is added a mixture of about molar equivalent of the compound of formula (II) and about 1 molar equivalent of the compound of formula (III) in an ethereal solvent, preferably tetrahydrofuran. The reaction mixture is allowed to warm to about −10° to −40° C., preferably about −20° C., over a period of about 1 hour, and the reaction then quenched with an acid, preferably hydrochloric acid. The product of formula (IV), a (±)-5,6,13,13a-tetrahydroisoquino[2,1-g][1,6]naphthyridine-8-one hydrochloride, is isolated and purified by conventional means, preferably recrystallization of an acid salt.

The compound of formula (IV) as an acid salt or the free base, preferably as the free base, is then hydrogenated with a suitable heterogeneous catalyst, for example palladium on carbon, platinum oxide or preferably rhodium on alumina, to give a mixture of the diastereoisomers of formula (V) and (VI). For example, for every gram of the compound of formula (III) in a solution of acetic acid is added from 0.1 to 0.6 g, preferably about 0.25 g, of 5% rhodium on alumina catalyst and the mixture hydrogenated at a pressure of about 25-80 psi, preferably about 50 psi. The reaction is conducted at a temperature of about 0° to 50° C., preferably about 25° C., for about 24-72 hours, preferably about 42 hours. When the reaction is substantially complete, the mixture of compounds of formula (IV) and (V) is isolated by conventional means and the mixture chromatographed on silica gel, eluting with a suitable solvent mixture, for example 5-20% methanol in methylene chloride. The first component eluted is the compound of formula (VI), followed by the compound of formula (V).

The compounds of formula (V) and (VI) are then individually reduced to the compounds of formula (VII) and (VIII) with a suitable reducing agent, for example borane, triethyloxonium fluoroborate followed by sodium borohydride, sodium borohydride in the presence of a carboxylic acid, or preferably lithium aluminum hydride. For example, a solution of a compound of formula (V) in an ethereal solvent, preferably tetrahydrofuran, is slowly added to a solution of about 1 to 4 molar equivalents, preferably about 1.5 to 2 molar equivalents, of lithium aluminum hydride in the same ethereal solvent at about 25° C. The mixture is then refluxed for about 1–10 hours, preferably about 3 hours. When the reaction is substantially complete the compound of formula (VII) is separated and purified by conventional means, for example recrystallization of an acid salt. In a similar fashion the compound of formula (VI) is reduced to the compound of formula (VIII). and likewise separated and purified.

In a similar fashion the compounds of formula (VII) and (VIII) are obtained as a mixture if the above reduction is carried out on a mixture of the compounds of formula (V) and (VI). Such a mixture is obtained if the step of chromatographic separation is omitted from the procedure above for the preparation of the compounds of formula (V) and (VI).

The compounds of formula (1) and (2) may be prepared in optically pure form from the individual enantiomers of the intermediates of formula (VII) and (VIII), the preparation of which is illustrated in Reaction Scheme II using (VII) as an example. The two enantiomers of formula (VII) are designated as (VIIA) and (VIIB), and the two enantiomers of formula (VIII) are designated as (VIIIA) and (VIIIB).

REACTION SCHEME II

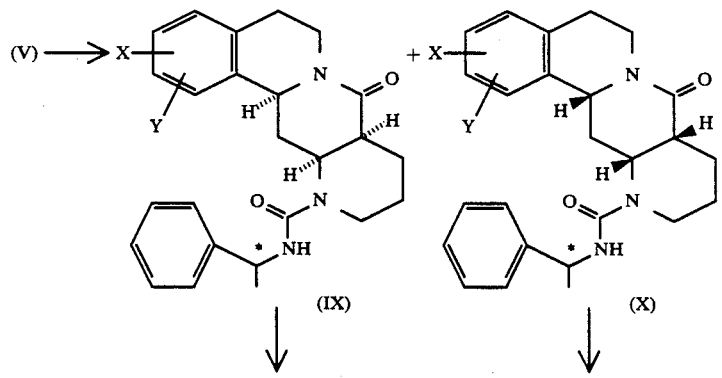

REACTION SCHEME II
-continued

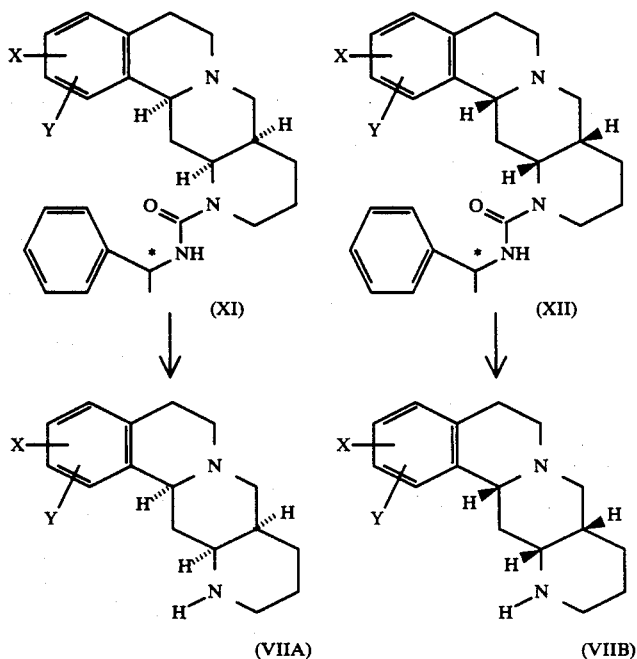

(XI)   (XII)

(VIIA)   (VIIB)

The racemic mixture of formula (V) may be separated into its two enantiomers by conventional resolution means; for example by separation (e.g. fractional crystallization) of the diastereomeric salts formed by the reaction of these compounds with optically active acids, at temperatures between 0° C. and the reflux temperature of the solvent employed for fractional crystallization. Exemplary of such optically active acids are the optically active forms of camphor-10-sulfonic acid, 2-bromo-camphor-10-sulfonic acid, camphoric acid, menthoxyacetic acid, tartaric acid, malic acid, mandelic acid, diacetyltartaric acid, pyrrolidine-5-carboxylic acid and the like. The preferred optically active acid is d-camphor-10-sulfonic acid, and the preferred solvent for recrystallization is ethyl acetate or a lower alkanol, for example methanol or ethanol, optionally with acetone as a cosolvent. The separated pure diastereomeric salts may then be cleaved by standard means, such as treatment with a base, to afford the respective enantiomers of the compound of formula (V). Conversion of the separated enantiomers of formula (V) to the compounds of formula (VIIA) and (VIIB) is then carried out as shown above in Reaction Scheme I for the conversion of the compound of formula (V) to the compound of formula (VII).

Other methods of enantiomer separation include reacting the racemic amine (V) with a chiral acid, for example 2R,3R-(+)-tartaric acid, using methods well known in the art, forming a mixture of two diastereoisomeric amides, which may be separated conventionally, for example by chromatography. Alternatively, reaction with chiral chloroformate, for example R (—)-menthyl chloroformate, gives two diastereoisomeric carbamates, which may also be separated conventionally.

Racemic mixtures may also may be separated by chromatography on a chiral column. For example, on an $\alpha_1$-acid glycoprotein column eluting with a phosphate buffer composition.

Preferably, the compound of formula (V) is reacted with a chiral isocyanate to form a mixture of two diastereoisomeric ureas of formula (IX) and (X). For example, the compound of formula (V) is dissolved in an inert solvent for example benzene, toluene, ethyl acetate, tetrahydrofuran, diethyl ether chloroform or Preferably dichloromethane, containing about 1 molar equivalent of a chiral isocyanate, preferably (R)-(+)-α-methylbenzylisocyanate. The reaction is conducted at a temperature of about 0° to 50° C., preferably about 25° C., for about 5 minutes to 4 hours, preferably about 30 minutes. When the reaction is substantially complete, the mixture of compounds of formula (IX) and (X) is isolated by conventional means. The two diastereoisomers are then preferably separated by chromatography on silica gel, especially medium pressure chromatography. The first component eluted is the compound of formula (IX), followed by the compound of formula (X). It should be noted that the compounds of formula (IX) and (X) also correspond to chiral compounds of formula (1) where Z is —$NR^3R^4$, in which $R^3$ is hydrogen and $R^4$ is (R)-(+)-1-phenylethyl.

The compounds of formula (IX) and (X) are then individually reduced to the compounds of formula (XI) and (XII) with a suitable reducing agent, for example borane, triethyloxonium fluoroborate followed by sodium borohydride, sodium borohydride in the presence of a carboxylic acid, or preferably lithium aluminum hydride. For example, a solution of a compound of formula (IX) in an ethereal solvent, preferably tetrahydrofuran, is slowly added to a solution of about 1 to 4 molar equivalents, preferably about 1.5 to 2 molar equivalents, of lithium aluminum hydride in the same ethereal solvent at about 25° C. The mixture is then refluxed for about 1-10 hours, preferably about 3 hours. When the reaction is substantially complete, the compound of formula (XI) is separated and purified by conventional means. In a similar fashion, the compound of formula (X) is reduced to the compound of formula (XII), and likewise separated and purified.

The compounds of formula (XI) and (XII) are then individually hydrolyzed to the enantiomers of formula (VIIA) and (VIIB). Typically, the compound of formula (XI) is dissolved in a protic solvent, for example ethanol, propanol or preferably n-butanol, and added to a solution containing about 4 to 30 molar equivalents, preferably about 10 molar equivalents, of sodium dissolved in the same solvent. The mixture is refluxed for about 1–10 hours, preferably about 4 hours. When the reaction is substantially complete, the compound of formula (VIIA) is separated and purified by conventional means, preferably chromatography. In a similar fashion, the compound of formula (XII) is hydrolyzed to the compound of formula (VIIB), and likewise separated and purified.

It should be noted that separation into optical isomers which is described above for the separation of the two enantiomers represented by the formula (V) may alternatively be carried out during the subsequent step, by the same procedures as shown above. That is, the compound of formula (V) could first be reduced with, for example, lithium aluminum hydride as shown above to a racemic mixture of the compounds represented by the formula (VII), and this racemic mixture similarly separated into its two enantiomers by the methods described supra.

Similarly, the racemic compound of formula (VI) is converted into the individual enantiomers of the compound of formula (VIII), designated as (VIIA) and (VIIIB), by following the above procedure.

Compounds of Formula (1) and (2)

Racemic compounds of formula (1) and (2) are prepared from the compounds of formula (VII) and (VIII) as depicted in Reaction Scheme III below. The same procedure is used for the preparation of the individual enantiomers of the compounds of formula (1) and (2), starting with the individual enantiomers of formula (VIIA) and (VIIB) or (VIIIA) and (VIIIB).

REACTION SCHEME III

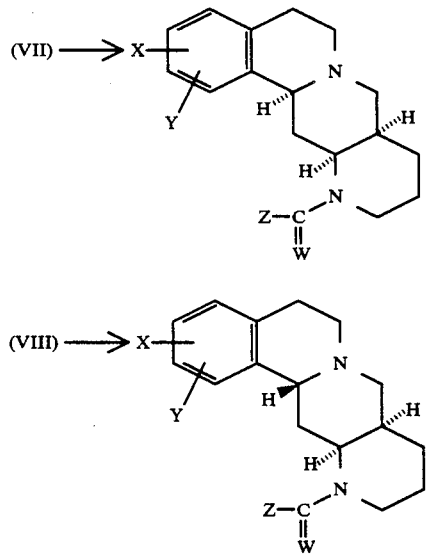

The compounds of formula (1) and (2) where Z is —$R^1$ are prepared by reacting the corresponding individual compound of formula (VII) or (VIII) with an acyl halide of the formula $R^1C(W)V$, where V is chlorine or bromine and W and $R^1$ are as defined above, or for compounds where W is oxygen with an anhydride of the formula $R^1C(O)OC(O)R^1$. The acyl halides and anhydrides are commercially available from, inter alia, Aldrich Chemical Co., or may be prepared by procedures well known in the art.

Typically, the compound of formula (VII) or (VIII) is dissolved in an inert solvent such as benzene, methylene chloride, acetonitrile, diethyl ether, chloroform, tetrahydrofuran or preferably toluene and reacted with from 1 to 3 molar equivalents, preferably about 1.2 molar equivalents, of the chosen anhydride or acid halide, preferably an acid chloride, in the presence of about 1–5 molar equivalents, preferably about 1.2 molar equivalents, of an inorganic base such as sodium carbonate, potassium bicarbonate or the like, or preferably a tertiary organic base, such as pyridine, N-methylpiperidine and the like, preferably triethylamine. Alternatively the reaction may be carried out in the presence of water, preferably using sodium carbonate as the base. The reaction is carried out at a temperature of about 0°–40° C., preferably about 25°, for about 1–10 hours, preferably about 2 hours. When the reaction is substantially complete, the product of formula (1) or (2) where Z is $R^1$ is isolated and purified by conventional means, preferably chromatography.

The compounds of formula (1) and (2) where Z is —$OR^2$ are prepared by reacting the corresponding individual compound of formula (VII) or (VIII) with a compound of the formula $R^2OC(W)L$, where L is a leaving group chosen to be capable of displacement by a secondary amine and $R^2$ and W are as defined above. For example, L may be halo, 1-imidazolyl, trichloromethoxy, optionally substituted phenoxy, such as 2,4-dichlorophenoxy, 4-methoxyphenoxy, and the like. Typically, the compound of formula (VII) or (VIII) is dissolved in an inert solvent as defined above, preferably toluene, and reacted with from 1 to 3 molar equivalents, preferably about 1.2 molar equivalents, of the chosen compound of the formula $R^2OC(W)L$, where L is as defined above, preferably chloro, in the presence of about 1–5 molar equivalents, preferably about 2.2 molar equivalents, of an inorganic base such as sodium carbonate, potassium bicarbonate or the like, or preferably a tertiary organic base, such as pyridine, N-methylpiperidine and the like, preferably triethylamine. Alternatively the reaction may be carried out in the presence of water preferably using sodium carbonate as the base. The reaction is carried out at a temperature of about 0°–40° C. Preferably about 25°. for about 5–30 hours, preferably about 15 hours. When the reaction is substantially complete, the product of formula (1) or (2) where Z is —$OR^2$ is isolated and purified by conventional means, preferably chromatography.

Any alkyl or aryl chloroformates or chlorothioformates that are not commercially available are prepared, for example, by reaction of phosgene or thiophosgene with one equivalent of the appropriate alcohol or phenol in the presence of a base. The reactions are described in greater detail in *Comprehensive Organic Chemistry*, by Barton and Ollis, vol. 2, pp 1078–1083 and Vol 3, pp 432–4.

The compounds of formula (1) and (2) where Z is —$NR^3R^4$ may be prepared by reacting the corresponding individual compound of formula (VII) or (VIII)

with a compound of the formula R³R⁴NC(W)Cl, where neither R³ or R⁴ is hydrogen. Typically, the compound of formula (VII) or (VIII) is dissolved in an inert solvent as defined above, preferably methylene chloride, and reacted with from 1 to 3 molar equivalents, preferably about 1.1 molar equivalents, of the compound of the formula R³R⁴NC(W)Cl in the presence of about 1-10 molar equivalents, preferably about 4 molar equivalents, of an inorganic base such as sodium carbonate, potassium bicarbonate or the like, or preferably a tertiary organic base, such as pyridine, N-methylpiperidine and the like, preferably triethylamine. The reaction is carried out at a temperature of about 0°-40° C., preferably about 25° C., for about 5-30 hours, preferably about 16 hours. When the reaction is substantially complete, the product of formula (1) or (2) where Z is —NR³R⁴ is isolated and purified by conventional means, preferably chromatography.

Alternatively, the compounds of formula (1) and (2) where Z is —NR³R⁴ where R³ is hydrogen and R⁴ is other than hydrogen may be prepared by reacting the corresponding individual compound of formula (VII) or (VIII) with an isocyanate or thioisocyanate of the formula R⁴NCW. Typically, the compound of formula (VII) or (VIII) is dissolved in an inert solvent as defined above, preferably toluene, and reacted with from 1 to 1.5 molar equivalents, preferably about 1.0 molar equivalents, of the compound of formula R⁴NCW. The reaction is carried out at a temperature of about 0°-40° C., preferably about 25°, for about 5-30 hours, preferably about 16 hours. When the reaction is substantially complete, the product of formula (1) or (2) where Z is —NHR⁴ is isolated and purified by conventional means, preferably chromatography.

The compounds of formula (1) and (2) where Z is —C(W)NH₂ are prepared by reacting the corresponding individual compound of formula (VII) or (VIII) with potassium isocyanate or isothiocyanate.

Alternatively, the compounds of formula (1) and (2) where Z is —NR³R⁴ may be prepared by first reacting the corresponding individual compound of formula (VII) or (VIII) with phosgene or thiophosgene, then reacting the resultant carbamoyl chloride or thiocarbamyl chloride with an amine of formula HNR³R⁴. For example, the compound of formula (VII) or (VIII) is reacted with from 1-10 molar equivalents, preferably about 2 molar equivalents, of phosgene in an inert organic solvent as defined above, preferably benzene. The reaction takes place in the presence of from 1-5 molar equivalents, preferably about 2 molar equivalents of a tertiary organic base such as triethylamine or preferably pyridine. The reaction is conducted at from 0°-50° C., preferably about 25° C., for about 1-48 hours, preferably about 16 hours, and then filtered. To the filtrate is added from 1-5 molar equivalents, preferably about 2 molar equivalents of an organic base of the formula HNR³R⁴, and the mixture stirred at about 0°-50° C., preferably about 25° C., for about 1-12 hours, preferably about 2 hours. When the reaction is substantially complete, the product of formula (1) or (2) where Z is —NR³R⁴ is isolated and purified by conventional means, preferably chromatography.

An alternative procedure for the preparation of compounds of formula (1) and (2) is from the mixture of compounds (VII) and (VIII) obtained as shown above in Reaction Scheme I. The mixture of compounds (VII) and (VIII) is treated with the appropriate reagent in the same manner as shown above to give the desired definition of Z, giving a mixture of the compounds of formula (1) and (2) which is separated by conventional means, preferably chromatography, into the individual diastereoisomers of formula (1) and (2).

An alternative preparation of the compound of formula (1) where W is oxygen is shown in Reaction Scheme IV below.

REACTION SCHEME IV

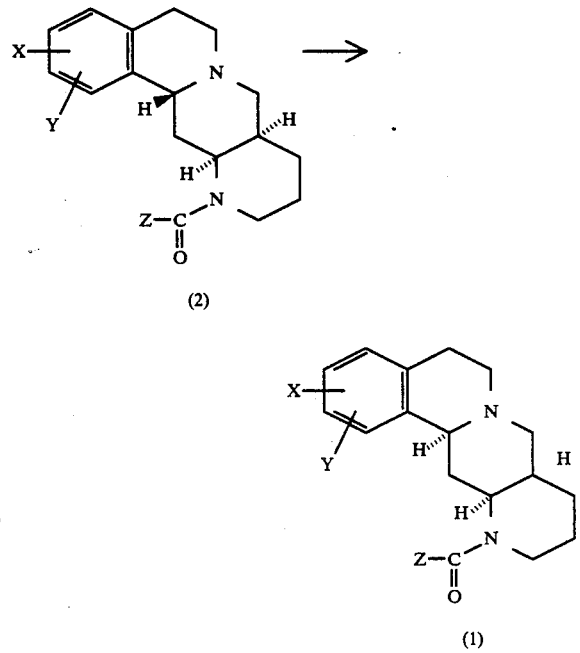

In this procedure the compound of formula (2), prepared as shown in Reaction Scheme III, is converted to the compound of formula (1).

Typically, the compound of formula (2) is first oxidized with about 1-10 molar equivalents, preferably about 4 molar equivalents, of an oxidizing agent. Representative oxidizing agents are iodine pentafluoride, Hg(II) salts, Pb(IV) salts, Ni(I) salts, Ag(II) salts, N-bromo and N-chlorosuccinimide, Cl₂ and the like. A preferred oxidizing agent is a mercuric salt, preferably mercuric acetate. The compound of formula (2) and mercuric acetate are combined in acetic acid containing from about 5%-50%, preferably about 10%, of water and the mixture heated at a temperature of about 70° C. to the reflux temperature, preferably about 105° C., for about 30 minutes to 4 hours, preferably about 1 hour. After filtering, hydrogen sulfide is passed through, followed by refiltering and removal of the solvent from the filtrate. The residue is then dissolved in a protic solvent, preferably ethanol, the solution cooled to a temperature of about 0° to −40° C., preferably about 20° C., and treated with about 1 to 10 molar equivalents, preferably about 4 molar equivalents, of sodium borohydride. When the reaction is substantially complete the compound of formula (1) is isolated by conventional means, for example chromatography.

Alternatively, the conversion of a compound of formula (2) to (1) may be carried out by dissolving the compound of formula (2) in an inert solvent, preferably chloroform, at a temperature of about −20° to 10° C., preferably about 0° C., and treated with about 0.9 to 2 molar equivalents, preferably about 1.4 molar equivalents, of an oxidizing agent such as peracetic acid, perbenzoic acid or preferably metachloroperbenzoic acid, for about 10 minutes to 4 hours, preferably about 30 minutes, followed by about 20 minutes at room temperature. The reaction mixture is then recooled to about −20° to 10° C., preferably about 0° C., and treated with about 1 to 20 molar equivalents, preferably about 5.5 molar equivalents, of trifluoroacetic anhydride. The reaction is carried out at a temperature of about 10° to 30° C., preferably about 20° C., for about 5 minutes to about 2 hours, preferably about 30 minutes. The solvent is then removed under reduced pressure, and a protic solvent added, preferably ethanol. An excess of a reducing agent, preferably sodium borohydride, is then added slowly at a temperature of about −10° to 20° C., preferably about 0° C., until the solution becomes basic. When the reaction is substantially complete the compound of formula (1) is isolated by conventional means, for example chromatography or preferably recrystallization.

A mixture of compounds of formula (1) and (2) may replace the compound of formula (2) as a starting material in the procedure described above, giving rise to the same product of formula (1). Such a mixture of compounds of formula (1) and (2) is obtained as shown in Reaction Scheme III.

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples hereinbelow. However, other equivalent separation or isolation procedures could, of course, also be used.

The salt products are also isolated by conventional means. For example, the reaction mixtures may be evaporated to a dryness, and the salts can be further purified by conventional methods such as those listed above.

Salts of Compounds of Formula (1) and (2)

The compounds of formula (1) and (2) may be converted to a corresponding acid addition salt by virtue of the presence of the tertiary nitrogen atoms.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

The acid addition salts of the compounds of formula (1) and (2) may be converted to the corresponding free bases by treatment with at least a stoichiometric amount of a suitable base such as sodium or potassium hydroxide, potassium carbonate, sodium bicarbonate, ammonia, and the like.

Utility and Administration

The compounds of formula (1) and (2) and the pharmaceutically acceptable acid addition salts thereof have been found to possess valuable pharmacological properties in the central nervous system and, in particular, have been shown to selectively block $\alpha_2$-receptors in standard laboratory tests. Accordingly these compounds and pharmaceutically acceptable compositions containing them are useful in the regulation of physiological phenomena related to $\alpha_2$-receptors, including lowering of blood pressure, amelioration of depression, inhibition of platelet aggregation, palliation of diabetes, alleviation of male impotence, weight-loss stimulation and lowering of intraocular pressure (useful in treating e.g. glaucoma). In addition, the compounds of formula (1) and (2) are useful for the treatment of irritable-bowel syndrome, shortening recovery time from anasthesia, cyclic mood disturbances in females and conditions of anxiety.

In applying the compounds of this invention to treatment of conditions which are regulated by the CNS, administration of the active compounds and salts described herein can be via any of the accepted modes of administration for agents which relieve depression or affect the central nervous system including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of formula (1) and (2) or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 0.001–10 mg/kg/day, preferably 0.05–1 mg/kg/day. For an average 70 kg human, this would amount to 0.07–700 mg per day, or preferably 3.5–70 mg/day.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient (compounds of formula (1) and (2) or its salts) in the range of 0.25 to 95% with the balance made up from non-toxic carrier may be prepared.

For oral administration, a pharmaceutically acceptable non toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like.

Such compositions may contain 1% 95% active ingredient, preferably 5-50%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably the composition will comprise 0.2-2% of the active agent in solution.

For systemic administration via suppository, traditional binders and carriers include, e.g. polyalkalene glycols or triglycerides. Such suppositories may be formed from mixtures containing active ingredient in the range of 0.5%-10%; preferably 1-2%.

In applying the compounds of the invention to treatment of diseases or disorders of the eye which are associated with an abnormally high intraocular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.001% to 10%, most preferably 0.005% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6-8. Typical sterilants are phenyl mercuric acetate, thimerosal, chlorobutanol, and benzalconium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8-8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, a typical ocular composition could be administered at the rate of about 2-10 drops per day per eye of a 0.1% solution of active ingredient.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, PH buffering agents, surface active agents, and the like. Actual methods of preparing such dosage forms are known, or will be apparent, to those skilled in the art; for example, see *Remington's Pharmaceutical Sciences*, Mack Publishing Company Easton, Pa., 16th Edition, 1980.

The following preparation and examples illustrate the invention but are not intended to limit its scope.

PREPARATION 1

Preparation of (±)-5,6,13,13a-Tetrahydroisozuino-[2,1-g][1,6]naphthyridin-8-one hydrochloride and Related Compounds of Formula (IV).

A. Diisopropylamine (28 ml) and 150 ml of tetrahydrofuran were cooled to −65° C. and 125 mL of 1.6M n-butyllithium was added. To the resulting solution was added a solution of 16.2 g of 3,4-dihydroisoquinoline and 38.4 g of 2-methylnicotinic acid diethylamide in tetrahydrofuran. The mixture was allowed to warm to −20° C. and 600 ml of 3N hydrochloric acid was then added followed by 200 ml of water. The mixture was basified with NH$_4$OH and extracted twice with ether. The ether extracts were combined, dried over anhydrous magnesium sulfate and evaporated to a residue, which was dissolved in methanol and acidified with anhydrous HCl in ether. Acetone (50 ml) was added and the mixture was allowed to stand overnight. The crystalline product was collected by filtration, yielding 34 g of (±) 5,6,13,13a-tetrahydroisoquino[2,1-g][1,6]naphthyridine-8-one hydrochloride, m.p. 220°-222° C.

An additional 7.5 g of the title compound as the free base was obtained by evaporation of the mother liquor followed by partitioning between ether and aqueous NH$_4$OH and silica gel chromatography of the residue obtained from evaporation of the ether, eluting with ethyl acetate, giving the free base, m.p. 72°-73° C.

B. Similarly, replacing 3,4-dihydroisoquinoline with the appropriate compound of formula (III) and following the procedure in paragraph A above, the following compounds of formula (IV) were prepared:

(±)-3-methoxy-5,6,13,13a-tetrahydroisoquino-[2,1-g][1,6]naphthyridine-8-one hydrochloride, m.p. 244°-246° C.;

(±)-3-methoxy-5,6,13,13a-tetrahydroisoquino-[2,1-g][1,6]naphthyridine-8-one, m.p. 115°-116° C.;

(±)-2,3 dimethoxy-5,6,13,13a-tetrahydroisoquino-[2,1 g][1,6]naphthyridine-8-one hydrochloride, m.p. 238°-240° C.;

(±)-1,4-dimethoxy-5,6,13,13a-tetrahydroisoquino-[2,1-g][1,6]naphthyridine-8-one hydrochloride;

(±)-2,3-methylenedioxy 5,6,13,13a-tetrahydroisoquino-[2,1-g][1,6]naphthyridine-8-one, m.p. 177°-179° C.; and (±)-2,3-(ethylene-1,2-dioxy)-5,6,13,13a-tetrahydroisoquino-[2,1-g][1,6]naphthyridine-8-one.

C. Similarly, replacing 3,4-dihydroisoquinoline with other compounds of formula (III) and following the procedure in paragraph A above, the following exemplary compounds of formula (IV) are prepared:

(±)-1-methyl-5,6,13,13a-tetrahydroisoquino-[2,1-g][1,6]naphthyridine-8-one hydrochloride;

(±) -2-methyl-5,6,13,13a-tetrahydroisoquino-[2,1-g][1,6]naphthyridine-8-one hydrochloride;

(±)-3-methyl-5,6,13,13a-tetrahydroisoquino)-[2,1-g][1,6]naphthyridine-8-one hydrochloride;

(±)-2,3 dimethyl-5,6,13,13a-tetrahydroisoquino-[ 2,1-g][1,6]naphthyridine-8-one hydrochloride;

(±)-3-ethyl-5,6,3,13,13a-tetrahydroisoquino-[2,1,-g][1,6]naphthyridine-8-one hydrochloride;

(±)-3-isobutyl-5,6,13,13a-tetrahydroisoquino-[2,1-g][1,6]naphthyridine-8-one hydrochloride;

(±)-3-n-hexyl 5,6,13,13a-tetrahydroisoquino-[2,1-g][1,6]naphthyridine-8-one hydrochloride;

(±)-1-methoxy-5,6,13,13a-tetrahydroisoquino-[2,1-g][1,6]naphthyridine-8-one hydrochloride;

(±)-2-methoxy-5,6,13,13a-tetrahydroisoquino-[2,1-g][1,6]naphthyridine-8-one hydrochloride;

(±)-4-methoxy-5,6,13,13a-tetrahydroisoquino-[2,1-g][1,6]naphthyridine-8-one hydrochloride;

(±)-3-methoxy-2-methyl-5,6,13,13a-tetrahydroisoquino-[2,1-g][1,6]naphthyridine-8-one hydrochloride;

(±)-3-ethoxy-5,6,13,13a-tetrahydroisoquino-[2,1-g][1,6]naphthyridine-8-one hydrochloride;

(±)-3-isopropoxy-5,6,13,13a-tetrahydroisoquino-[2,1-g][1,6]naphthyridine-8-one hydrochloride;

(±)-3-isobutoxy-5,6,13,13a-tetrahydroisoquino-[2,1-g][1,6]naphthyridine-8-one hydrochloride;

(±)-3-n-hexyloxy-5,6,13,13a-tetrahydroisoquino-[2,1-g][1,6]naphthyridine-8-one hydrochloride;

(±)-3-hydroxy-5,6,13,13a-tetrahydroisoquino-[2,1-g][1,6]naphthyridine-8-one hydrochloride;

(±)-2,3-dihydroxy-5,6,13,13a-tetrahydroisoquino-[ 2,1-g][1,6]naphthyridine-8-one hydrochloride;

(±)-1,2-dimethoxy-5,6,13,13a-tetrahydroisoquino-[2,1-g][1,6]naphthyridine-8-one hydrochloride;

(±)-3,4-dimethoxy-5,6,13,13a-tetrahydroisoquino-[2,1-g][1,6]naphthyridine-8-one hydrochloride;

(±)-2,3-diethoxy-5,6,13,13a-tetrahydroisoquino-[2.1-g][1,6]naphthyridine-8-one hydrochloride;

(±)-2,3-di-n-butoxy-5,6,13,13a-tetrahydroisoquino-[2,1-g][1,6]naphthyridine-8-one hydrochloride;

(±)-1,2 methylenedioxy-5,6,13,13a-tetrahydroisoquino-[2,1-g][1,6]naphthyridine-8-one hydrochloride;

(±)-3,4-methylenedioxy 5,6,13,13a-tetrahydroisoquino-[2,1-g][1,6]naphthyridine-8-one hydrochloride;

(±)-1-chloro-5,6,13,13a-tetrahydroisoquino-[2,1-g][1,6]naphthyridine-8-one hydrochloride;

(±)-2-chloro-5,6,13,13a-tetrahydroisoquino-[2,1-g][1,6]naphthyridine-8-one hydrochloride;

(±)-3-chloro-5,6,13,13a-tetrahydroisoquino-[2,1-g][1,6]naphthyridine-8-one hydrochloride;

(±)-4-chloro-5,6,13,13a-tetrahydroisoquino-[2,1-g][1,6]naphthyridine-8-one hydrochloride;

(±)-3-bromo-5,6,13,13a-tetrahydroisoquino-[2,1-g][1,6]naphthyridine-8-one hydrochloride;

(±)-3-fluoro-5,6,13,13a-tetrahydroisoquino-[2.1-g][1.6]naphthyridine-8-one hydrochloride; and (±)-2-fluoro-5,6,13,13a-tetrahydroisoquino-[2,1-g][1,6]naphthyridine-8-one hydrochloride.

PREPARATION 2

Preparation of (±)-5,6,8aα,9,10,11,12,12aα,13,-13aα-decahydroisoquino[2.1-g][1,6]naphthyridin-8-one (V) and (±)-5,6,8aβ,9,10,11,12,12aβ,13,13aα-Decahydroisoquino[2,1-g][1,6]naphthyridin-8-one (VI) and Related Compounds of Formula (V) and (VI).

A. A mixture of 30 g of (±) 5,6,13,13a-tetrahydroisoquino[2,1-g][1,6]naphthyridine-8-one, prepared as shown in Preparation 1 above, and 7.5 g of 5% Rh-Al$_2$O$_3$ in 300 ml of acetic acid was hydrogenated at 50 psi for 42 hours. The catalyst was removed by filtration and the filtrate was concentrated under reduced pressure. The residue was partitioned between methylene chloride and aqueous NH$_4$OH and the methylene chloride layer was separated and the solvent removed under reduced pressure. The residue was purified by silica gel chromatography, eluting with from 5-20% methanol in methylene chloride. The first component eluted was (±)-5,6,8aβ,9,10,11,12,12aβ,13,13aα-decahydroisoquino[2,1-g][1,6]naphthyridin-8-one (9.7 g), (VI), m.p. 105°-106° C. The second component eluted was (±)-5,6,8aα,9,10,11,12,12aα,13,13α-decahydroisoquino[2,1-g][1,6]naphthyridin-8-one (11.0 g), (V), m.p. 91°-92° C.

B. Similarly, replacing (±)-5,6,13,13a-tetrahydroisoquino-[2,1-g][1,6]naphthyridine-8-one hydrochloride with the appropriate compound of formula (IV) and following the procedure in paragraph A above, the following compounds of formula (V) and (VI) were prepared:

(±)-3-methoxy-5,6,8aβ,9,10,11,12,12aβ,13,13aα-decahydroisoquino[2,1-g][1,6]naphthyridin-8-one; and (±)-3-methoxy-5,6,8aα,9,10,11,12,12aα,13,13aα-decahydroisoquino[2,1-g][1,6]naphthyridin-8-one, m.p. 118°-119° C.;

(±)-2,3-dimethoxy-5,6,8aβ,9,10,11,12,12aβ,13,-13aα-decahydroisoquino[2,1-g][1,6]naphthyridin-8-one;

(±)-2,3-dimethoxy-5,6,8aα,9,10,11,12,12aα,13,-13aα-decahydroisoquino[2,1-g][1,6]naphthyridin-8-one;

(±)-1,4-dimethoxy-5,6,8aβ,9,10,11,12,12aβ,13,-13aα-decahydroisoquino[2,1-g][1,6]naphthyridin-8-one; and (±)-1,4-dimethoxy-5,6,8aα,9,10,11,12,12aα,13,-13aα-decahydroisoquino[2,1-g][1,6]naphthyridin-8-one;

(±)-2,3-methylenedioxy-5,6,8aβ,9,10,11,12,12aβ,13,-13aα-decahydroisoquino[2,1-g][1,6]naphthyridin-8-one; and (±)-2,3-methylenedioxy-5,6,8aα,9,10,11,12,12aα,-13,13aα-decahydroisoquino[2,1-g][1,6]naphthyridin-8-one;

(±)-2,3-(ethylene-1,2-dioxy)-5,6,8aβ,9,10,11,12,-12aβ,13,13aα-decahydroisoquino[2,1-g][1,6]naphthyridin-8-one; and (±)-2,3-(ethylene 1,2-dioxy)-5,6,8aα,9,10,11,12,-12aα,13,13aα-decahydroisoquino[2,1-g][1,6]naphthyridin-8-one.

C. Similarly, replacing (±)-5,6,13,13a-tetrahydroisoquinoisoquino[2,1-g][1,6]naphthyridine-8-one hydrochloride with other compounds of formula (IV) and following the procedure in paragraph A above, the following exemplary compounds of formula (V) and (VI) are prepared:

(±)-1-methyl-5,6,8aβ,9,10,11,12,12aβ,13,13aα-decahydroisoquino[2,1-g][1,6]naphthyridin-8-one; and (±)1-methyl-5,6,8aα,9,10,11,12,12aα,13,13aα-decahydroisoquino[2,1-g][1,6]naphthyridin-8-one;

(±)-2-methyl-5,6,8aβ,9,10,11,12,12aβ,13,13aα-decahydroisoquino[2,1-g][1,6]naphthyridin-8-one; and (±)-2-methyl-5,6,8aα,9,10,11,12,12aα,13,13aα-decahydroisoquino[2,1-g][1,6]naphthyridin-8-one;

(±)-3-methyl- 5,6,8aβ,9,10,11,12,12aβ,13,13aα-decahydroisoquino[ 2,1-g][1,6]naphthyridin-8-one; and (±)-3-methyl-5,6,8a ,9,10,11,12,12aα,13,13aα-decahydroisoquino[2,1-g][1,6]naphthyridin-8-one;

(±)-2,3-dimethyl-5,6,8aβ,9,10,11,12,12aβ,13,-13aα-decahydroisoquino[2,1-g][1,6]naphthyridin-8-one; and (±)-2,3-dimethyl-5,6,8aα,9,10,11,12,12aα,13,-13aα-decahydroisoquino[2,1-g][1,6]naphthyridin-8-one;

(±)-3-ethyl-5,6,8aβ,9,10,11,12,12aβ,13,13aα-decahydroisoquino[2,1-g][1,6]naphthyridin-8-one; and (±)-3-ethyl-5,6,8aα,9,10,11,12,12aα,13,13aα-decahydroisoquino[2,1-g][1,6]naphthyridin-8-one;

(±)-3-isobutyl-5,6,8aβ,9,10,11,12,12aβ,13,-13aα-decahydroisoquino[2,1-g][1,6]naphthyridin-8-one; and (±)-3-isobutyl-5,6,8aα,9,10,11,12,12aα,13,-13aα-decahydroisoquino[2,1-g][1,6]naphthyridin-8-one;

(±)-3-hexyl-5,6,8aβ,9,10,11,12aβ,13,13aα-decahydroisoquino[2,1-g][1,6]naphthyridin-8-one; and (±) 3-n-hexyl 5,6,8aα,9,10,11,12,12aα,13,13aα-decahydroisoquino[2,1-g][1,6]naphthyridin-8-one;

(±)-1-methoxy 5,6,8aβ,9,10,11,12,12aβ,13,13aα-decahydroisoquino[2,1-g][1,6]naphthyridin-8-one; and (±)-1-methoxy-5,6,8aα,9,10,11,12,12aα,13,13aα-decahydroisoquino[2,1-g][1,6]naphthyridin-8-one;

(±)-2-methoxy 5,6,8aβ,9,10,11,12,12aβ,13,13aα-decahydroisoquino[2,1-g][1,6]naphthyridin-8-one; and (±)-2-methoxy-5,6,8aα,9,10,11,12,12aα,13,13aα-decahydroisoquino[2,1-g][1,6]naphthyridin-8-one;

(±)-4-methoxy-5,6,8aβ,9,10,11,12,12aβ,13,13aα-decahydroisoquino[2,1-g][1,6]naphthyridin-8-one; and (±)-4-methoxy-5,6,8aβ,9,10,11,12,12aβ,13,13aα-decahydroisoquino[2,1-g][1,6]naphthyridin-8-one;

(±) 3-methoxy-2-methyl-5,6,8aα,9,10,11,12,12aβ,-13,13aα-decahydroisoquino[2,1-g][1,6]naphthyridin-8-one; and (±)-3-methoxy-2-methyl-5,6,8aα,9,10,11,12,12aα,-13,13aα-decahydroisoquino[2,1-g][1,6]naphthyridin-8-one, (±)-3-ethoxy 5,6,8aβ,9,10,11,12,12aβ,13,13aα-decahydroisoquino[2,1-g][1,6]naphthyridin-8-one; and (±)-3-ethoxy-5,6,8aα,9,10,11,12,12aα,13,13aα-decahydroisoquino[2,1-g][1,6]naphthyridin-8-one;

(±)-3-isopropoxy 5,6,8aβ,9,10,11,12,12aβ,13,-13aα-decahydroisoquino[2,1-g][1,6]naphthyridin-8-one; and (±)-3-isopropoxy-5,6,8aα,9,10,11,12aα,13,-13aα-decahydroisoquino[2,1,-g][1,6]naphthyridin-8-one;

(±)-3-isobutoxy-5,6,8aα,9,10,11,12,12aα,13,-13aα-decahydroisoquino[2,1-g][1,6]naphthyridin-8-one;

(±)-3-isobutoxy-5,6,8aβ,9,10,11,12,12aβ,13,- 13aα-decahydroisoquino[2,1-g][1,6]naphthyridin-8-one; and (±)-3-n-hexyloxy-5,6,8aβ,9,10,11,12,12aβ,13,-13aα-decahydroisoquino[2,1-g][1,6]naphthyridin-8-one; and (±)-3-n hexyloxy-5,6,8aα,9,10,11,12,12aα,13,-13aα-decahydroisoquino[2,1-g][1,6]naphthyridin-8-one;

(±)-3-hydroxy 5,6,8aβ,9,10,11,12,12aβ,13,13aα-decahydroisoquino[2,1-g][1,6]naphthyridin-8-one; and (±)-3-hydroxy-5,6,8aα,9,10,11,12,12aα,13,13aα-decahydroisoquino[2,1-g][1,6]naphthyridin-8-one;

(±)-2,3-dihydroxy-5,6,8aβ,9,10,11,12,12aβ,13,-13aα-decahydroisoquino[2,1-g][1,6]naphthyridin-8-one;

(±)-1,2-dimethoxy-5,6,8aα,9,10,11,12,12aα,13,-13aα-decahydroisoquino[2,1-g][1,6]naphthyridin-8-one; and (±)-1,2-dimethoxy-5,6,8aα,9,10,11,12,12aα,13,- 13aα-decahydroisoquino[2,1-g][1,6]naphthyridin-8-one;

(±)-1,4-dimethoxy-5,6,8aβ,9,10,11,12,12aβ,13,-13aα-decahydroisoquino[2,1-g][1,6]naphthyridin-8-one; and (±)-1,4-dimethoxy-5,6,8aα,9,10,11,12,12aα,13,-13aα-decahydroisoquino[2,1-g][1,6]naphthyridin-8-one;

(±)-3,4-dimethoxy 5,6,8aβ,9,10,11,12,12aβ,13,-13aα-decahydroisoquino[2,1-g][1,6]naphthyridin-8-one; and (±)-3,4-dimethoxy-5,6,8aα,9,10,11,12,12aα,13,-13aα-decahydroisoquino[2,1-g][1,6]naphthyridin-8-one;

(±)-2,3-diethoxy 5,6,8aβ,9,10,11,12,12aβ,13,-13aα-decahydroisoquino[2,1-g][1,6]naphthyridin-8-one; and (±)-2,3-diethoxy-5,6,8aα,9,10,11,12,12aα,13,-13aα-decahydroisoquino[2,1-g][1,6]naphthyridin-8-one;

(±)-2,3-di-n-butoxy-5,6,8aβ,9,10,11,12,12aβ,13,-13aα-decahydroisoquino[2,1-g][1,6]naphthyridin-8-one; and (±)-2,3-di-n-butoxy-5,6,8aα,9,10,11,12,12aα,13,-13aα-decahydroisoquino[2,1-g][1,6]naphthyridin-8-one;

(±)-1,2-methylenedioxy-5,6,8aβ,9,10,11,12,12aβ,13,-13aα-decahydroisoquino[2,1-g][1,6]naphthyridin-8-one; and (±)-1,2-methylenedioxy-5,6,8aα,9,10,11,12,12aα,-13,13aα-decahydroisoquino[2,1-g][1,6]naphthyridin-8-one;

(±)-2-chloro-5,6,8aβ,9,10,11,12,12aβ,13,13aα-decahydroisoquino[2,1-g][1,6]naphthyridin-8-one; and (±)-2-chloro-5,6,8aα,9,10,11,12,12aα,13,13aα-decahydroisoquino[2,1-g][1,6]naphthyridin-8-one;
(±)-3-chloro-5,6,8aβ,9,10,11,12,12aβ,13,13aα-decahydroisoquino[2,1-g][1,6]naphthyridin-8-one; and
(±)-3-chloro-5,6,8aα,9,10,11,12,12aα,13,13aα-decahydroisoquino[2,1-g][1,6]naphthyridin-8-one;
(±)-4-chloro-5,6,8aβ,9,10,11,12,12aβ,13,13aα-decahydroisoquino[ 2,1-g][1,6]naphthyridin-8-one; and
(±)-4-chloro-5,6,8aα,9,10,11,12,12aα,13,13aα-decahydroisoquino[2,1-g][1,6]naphthyridin-8-one;
(±)-3-bromo-5,6,8aβ,9,10,11,12,12aβ,13,13aα-decahydroisoquino[2,1-g][1,6]naphthyridin-8-one; and
(±)-3-bromo 5,6,8aα,9,10,11,12,12aα,13,13aα-decahydroisoquino[2,1-g][1,6]naphthyridin-8-one;
(±)-3-fluoro-5,6,8aβ,9,10,11,12,12aβ,13,13aα-decahydroisoquino[2,1-g][1,6]naphthyridin-8-one; and
(±)-3-fluoro-5,6,8aα,9,10,11,12,12aα,13,13aα-decahydroisoquino[2,1-g][1,6]naphthyridin-8-one;
(±)-2-fluoro-5,6,8aβ,9,10,11,12,12aβ,13,13aα-decahydroisoquino[2,1-g][1,6]naphthyridin-8-one; and
(±)-2-fluoro-5,6,8aα,9,10,11,12,12aα,13,13aα-decahydroisoquino[2,1-g][1,6]naphthyridin-8-one.

PREPARATION 3

Preparation of (±)
-5,6,8aβ,9,10,11,12,12aβ,13,-13aα-Decahydro-8H-isoquino[2,1g][1,6]naphthyridine and Related Compounds of formula (VII) and VIII)

A. A solution of 9.6 g of (±)-5,6,8aβ,9,10,11,12,-12aβ,13,13aα-decahydroisoquino[2,1-g][1,6]naphthyridin-8-one (V), prepared as shown in Preparation 2, in 50 ml of tetrahydrofuran was added slowly to a solution of 2.5 g of lithium aluminum hydride in 75 ml of tetrahydrofuran. The resulting mixture was stirred at reflux for 3 hours, cooled, and treated sequentially with 2.5 ml of water, 2.5 ml of 15% sodium hydroxide, and 7.5 ml of water. The mixture was filtered and the filtrate was evaporated to afford-8.8 g of (±)-5,6,8aβ,9,10,11,12,-12aβ,13,13aα-decahydro8H-isoquino[2,1-g][1,6]naphthyridine (VII) as a thick oil. The oil was dissolved in ethanol and acidified with anhydrous HCl in ether, from which a dihydrochloride salt was crystallized, m.p. 290°-295° C.

B. Similarly, replacing (±)-5,6,8aβ,9,10,11,12,-12aβ,13,13aα-decahydroisoquino[2,1-g][1,6]naphthyridin-8-one with the appropriate compound of formula (V) or (VI) and following the procedure in paragraph A above, the following compounds of formula (VII) and (VIII) were prepared:
(±)-5,6,8aα,9,10,11,12,12aα,13,13aα-decahydro 8H-isoquino[2,1-g][1,6]naphthyridine;
(±)-3-methoxy-5,6,8aβ,9,10,11,12,12aβ,13,13aα-decahydro-8H-isoquino[2,1-g][1,6]naphthyridine;
(±)-3-methoxy-5,6,8aα,9,10,11,12,12aα,13,13aα-decahydro-8H-isoquino[2,1-g][1,6]naphthyridine;
(±)-2,3-dimethoxy-5,6,8aβ,9,10,11,12,12aβ,13,-13aα-decahydro-8H-isoquino[2,1-g][1,6]naphthyridine;
(±)-2,3-dimethoxy-5,6,8aα,9,10,11,12,12aα,13,-13aα-decahydro-8H-isoquino[2,1-g][1,6]naphthyridine;
(±)-1,4-dimethoxy-5,6,8aβ,9,10,11,12,12aβ,13,-13aα-decahydro-8H-isoquino[2,1-g][1,6]naphthyridine;
(±)-1,4-dimethoxy-5,6,8aα,9,10,11,12,12aα,13,-13aα-decahydro-8H isoquino[2,1-g][1,6]naphthyridine;
(±)-2,3-methylenedioxy 5,6,8aβ,9,10,11,12,12aβ,-13,13aα-decahydro-8H-isoquino[2,1-g][1,6]naphthyridine, and
(±)-2,3-methylenedioxy-5,6,8aα,9,10,11,12,12aα,-13,13aα-decahydro-8H-isoquino[2,1-g][1,6]naphthyridine;
(±)-2,3-(ethylene-1,2-dioxy)-5,6,8aβ,9,10,11,12,-12aβ,13,13aα-decahydro-8H-isoquino[2,1-g][1,6]naphthyridine;.and
(±)-2,3-(ethylene-1,2-dioxy) 5,6,8aα,9,10,11,12,-12aα,13,13aα-decahydro-8H isoquino[2,1-g][1,6]-naphthyridine;

C. Similarly, replacing (±)-5,6,8aβ,9,10,11,12,-12aβ,13,13aα-decahydroisoquino[ 2,1-g][1,6]naphthyridin-8-one with other compounds of formula (V) or (VI) and following the procedure in paragraph A above, the following exemplary compounds of formula (VII) and (VIII) are prepared:
(±)-1-methyl-5,6,8aβ,9,10,11,12,12aβ,13,13aα-decahydro-8H-isoquino[2,1-g][1,6]naphthyridine; and
(±)-1-methyl-5,6,8aα,9,10,11,12,12aα,13,13aα-decahydro-8H-isoquino[2,1-g][1,6]naphthyridine;
(±)-2-methyl 5,6,8aβ,9,10,11,12,12aβ,13,13aα-decahydro-8H-isoquino[2,1-g][1,6]naphthyridine; and
(±)-2-methyl-5,6,8aα,9,10,11,12,12aα,13,13aα-decahydro 8H-isoquino[2,1-g][1,6]naphthyridine;
(±)-3-methyl-5,6,8aβ,9,10,11,12,12aβ,13,13aα-decahydro 8H-isoquino[2,1-g][1,6]naphthyridine; and
(±)-3-methyl-5,6,8aα,9,10,11,12,12aα,13,13aα-decahydro-8H isoquino[2,1-g][1,6]naphthyridine;
(±)-2,3-dimethyl-5,6,8aβ,9,10,11,12,12aβ,13,-13aα-decahydro-8H-isoquino[2,1-g][1,6]naphthyridine; and
(±)-2,3-dimethyl-5,6,8aα,9,10,11,12,12aα,13,-13aα-decahydro-8H-isoquino[21-g][1,6]naphthyridine;
(±)-3-ethyl-5,6,8aβ,9,10,11,12,12aβ,13,13aα-decahydro-8H-isoquino[2,1-g][1,6]naphthyridine; and
(±)-3-ethyl-5,6,8aα,9,10,11,12,12aα,13,13aα-decahydro-8H-isoquino[2,1-g][1,6]naphthyridine;
(±)-3-isobutyl-5,6,8aβ,9,10,11,12,12aβ,13,-13aα-decahydro-8H-isoquino[2,1-g][1,6]naphthyridine; and
(±)-3-isobutyl-5,6,8aα,9,10,11,12,12aα,13,-13aα-decahydro-8H-isoquino[2,1-g][1,6]naphthyridine;
(±)-3-n hexyl-5,6,8aβ,9,10,11,12,12aβ,13,13aα-decahydro-8H-isoquino[2,1-g][1,6]naphthyridine; and
(±)-3-n-hexyl-5,6,8aα,9,10,11,12,12aα,13,13aα-decahydro-8H-isoquino[2,1-g][1,6]naphthyridine;
(±)-1-methoxy-5,6,8aβ,9,10,11,12,12aβ,13,13aα-decahydro-8H-isoquino[2,1-g][1,6]naphthyridine; and
(±)-1-methoxy-5,6,8aα,9,10,11,12,12aα,13,13aα-decahydro-8H-isoquino[2,1-g][1,6]naphthyridine;
(±)-2-methoxy-5,6,8aβ,9,10,11,12,12aα,13,13aα-decahydro-8H-isoquino[2,1-g][1,6]naphthyridine; and
(±) 2-methoxy-5,6,8aα,9,10,11,12,12aα,13,13aα-decahydro-8H-isoquino[2,1-g][1,6]naphthyridine;
(±)-4-methoxy-5,6,8aα,9,10,11,12,12aα,13,13aα-decahydro-8H-isoquino[2,1-g][1,6]naphthyridine; and
(±)-4-methoxy-5,6,8aα,9,10,11,12,12aα,13,13aα-decahydro-8H-isoquino[2,1-g][1,6]naphthyridine;
(±)-3-ethoxy-5,6,8aβ,9,10,11,12,12aβ,13,13aα-decahydro-8H-isoquino[2,1-g][1,6]naphthyridine; and
(±)-3-ethoxy-5,6,8aα,9,10,11,12,12aα,13,13aα-decahydro-8H-isoquino[2,1-g][1,6]naphthyridine;
(±)-3 isobutoxy-5,6,8aβ,9,10,11,12,12aβ,13,13aα-decahydro-8H-isoquino[2,1-g][1,6]naphthyridine; and (±)-3-isobutoxy-5,6,8aα,9,10,11,12,12aα,13,13aα-decahydro-8H-isoquino[2,1-g][1,6]naphthyridine;

(±)-3 n-hexyloxy-5,6,8aβ,9,10,11,12,12aα,13,13aα-decahydro-8H-isoquino[2,1-g][1,6]naphthyridine; and (±)-3-n-hexyloxy-5,6,8aα,9,10,11,12,12aα,13,13aα-decahydro-8H-isoquino[2,1-g][1,6]naphthyridine;

(±)-3-hydroxy-5,6,8aβ,9,10,11,12,12aβ,13,13aα-decahydro-8H-isoquino[2,1-g][1,6]naphthyridine; and (±)-3-hydroxy 5,6,8aα,9,10,11,12,12aα,13,13aα-decahydro-8H-isoquino[2,1-g][1,6]naphthyridine;

(±)-2,3-dihydroxy-5,6,8aβ,9,10,11,12,12aβ,13,13aα-decahydro-8H-isoquino[2,1-g][1,6]naphthyridine; and (±) 2,3-dihydroxy-5,6,8aα,9,10,11,12,12aα,13,13aα-decahydro-8H-isoquino[2,1-g][1,6]naphthyridine;

(±)-1,2-dimethoxy-5,6,8aβ,9,10,11,12,12aβ,13,13aα-decahydro-8H-isoquino[2,1-g][1,6]naphthyridine; and (±)-1,2-dimethoxy-5,6,8aα,9,10,11,12,12aα,13,13aα-decahydro-8H-isoquino[2,1-g][1,6]naphthyridine;

(±)-1,4 dimethoxy-5,6,8aβ,9,10,11,12,12aβ,13,13aα-decahydro- 8H-isoquino[2,1-g][1,6]naphthyridine; and (±)-1,4-dimethoxy-5,6,8aα,9,10,11,12,12aα,13,13aα-decahydro-8H-isoquino[2,1-g][1,6]naphthyridine;

(±)-3,4-dimethoxy-5,6,8aβ,9,10,11,12,12aα,13,13aα-decahydro-8H-isoquino[2,1-g][1,6]naphthyridine; and (±) 3,4-dimethoxy-5,6,8aα,9,10,11,12,12aα,13,13aα-decahydro-8H-isoquino[2,1-g][1,6]naphthyridine;

(±)-2,3-diethoxy-5,6,8aβ,9,10,11,12,12aβ,13,13aα-decahydro-8H-isoquino[2,1-g][1,6]naphthyridine; and (±)-2,3-diethoxy-5,6,8aα,9,10,11,12,12aα,13,13aα-decahydro-8H-isoquino[2,1-g][1,6]naphthyridine;

(±)-2,3-di-n-butoxy-5,6,8aβ,9,10,11,12,12aβ,13,13aα-decahydro-8H-isoquino[2,1-g][1,6]naphthyridine; and (±)-2,3-di-n-butoxy-5,6,8aα,9,10,11,12,12aα,13,13aα-decahydro-8H-isoquino[2,1-g][1,6]naphthyridine;

(±)-1,2-methylenedioxy-5,6,8aβ,9,10,11,12,12aβ,13,13aα-decahydro-8H-isoquino[2,1-g][1,6]naphthyridine; and (±)-1,2-methylenedioxy-5,6,8aα,9,10,11,12,12aα,13,13aα-decahydro-8H-isoquino[2,1-g][1,6]naphthyridine;

(±)-2-chloro-5,6,8aβ,9,10,11,12,12aβ,13,13aα-decahydro-8H-isoquino[2,1-g][1,6]naphthyridine; and (±)-2-chloro-5,6,8aα,9,10,11,12,12aα,13,13aα-decahydro-8H-isoquino[2,1-g][1,6]naphthyridine;

(±)-3-chloro-5,6,8aβ,9,10,11,12,12aβ,13,13aα-decahydro-8H-isoquino[2,1-g][1,6]naphthyridine; and (±)-3-chloro-5,6,8aα,9,10,11,12,12aα,13,13aα-decahydro-8H-isoquino[2,1-g][1,6]naphthyridine;

(±)-4-chloro-5,6,8aβ,9,10,11,12,12aβ,13,13aα-decahydro-8H-isoquino[2,1-g][1,6]naphthyridine; and (±)-4-chloro-5,6,8aβ,9,10,11,12,12aα,13,13aα-decahydro-8H-isoquino[2,1-g][1,6]naphthyridine;

(±)-3-bromo-5,6,8aβ,9,10,11,12,12aβ,13,13aα-decahydro-8H-isoquino[2,1-g][1,6]naphthyridine; and (±)-3-bromo-5,6,8aα,9,10,11,12,12aα,13,13aα-decahydro- 8H-isoquino[2,1-g][1,6]naphthyridine;

(±)-3-fluoro-5,6,8aβ,9,10,11,12,12aβ,13,13aα-decahydro-8H-isoquino[2,1-g][1,6]naphthyridine; and (±)-3-fluoro-5,6,8aα,9,10,11,12,12aα,13,13aαdecahydro-8H-isoquino[2,1-g][1,6]naphthyridine;

(±)-2-fluoro-5,6,8aβ,9,10,11,12,12aβ,13,13aα-decahydro-8H-isoquino[2,1-g][1,6]naphthyridine; and (±)-2-fluoro-5,6,8aα,9,10,11,12,12aα,13,13aα-decahydro-8H-isoquino[2,1-g][1,6]naphthyridine;

PREPARATION 4

Preparation of (8aS,12aS,13aS)-3-methoxy-120[(R)-(+)-1-phenylethylamino]carbonyl-5,6,8a,9,10,11,12,12a,13,13a-decahydroisoquino[2,1-g][1,6]naphthyridin-8-one (IX) and (8aR,12aR,13aR)-3-methoxy-12-[(R)-(+)-1-phenylethyl-amino]carbonyl-5,6,8a,9,10,11,12,12a,13,13a-decahydroisoquino]2,1-g][1,6]naphthyridin-8-one (X) and Related Compounds of Formula (IX) and (X)

A. A solution of 1.95 g of (±)-3-methoxy-5,6,8aα,9,10,11,12,12aα,13,13aα-decahydroisoquino-[2,1-g][1,6]naphthyridin-8-one, a compound of formula (V), and 1.0 g of (R)-(+)-α-methylbenzyl isocyanate in 50 ml of methylene chloride was stirred at room temperature for 30 minutes. Solvent was then removed under reduced pressure, and the residue chromatographed on silica gel, using multiple medium pressure chromatography and eluting with 5% methanol in ethyl acetate. The first compound eluted was (8aS,12aS,13aS)-3-methoxy-12-[(R)-(+)-1-phenylthylamino]carbonyl-5,6,8a,9,10,11,12,12a,13,13a-decahydroisoquino[2,1-g[1,6]-naphthyridin-8-one, mp 198°-199° C., $[\alpha]_D^{25} = +36.5$ (CHCl$_3$) followed by (8aR,12aR,13aR)-3-methoxy-12-[(R)-(+)-1-phenylethylamino]carbonyl-5,6,8a,9,10,11,12,12a,13,13a-decahydroisoquino-[2,1-g][1,6]naphthyridin-8-one, mp 220°-221° C., $[\alpha]_D^{25} = -11.4$ (CHCl$_3$).

B. Similarly, replacing (±)-3-methoxy-5,6,8aα,9,10,11,12,12aα,13,13aα-decahydroisoquino[2,1-g][1,6]-naphthyridin-8-one with the appropriate compound of formula (V) and following the procedure in paragraph A above, the following compounds of formula (IX) and (X) were prepared:
(8aS,12aS,13aS)-12-[(R)-(+)-1-phenylethylamino]carbonyl-5,6,8a,9,10,11,12,12a,13,13a-decahydroisoquino-[2,1-g][1,6]naphthyridin-8-one; and
(8aR,12aR,13aR)-12-[(R)-(+)-1-phenylethylamino]carbonyl-5,6,8a,9,10,11,12,12a,13,13a-decahydroisoquino[2 2,1-g][1,6]naphthyridin-8-one;
(8aS,12aS,13aS)-2,3-methylenedioxy-12-[(R)-(+)-1-phenylethylamino]carbonyl-5,6,8a,9,10,11,12,12a,13,-13a-decahydroisoquino[2,1-g][1,6]naphthyridin-8-one; and
(8aR,12aR,13aR)-2,3-methylenedioxy-12-[(R) (+)-1-phenylethylamino]carbonyl-5,6,8a,9,10,11,12,12a,-13,13a-decahydroisoquino[2,1-g][1,6]naphthyridin-8-one;

C. Similarly, replacing (±)-3-methoxy-5,6,8aα,9,10,11,12,12aα,13,13aα-decahydroisoquino[2,1-g][1,6]-naphthyridin-8-one with the appropriate compound of formula (V) and following the procedure in paragraph A above, the following compounds of formula (IX) and (X) are prepared:
(8aS,12aS,13aS)-2,3-dimethoxy-12-[(R)-(+)-1-phenylethylamino]carbonyl-5,6,8a,9,10,11,12,12a,13,13a-decahydroisoquino[2,1g][1,6]-naphthyridin-8-one; and
(8aR,12aR,13aR)-2,3-dimethoxy-12-[(R)-(+)-1-phenylethylamino]carbonyl-5,6,8a,9,10,11,12,12a,13,-

13a-decahydroisoquino[2,1 g][1,6]-naphthyridin-8-one;

(8aS,12aS,13aS)-1,4-dimethoxy-12-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aR)-1,4-dimethoxy-12-[(R)-(+)-1-phenylethylamino]carbonyl-5,6,8a,9,10,11,12,12a,13,-13a-decahydroisoquino[2,1-g][1,6]-naphthyridin-8-one;

(8aS,12aS,13aS)-2,3-(ethylene-1,2-dioxy)-12-[(R)-(+)-1-phenylethylamino]carbonyl-5,6,8a,9,10,11,12,-12a,13,13a-decahydroisoquino[2,1-g][1,6]-naphthyridin-8-one; and (8aR,12aR,13aR)-2,3-(ethylene-1,2-dioxy)-12-[(R)-(+)-1-phenylethylamino]carbonyl-5,6,8a,9,10,11,12,-12a,13,13a-decahydroisoquino[2,1-g][1,6]-naphthyridin-8-one;

(8aS,12aS,13aS)-1-methyl-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aR)-1-methyl-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aS)-2-methyl-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aR)-2-methyl-[(R)-(+)-1-phenylethylamino]carbonyl-5,6,8a,9,10,11,12,12a,13,13a-decahydroisoquino[2,1-g][1,6-naphthyridin-8-one;

(8aS,12aS,13aS)-3-methyl-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aR)-3-methyl-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aS)-2,3-dimethyl-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR)-2,3-dimethyl-[(R)-(+)-1-phenylethylamino]carbonyl-5,6,8a,9,10,11,12,12a,13,13a-decahydroisoquino[ 2,1-g][1,6]naphthyridin-8-one;

(8aS,12aS,13aS)-3-ethyl-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aR)-3-ethyl-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aS)-3-isobutyl-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR) 3-isobutyl-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aS)-3-n-hexyl-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aR)-3-n-hexyl-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aS)-1-methoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR)-1-methoxy-[(R)-(+)-1-phenylethylamino]carbonyl-5,6,8a,9,10,11,12,12a,13,13a decahydroisoquino[2,1-g][1,6]naphthyridin-8-one;

(8aS,12aS,13aS)-2-methoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR)-2-methoxy-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aS)-4-methoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR)-4-methoxy [(R)-(+)-1-phenylethylamino]carbonyl- 5,6,8a,9,10,11,12,12a,13,13a-decahydroisoquino[2,1-g][1,6]naphthyridin-8-one;

(8aS,12aS,13aS)-3-methoxy-2-methyl-[(R)-(+)-1-phenylethylamine]carbonyl-5,6,8a,9,10,11,12,12a,-13,13a-decahydroisoquino[2,1-g][1,6]naphthyridin-8-one; and (8aR,12aR,13aR)-3-methoxy-2-methyl-[(R)-(+)-1-phenylethylamine]carbonyl-5,6,8a,9,10,11,12,12a,-13,13a-decahydroisoquino[2,1-g][1,6]naphthyridin-8-one;

(8aS,12aS,13aS)-3-ethoxy-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aR)-3-ethoxy-[(R)-(+)-1-phenylethylamino]carbonyl-5,6,8a,9,10,11,12,12a,13,13a-decahydroisoquino[2,1-g][1,6]-naphthyridin 8-one;

(8aS,12aS,13aS)-3-isopropoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR)-3-isopropoxy-[(R)-(+)-1-phenylethylamino]carbonyl-5,6,8a,9,10,11,12,12a,13,13a-decahydroisoquino[2,1-g][1,6]naphthyridin-8 one;

(8aS,12aS,13aS)-3-isobutoxy-[(R)-(+)-1-phenylethylamino]carbonyl-5,6,8a,9,10,11,12,12a,13, 13a-decahydroisoquino[2,1-g][1,6]naphthyridin-8 one; and (8aR,12aR,13aR)-3-isobutoxy-[(R)-(+)-1-phenylethylamino]carbonyl-5,6,8a,9,10,11,12,12a,13, 13a-decahydroisoquino[2,1-g][1,6]naphthyridin 8-one:

(8aS,12aS,13aS)-3-n-hexyloxy-[(R)-(+)-1-phenylethylamino]carbonyl-5,6,8a,9,10,11,12,12a,13,13a-decahydroisoquino[2,1-g][1,6]naphthyridin-8 one; and (8aR,12aR,13aR)-3-n-hexyloxy-[(R)-(+)-1-phenylethyldecahydroisoquino[2,1-g][1,6]naphthyridin-8 one;

(8aS,12aS,13aS)-3-hydroxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR)-3-hydroxy-[(R)-(+)-1-ethylamino]carbonyl-5,6,8a,9,10,11,12,12a,13,13a-decahydroisoquino[2,1-g][1,6]naphthyridin-8-one;

(8aS,12aS,13aS)-2,3-dihydroxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR)-2,3-dihydroxy-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aS)-1,2-dimethoxy-[(R)-(+)-1-phenylethylamino]carbonyl-5,6,8a,9,10,11,12,12a,13,13a-decahydroisoquino[2,1-g][1,6]naphthyridin 8-one; and (8aR,12aR,13aR)-1,2-dimethoxy-[(R)-(+)-1-phenylethylamino]carbonyl-5,6,8a,9,10,11,12,12a,13,13a-decahydroisoquino[2,1-g][1,6]naphthyridin 8-one;

(8aS,12aS,13aS)-1,4-dimethoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR)-1,4-dimethoxy-[(R)-(+)-1-phenylethylamino]carbonyl-5,6,8a,9,10,11,12,12a,13,13a-decahydroisoquino[2,1-g][1,6]naphthyridin 8-one;

(8aS,12aS,13aS)-3,4-dimethoxy-[(R)-(+)-1-phenylethylamino]carbonyl-5,6,8a,9,10,11,12,12a,13,13a-decahydroisoquino[2,1-g][1,6]naphthyridin 8-one, and (8aR,12aR,13aR)-3,4-dimethoxy-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aS)-2,3-diethoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR)-2,3-diethoxy-[(R)-(+)-1-phenylethylamino]carbonyl-5,6,8a,9,10,11,12,12a,13,13a-decahydroisoquino[2,1-g][1,6]naphthyridin-8-one, (8aS,12aS,13aS)-2,3-di-n-butoxy-[(R)-(+)-1-phenylethylamino]carbonyl-5,6,8a,9,10,11,12,12a,13,13a-decahydroisoquino[ 2,1-g][1,6]naphthyridin-8-one; and

*8aR,12aR,13aR)-2,3-di-n-butoxy-[(R)-(+)-1-phenylethylamino]carbonyl-5,6,8a,9,10,11,12,12a,13,13a-decahydroisoquino[2,1-g][1,6]naphthyridin 8-one;

(8aS,12aS,13aS)-1,2-methylenedioxy-[(R)-(+)-1-phenylethylamine]carbonyl-5,6,8a,9,10,11,12,12a,13,-13a-decahydroisoquino[2,1-g][1,6]naphthyridin-8-one; and (8aR,12aR,13aR)-1,2-methylenedioxy-[(R)-(+)-1-phenylethylamine]carbonyl 5,6,8a,9,10,11,12,12a,13,-13a-decahydroisoquino[2,1-g][1,6]naphthyridin 8-one;

(8aS,12aS,13aS) 2-chloro-[(R)-(+)-1-phenylethylamino]carbonyl-5,6,8a,9,10,11,12,12a,13,13a-decahydroisoquino[2,1-g][1,6]naphthyridin-8-one; and (8aR.12aR,13aR)-2-chloro-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aS)-3-chloro-[(R)-(+)-1-phenylethylamino]carbonyl-5,6,8a,9,10,11,12,12a,13,13a-decahydroisoquino[2,1-g][1,6]naphthyridin 8-one; and (8aR,12aR,13aR)-3-chloro-[(R)-(+)-1-phenylethylamino]carbonyl-5,6,8a,9,10,11,12,12a,13,13a-decahydroisoquino[2,1-g][1,6]naphthyridin 8-one;

(8aS,12aS,13aS)-4-chloro-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aR)-4-chloro-[(R)-(+)-1-phenylethylamino]carbonyl-5,6,8a,9,10,11,12,12a,13,13a-decahydroisoquino[2,1-g][1,6]naphthyridin 8-one;

(8aS,12aS,13aS) 3-bromo-[(R)-(+)-1-phenylethylamino]carbonyl-5,6,8a,9,10,11,12,12a,13,13a-decahydroisoquino[2,1g][1,6]-naphthyridin-8-one; and (8aR,12aR,13aR)-3-bromo-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aS)-3-fluoro-[(R)-(+)-1-phenylethylamino]carbonyl- 5,6,8a,9,10,11,12,12a,13,13a-decahydroisoquino[2,1-g][1,6]naphthyridin-8-one; and (8aR,12aR,13aR)-3-fluoro-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aS)-2-fluoro-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aR)-2-fluoro-[(R)-(+)-1-phenylethylamino]carbonyl-5,6,8a,9,10,11,12,12a,13,13a-decahydroisoquino[2,1-g][1,6]-naphthyridin-8-one.

D. Similarly, replacing (±)-3-methoxy-5,6,8aα,9,10,11,12,12aα,13,13aα-decahydroisoquino[2,1-g][1,6]-naphthyridin-8-one with the appropriate compound of formula (VI) and following the procedure in paragraph A above, the following compounds are prepared:

(8aS,12aS,13aR)-3-methoxy-12-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aS)-3-methoxy-12-[(R)-(+)-1-phenylethyamino]carbonyl-5,6,8a,9,10,11,12,12a,13,13a-decahydroisoquino[2,1-g][1,6]naphthyridin-8-one;

(8aS,12aS,13aR)-12-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aS)-12-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aR)-2,3-methylenedioxy-12-[(R)-(+)-1-phenylethylamine]carbonyl 5,6,8a,9,10,11,12,12a,13,-13a-decahydroisoquino[2,1-g][1,6]naphthyridin 8-one; and (8aR,12aR,13aS)-2,3-methylenedioxy-12-[(R)-(+)-1-phenylethylamine]carbonyl-5,6,8a,9,10,11,12,12a,13,-13a-decahydroisoquino[2,1-g][1,6]naphthyridin 8-one;

(8aS,12aS,13aR) 2,3 dimethoxy-12-[(R)-(+) 1-phenylethylamino]carbonyl- 5,6,8a,9,10,11,12,12a,13,13a-decahydroisoquino[2,1-g][1,6]naphthyridin-8-one; and (8aR,12aR,13aS)-2,3-dimethoxy-12-[(R)-(+)-1-phenylethylamino]carbonyl-5,6,8a,9,10,11,12,12a,13,-13a-decahydroisoquino[2,1-g][1,6]naphthyridin 8-one;

(8aS,12aS,13aR)-1,4-dimethoxy12-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aS)-1,4-dimethoxy-12-[(R)-(+)-1-phenylethylamino]carbonyl-5,6,8a,9,10,11,12,12a,13,-13a-decahydroisoquino[2,1-g][1,6]naphthyridin-8-one;

(8aS,12aS,13aR)-2,3-(ethylene-1,2-dioxy)-12-[(R)-(+)-phenylethylamino]carbonyl-5,6,8a,9,10,11,12,12a,13,-13a-decahydroisoquino[2,1-g][1,6]naphthyridin-8-one; and (8aR,12aR,13aS)-2,3-(ethylene-1,2-dioxy)-12-[(R)-(+)phenylethylamino]carbonyl-5,6,8a,9,10,11,12,-12a,13,13a-decahydroisoquino[2,1-g][1,6]naphthyridin-8-one;

(8aS,12aS,13aR)-1-methyl-[(R)-(+)-1-phenylethylamino]carbonyl-5,6,8a,9,10,11,12,12a,13,13a-decahydroisoquino[2,1-g][1,6]-naphthyridin 8-one; and (8aR,12aR,13aS)-1-methyl-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aR)-2-methyl-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aS)-2-methyl-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aR)-3-methyl-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aS)-3-methyl-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aR)-2,3-dimethyl-(1-R-phenethylaminocarbonyl)-5,6,8a,9,10,11,12,12a,13,13a-decahydroisoquino[2,1-g][1,6]naphthyridin-8-one; and (8aR,12aR,13aS)-2,3-dimethyl-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aR)-3-ethyl [(R)-(+) 1-phenylethylamino]carbonyl-5,6,8a,9,10,11,12,12a,13,13a-decahydroisoquino[2,1-g][1,6]naphthyridin-8-one; and (8aR,12aR,13aS)-3-ethyl-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aR)-3-isobutyl-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aS)-3-isobutyl-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aR)-3-n-hexyl-[(R)-(+)-1-phenylethylamino]carbonyl-5,6,8a,9,10,11,12,12a,13,13a-decahydroisoquino[2,1-g][1,6]naphthyridin 8-one; and (812aR,13aS)-3-n-hexyl-[(R)-(+)-1-phenylethylamino]carbonyl 5,6,8a,9,10,11,12,12a,13,13a-decahydroisoquino[2,1-g][1,6]naphthyridin-8-one;

(8aS,12aS,13aR)-1-methoxy [(R)-(+)-1-phenylethylamino]carbonyl-5,6,8a,9,10,11,12,12a,13,13a-decahydroisoquino[2,1-g][1,6]naphthyridin-8-one; and (8aR,12aR,13aS)-1-methoxy-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aR) 2 methoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aS)-2-methoxy-[(R)-(+)-1-phenylethylamino]carbonyl-5,6,8a,9,10,11,12,12a,13,13a-decahydroisoquino[ 2,1-g][1,6]naphthyridin-8-one;

(8aS,12aS,13aR)-4-methoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aS)-4-methoxy-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aR)-3-methoxy 2-methyl-[(R)-(+) 1-phenylethylamine]carbonyl-5,6,8a,9,10,11,12,12a,13,-13a-decahydroisoquino[2,1-g][1,6]naphthyridin-8-one; and (8aR,12aR,13aS)-3-methoxy 2-methyl-[(R)-(+)-1-phenylethylamine]carbonyl-5,6,8a,9,10,11,12,12a,13,13a-decahydroisoquino[2,1-g][1,6]naphthyridin-8-one;

(8aS,12aS,13aR)-3 ethoxy-[(R)-(+)-1-phenylethylamino]carbonyl-5,6,8a,9,10,11,12,12a,13,13a-decahydroisoquino[2,1-g][1,6]-naphthyridin-8-one; and (8aR,12aR,13aS)-3-ethoxy-[(R)-(+)-1-phenylethylamino]carbonyl-5,6,8a,9,10,11,12,12a,13,13a-decahydroisoquino[2,1-g][1,6]-naphthyridin-8-one;

(8aS,12aS,13aR)-3-isopropoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aS)-3-isopropoxy-[(R)-(+)-1-phenylethylamino]carbonyl-5,6,8a,9,10,11,12,12a,13,13a-decahydroisoquino[2,1-g][1,6]naphthyridin 8-one;

(8aS,12aS,13aR)-3-isobutoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aS)-3-isobutoxy-[(R)-(+)-1-phenylethylamino]carbonyl-5,6,8a,9,10,11,12,12a,13,13a-decahydroisoquino[2,1-g][1,6]naphthyridin 8-one;

(8aS,12aS,13aR)-3-n-hexyloxy-[(R)-(+)-1-phenylethylamino]carbonyl-5,6,8a,9,10,11,12,12a,13,13a-decahydroisoquino[2,1-g][1,6]naphthyridin 8-one: and (8aR,12aR,13aS)-3 n-hexyloxy-[(R)-(+)-1-phenylethylamino]carbonyl- 5,6,8a,9,10,11,12,12a,13,13a-decahydroisoquino[2,1-g][1,6]naphthyridin-8-one;

(8aS,12aS,13aR)-3-hydroxy-[(R)-(+)-1-phenylethylamino]carbonyl-5,6,8a,9,10,11,12,12a,13,13a-decahydroisoquino[2,1-g][1,6]naphthyridin 8-one; and (8aR,12aR,13aS)-3-hydroxy-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aR)-2,3-dihydroxy-[(R)-(+)-1-phenylethylamino]carbonyl-5,6,8a,9,10,11,12,12a,13,13a-decahydroisoquino[2,1-g][1,6]naphthyridin 8-one; and (8aR,12aR,13aS)-Z,3-dihydroxy-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aR)-1,2-dimethoxy-[(R)-(+)-1-phenylethylamino]carbonyl-5,6,8a,9,10,11,12,12a,13,13a-decahydroisoquino[2,1-g][1,6]naphthyridin-8-one; and (8aR,12aR,13aS)-1,2-dimethoxy-[(R)-(+)-1-phenylethylamino]carbonyl-5,6,8a,9,10,11,12,12a,13,13a-decahydroisoquino[2,1-g][1,6]naphthyridin-8-one;

(8aS,12aS,13aR)-1,4-dimethoxy-[(R)-(+)-1-phenylethylamino]carbonyl-5,6,8a,9,10,11,12,12a,13,13a-decahydroisoquino[2,1-g][1,6]naphthyridin 8-one; and (8aR,12aR,13aS)-1,4-dimethoxy-[(R)-(+)-1-phenyle-
thylamino]carbonyl-5,6,8a,9,10,11,12,12a,13,13a-
decahydroisoquino[2,1-g][1,6]naphthyridin-8-one;
(8aS,12aS,13aR)-3,4-dimethoxy-[(R)-(+)-1-phenyle-
thylamino]carbonyl-5,6,8a,9,10,11,12,12a,13,13a-
decahydroisoquino[2,1-g][1,6]naphthyridin-8-one;
and
(8aR,12aR,13aS)-3,4-dimethoxy-[(R)-(+)-1-phenyle-
thylamino]carbonyl-5,6,8a,9,10,11,12,12a,13,13a-
decahydroisoquino[2,1-g][1,6]naphthyridin-8-one;
(8aS,12aS,13aR)-2,3-diethoxy-[(R)-(+)-1-phenyle-
thylamino]carbonyl-5,6,8a,9,10,11,12,12a,13,13a-
decahydroisoquino[2,1-g][1,6]naphthyridin 8-one,
and
(8aR,12aR,13aS)-2,3-diethoxy-((R)-(+)-phenyle-
thylamino]carbonyl-5,6,8a,9,10,11,12,12a,13,13a-
decahydroisoquino[2,1-g][1,6]naphthyridin-8-one;
(8aS,12aS,13aR)-2,3-di-n-butoxy-[(R)-(+)-1-phenyle-
thylamino]carbonyl-5,6,8a,9,10,11,12,12a,13,13a-
decahydroisoquino[2,1-g][1,6]naphthyridin-8-one;
and
(8aR,12aR,13aS)-2,3 di-n-butoxy-[(R)-(+)-1-phenyle-
thylamino]carbonyl-5,6,8a,9,10,11,12,12a,13,13a-
decahydroisoquino[2,1-g][1,6]naphthyridin-8-one;
(8aS,12aS,13aR)-1,2-methylenedioxy-[(R)-(+)-1-
phenylethylamine]carbonyl-5,6,8a,9,10,11,12,12a,13,-
13a-decahydroisoquino[2,1-g][1,6]naphthyridin-
8-one; and
(8aR,12aR,13aS)-1,2-methylenedioxy-[(R)-(+)-1-
phenylethylamine]carbonyl-5,6,8a,9,10,11,12,12a,13,-
13a-decahydroisoquino[2,1-g][1,6]naphthyridin-
8-one;
(8aS,12aS,13aR)-2-chloro-[(R)-(+)-1-phenyle-
thylamino]carbonyl-5,6,8a,9,10,11,12,12a,13,13a-
decahydroisoquino[2,1-g][1,6]-naphthyridin-8-one;
and
(8aR,12aR,13aS)-2-chloro-[(R)-(+)-1-phenyle-
thylamino]carbonyl-5,6,8a,9,10,11,12,12a,13,13a-
decahydroisoquino[2,1-g][1,6]naphthyridin-8-one;
(8aS,12aS,13aR)-3-chloro-[(R)-(+)-1-phenyle-
thylamino]carbonyl-5,6,8a,9,10,11,12,12a,13,13a
decahydroisoquino[2,1-g][1,6]-naphthyridin-8-one;
and
(8aR,12aR,13aS)-3-chloro [(R)-(+)-1-phenyle-
thylamino]carbonyl-5,6,8a,9,10,11,12,12a,13,13a-
decahydroisoquino[2,1-g][1,6]naphthyridin-8-one;
(8aS,12aS,13aR)-4-chloro-[(R)-(+)-1-phenyle-
thylamino]carbonyl-5,6,8a,9,10,11,12,12a,13,13a-
decahydroisoquino[2,1-g][1,6]-naphthyridin-8-one;
and
(8aR,12aR,13aS)-4-chloro-[(R)-(+)-1-phenyle-
thylamino]carbonyl-5,6,8a,9,10,11,12,12a,13,13a-
decahydroisoquino[2,1-g][1,6]-naphthyridin-8-one;
(8aS,12aS,13aR)-3-bromo-[(R)-(+)-1-phenyle-
thylamino]carbonyl-5,6,8a,9,10,11,12,12a,13,13a-
decahydroisoquino-[ 2,1-g][1,6]-naphthyridin-8-one;
and
(8aR,12aR,13aS) 3-bromo [(R)-(+)-1-phenyle-
thylamino]carbonyl-5,6,8a,9,10,11,12,12a,13,13a
-decahydroisoquino[2,1-g][1,6]-naphthyridin-8-one;
(8aS,12aS,13aR)-3-fluoro-[(R)-(+)-1-phenyle-
thylamino]carbonyl-5,6,8a,9,10,11,12,12a,13,13a-
decahydroisoquino[2,1-g][1,6]-naphthyridin-8-one;
and
(8aR,12aR,13aS)-3-fluoro-[(R)-(+)-1-phenyle-
thylamino]carbonyl-5,6,8a,9,10,11,12,12a,13,13a-
decahydroisoquino[2,1-g][1,6]-naphthyridin 8-one;

(8aS,12aS,13aR)-2-fluoro-[(R)-(+)-1-phenyle-
thylamino]carbonyl-5,6,8a,9,10,11,12,12a,13,13a
-decahydroisoquino[2,1-g][1,6]-naphthyridin-8-one;
and
(8aR,12aR,13aS)-2-fluoro-[(R)-(+)-1-phenyle-
thylamino]carbonyl-5,6,8a,9,10,11,12,12a,13,13a-
decahydroisoquino[2,1-g][1,6]-naphthyridin-8-one.

PREPARATION 5

Preparation of
(8aS,12aS,13aS)-3-methoxy-12[(R)-(+)-phenyle-
thylamino]carbonyl-5,6,8a,9,10,11,12,12a,13,13a-
decahydro8H-isoquino[2,1-g][1,6]naphthyridine and
(8aS,12aR,13aR)-3-methoxy-12-[(R)-(+)-phenyle-
thylamino]carbonyl-5,6,8a,9,10,11,12,12a,13,13a-
decahydroisoquino-8H-quino[2,1-g][1,6]naphthyridine
and Related Compounds of Formula (XI) and (XII)

A. A solution of 11.5 g of (8aS,12aS,13aS)-3-
methoxy-12-[(R)-(+)-1-phenylethylamino]carbonyl-
5,6,8a,9,10,11,12,12a,13,13a -decahydroisoquino[2,1-
g][1,6]naphthyridin-8-one, in 50 ml of tetrahydrofuran
was added slowly to a solution of 2.0 g of lithium alumi-
num hydride in 75 ml of tetrahydrofuran. The resulting
mixture was stirred at reflux for 2 hours, cooled, and
treated sequentially with 2.5 ml of water, 2.5 ml of 15%
sodium hydroxide, and 7.5 ml of water. The mixture
was filtered and the filtrate was evaporated to afford 8.8
g of (8aR,12aS,13aS)-3-methoxy-12-[(R)-(+)-1-
phenylethylamino]-carbonyl-5,6,8a,9,10,11,12,12a,13,-
13a-decahydro-8-H-isoquino[2,1-g][1,6]naphthyridine,
a compound of formula (XI), as a foam. The foam was
used as such in the next reaction with no further purifi-
cation.

B. Similarly, replacing (8aS,12aS,13aS) 3-methoxy
12-[(R)-(+)-1-phenylethylamino]carbonyl-
5,6,8a,9,10,11,12,12a,13,13a-decahydroisoquino[2,1-
g][1,6]naphthyridin-8-one with other compounds of
formula (IX) or (X) and following the procedure in
paragraph A above, the following compounds of for-
mula (XI) and (XII) were prepared:
(8aS,12aR,13aR) 3-methoxy-12-[(R)-(+)-1-phenyle-
thylamino]carbonyl-5,6,8a,9,10,11,12,12a,13,13a
decahydro-8H-isoquino[2,1-g][1,6]naphthyridine;
(8aR,12aS,13aS)-12--
-[(R)-(+)-1-phenylethylamino]carbonyl-
5,6,8a,9,10,11,12,12a,13,13a-decahydro-8H-
isoquino[2,1-g][1,6]naphthyridine;
(8aS,12aR,13aR) 12-[(R)-(+)-1-phenylethylamino]car-
bonyl-5,6,8a,9,10,11,12,12a,13,13a decahydro-8H-
isoquino[2,1-g][1,6]naphthyridine;
(8aR,12aS,13aS) 2,3-methylenedioxy-12-[(R)-(+)-1-
phenylethylamine]carbonyl-5,6,8a,9,10,11,12,12a,13,-
13a-decahydro-8H-isoquino[2,1-g][1,6]naphthyri-
dine; and
(8aS,12aR,13aR)-2,3-methylenedioxy-12-[(R)-(+)-1-
phenylethylamine]carbonyl-5,6,8a,9,10,11,12,12a,13
13a-decahydro-8H-isoquino[2,1-g][1,6]naphthyri-
dine.

C. Similarly, replacing (8aS,12aS,13aS)-3-methoxy-
12-[(R)-(+)-1-phenylethylamino]-carbonyl-
5,6,8a,9,10,11,12,12a,13,13a-decahydroisoquino[2,1-
g][1,6]naphthyridin-8-one with other compounds of
formula (IX) or (X) and following the procedure in
paragraph A above, the following exemplary com-
pounds of formula (XI) and (XII) are prepared:

(8aR,12aS,13aS)-2,3-dimethoxy-12-[(R)-(+) 1 phenylethylamino]carbonyl-5,6,8a,9,10,11,12,12a,13,13a-decahydro-8H-isoquino[2,1-g][1,6]naphthyridine;

(8aS,12aR,13aR)-2,3-dimethoxy-12-[(R)-(+)-1-phenylethylamino]carbonyl-5,6,8a,9,10,11,12,12a,13,-13a-decahydro-8H-isoquino[2,1-g][1,6]naphthyridine;

(8aR,12aS,13aS)-1,4 dimethoxy-12-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-1,4-dimethoxy-12-[(R)-(+) 1-phenylethylamino]carbonyl-5,6,8a,9,10,11,12,12a,13,13a-decahydro-8H-isoquino[2,1-g][1,6]naphthyridine;

(8aR,12aS,13aS)-2,3-(ethylene-1,2-dioxy)-12-[(R)-(+)-1-phenylethylamino]carbonyl 5,6,8a,9,10,11,12,-12a,13,13a-decahydro-8H-isoquino[2,1-g][1,6]naphthyridine;

(8aS,12aR,13aR)-2,3-(ethylene-1,2-dioxy)-12-[(R)-(+)-phenylethylamino]carbonyl-5,6,8a,9,10,11,12,12a,13,-13a-decahydro-8H-isoquino[2,1-g][1,6]naphthyridine;

(8aR,12aS,13aS)-1-methyl-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-1-methyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-2-methyl-[(R)-(+) 1-phenylethylamino]carbonyl-5,6,8a,9,10,11,12,12a,13,13a-decahydro-8H-isoquino[2,1-g][1,6]naphthyridine;

(8aS,12aR,13aR)-2-methyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-3-methyl-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-3-methyl-[(R)-(+)-1-phenylethylamino]carbonyl-5,6,8a,9,10,11,12,12a,13,13a-decahydro-8H-isoquino[ 2,1-g][1,6]naphthyridine;

(8aR,12aS,13aS)-2,3-dimethyl-(R)-(+)-1-phenylethylamino]carbonyl-5,6,8a,9,10,11,12,12a,13,13a-decahydro-8H-isoquino[2,1-g][1,6]naphthyridine (8aS,12aR,13aR)-2,3-dimethyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-3-ethyl-[(R)-(+)-1-phenylethylamino]carbonyl-5,6,8a,9,10,11,12,12a,13,13a-decahydro-8H-isoquino[2,1-g][1'6]-naphthyridine;

(8aS,12aR,13aR)-3-ethyl-[(R)-(+)-1-phenylethylamino]carbonyl-5,6,8a,9,10,11,12,12a,13,13a-decahydro-8H-isoquino[2,1-g][1,6]-naphthyridine;

(8aR,12aS,13aS)-3-isobutyl-[(R)-(+)-1-phenylethylamino]carbonyl-5,6,8a,9,10,11,12,12a,13,-13a-decahydro-8H-isoquino[2,1-g][1,6]naphthyridine;

(8aS,12aR,13aR)-3-isobutyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-3-n-hexyl-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR) 3-n-hexyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-1-methoxy-[(R)-(+)-1-phenylethylamino]carbonyl-5,6,8a,9,10,11,12,12a,13,13a-decahydro 8H-isoquino-[2,1-g][1,6]naphthyridine;

(8aS,12aR,13aR)-1-methoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-2-methoxy-[(R)-(+)-1-phenylethylamino]carbonyl-5,6,8a,9,10,11,12,12a,13,13a decahydro-8H-isoquino[2,1-g][1,6]naphthyridine;

(8aS,12aR,13aR)-2-methoxy-[(R)-(+)-1-phenylethylamino]carbonyl- 5,6,8a,9,10,11,12,12a,13,13a-decahydro-8H-isoquino[2,1-g][1,6]naphthyridine;

(8aR,12aS,13aS)-4-methoxy-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-4-methoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-3-methoxy-2-methyl-[(R)-(+)-1-phenylethylamine]carbonyl-5,6,8a,9,10,11,12,12a,13,-13a-decahydro-8H-isoquino[2,1-g][1,6]naphthyridine;

(8aS,12aR,13aR)-3-methoxy-2-methyl-[(R)-(+)-1-phenylethylamine]carbonyl-5,6,8a,9,10,11,12,12a,13,-13a-decahydro-8H-isoquino[2,1-g][1,6]naphthyridine;

(8aR,12aS,13aS)-3-ethoxy-[(R)-(+)-1-phenylethylamino]carbonyl-5,6,8a,9,10,11,12,12a,13,13a decahydro-8H-isoquino[2,1-g][1,6]naphthyridine;

(8aS,12aR,13aR)-3-ethoxy-[(R)-(+)-1-phenylethylamino]carbonyl-5,6,8a,9,10,11,12,12a,13,13a-decahydro-8H-isoquino[2,1-g][1,6]naphthyridine;

(8aS,12aS,13aS)-3-isopropoxy-[(R)-(+)-1-phenylethylamino]carbonyl-5,6,8a,9,10,11,12,12a,13, 13a-decahydro-8H-isoquino[2,1-g][1,6]naphthyridine;

(8aS,12aR,13aR)-3-isopropoxy-[(R)-(+)-1-phenylethylamino]carbonyl-5,6,8a,9,10,11,12,12a13,13a-decahydro-8H-isoquino[2,1-g][1,6]naphthyridine;

(8aR,12aS,13aS)-3-isobutoxy-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-3-isobutoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-3-n-hexyloxy-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-3-n-hexyloxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-3-hydroxy-[(R)-(+)-1-phenylethylamino]carbonyl-5,6,8a,9 10,11,12,12a,13,13a-decahydro-8H-isoquino[2,1-g][1,6]naphthyridine;

(8aS,12aR,13aR)-3-hydroxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-2,3-dihydroxy-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR) 2,3-dihydroxy-[(R)-(+-1-phenylethylamino]carbonyl-5,6,8a,9,10,11,12,12a,13,13a-decahydro-8H-isoquino[2,1-g][1,6]naphthyridine;

(8aR,12aS,13aS)-1,2-dimethoxy-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-1,2-dimethoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-1,4-dimethoxy-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR) 1,4-dimethoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-3,4-dimethoxy-[(R)-(+)-1-phenylethylmino]carbonyl-5,6,8a,9,10,11,12,12a,13,13a-decahydro-8H-isoquino[2,1-g][1,6]naphthyridine;

(8aS,12aR,13aR)-3,4-dimethoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-2,3-diethoxy-[(R)-(+)-1-phenylethylamino]carbonyl-5,6,8a,9,10,11,12,12a,13,13a-decahydro-8H-isoquino[ 2,1-g][1,6]naphthyridine;

(8aS,12aR,13aR)-2,3-diethoxy ((R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-2,3-di-n-butoxy-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-2,3-di-n-butoxy-[(R)-(+)-1-phenylethylamino]carbonyl-5,6,8a,9,10,11,12,12a,13,13a decahydro-8H-isoquino[2,1-g][1,6]naphthyridine;

(8aR,12aS,13aS)-1,2-methylenedioxy-[(R)-(+)-1-phenylethylamine]carbonyl-5,6,8a,9,10,11,12,12a,13,-13a-decahydro-8H isoquino[2,1-g][1,6]naphthyridine;

(8aS,12aR,13aR) 1,2-methylenedioxy-[(R)-(+)-1-phenylethylamine]carbonyl-5,6,8a,9,10,11,12,12a,13,-13a-decahydro-8H-isoquino[2,1-g][1,6]naphthyridine;

(8aR,12aS,13aS)-2-chloro-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-2-chloro-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-3-chloro-[(R)-(+)-1-phenylethylamino]carbonyl-5,6,8a,9,10,11,12,12a,13,13a decahydro-8H-isoquino[2,1-g][1,6]naphthyridine;

(8aS,12aR,13aR)-3-chloro-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-4-chloro-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-4-chloro-[(R)-(+)-1-phenylethylamino]carbonyl 5,6,8a,9,10,11,12,12a,13,13a-decahydro-8H-isoquino[2,1-g][1,6]naphthyridine;

(8aR,12aS,13aS)-3-bromo-[(R)-(+)-1-phenylethylamino]- carbonyl-5,6,8a,9,10,11,12,12a,13,13a-decahydro-8H-isoquino[2,1-g][1,6]naphthyridine, (8aS,12aR,13aR)-3-bromo-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-3-fluoro-[(R)-(+)-1-phenylethylamino]carbonyl-5,6,8a,9,10,11,12,12a,13,13a-decahydro-8H-isoquino[2,1-g][1,6]naphthyridine;

(8aS,12aR,13aR)-3-fluoro-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aS)-2-fluoro-[(R)-(+)-1-phenylethylamino]carbonyl-5,6,8a,9,10,11,12,12a,13,13a-decahydro-8H-isoquino[2,1-g][1,6]naphthyridine; and (8aS,12aR,13aR)-2-fluoro-[(R)-(+)-1-phenylethylamino]carbonyl-5,6,8a,9,10,11,12,12a,13,13a-decahydro-8H-isoquino[2,1-g][1,6]naphthyridine.

D. Similarly, replacing (8aS,12aS,13aS)-3-methoxy-12-[(R)-(+)-1-phenylethylamino]carbonyl-5,6,8a,9,10,11,12,12a,13,13a-decahydroisoquino[2,1-g][1,6]naphthyridin-8-one with other similar compounds and following the procedure in paragraph A above, the following exemplary compounds are prepared:

(8aR,12aS,13aR)-3-methoxy-12-[(R)-(+)-1-phenylethylamino]carbonyl-5,6,8a,9,10,11,12,12a,13,13a-decahydro 8H-isoquino[2,1-g][1,6]naphthyridine;

(8aR,12aS,13aR)-12-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-2,3-methylenedioxy-12-[(R)-(+)-1-phenylethylamino]carbonyl-5,6,8a,9,10,11,12,12a,13,-13a-decahydro-8H-isoquino[2,1-g][1,6]naphthyridine;

(8aR,12aS,13aR)-2,3-dimethoxy-12-[(R)-(+)-1-phenylethylamino]carbonyl-5,6,8a,9,10,11,12,12a,13,-13a-decahydro-8H-isoquino[2,1-g][1,6]naphthyridine;

(8aR,12aS,13aR)-1,4-dimethoxy-12-[(R)-(+)-1-phenylethylamino]carbonyl-5,6,8a,9,10,11,12,12a,13,-13a-decahydro-8H-isoquino[2,1-g][1,6]naphthyridine;

(8aR,12aS,13aR)-2,3-(ethylene-1,2-dioxy)-12-[(R)-(+)-1-phenylethylamino]carbonyl-5,6,8a,9,10,11,12,-12a,13,13a-decahydro-8H-isoquino[2,1-g][1,6]naphthyridine;

(8aR,12aS,13aR)-1-methyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-2-methyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-methyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-2,3-dimethyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-ethyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-isobutyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-n-hexyl-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-1-methoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-2-methoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-4-methoxy-[(R)-(+)-1-phenylethylamino]carbonyl-5,6,8a,9,10,11,12,12a,13,13a-decahydro-8H-isoquino[ 2,1-g][1,6]naphthyridine;

(8aR,12aS,13aR)-3-methoxy-2-methyl-(1-R-phenethylaminocarbonyl)-5,6,8a,9,10,11,12,12a,13,13a-decahydro-8H-isoquino[2,1-g][1,6]naphthyridine;

(8aR,12aS,13aR)-3-ethoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-isopropoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-isobutoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-n-hexyloxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-hydroxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-2,3-dihydroxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-1,2-dimethoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-1,4-dimethoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3,4-dimethoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-2,3-diethoxy-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-2,3-di-n-butoxy-[(R)-(+)-1-phenylethylamino]carbonyl- 5,6,8a,9,10,11,12,12a,13,13a-decahydro-8H-isoquino[2,1-g][1,6]naphthyridine;

(8aR,12aS,13aR)-1,2-methylenedioxy-[(R)-(+)-1-phenylethylamine]carbonyl-5,6,8a,9,10,11,12,12a,13,13a-decahydro-8H-isoquino[2,1-g][1,6]naphthyridine;

(8aR,12aS,13aR)-2-chloro-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-chloro-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-4-chloro-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-bromo-[(R)-(+)-1-phenylethylamino]carbonyl-5,6,8a,9,10,11,12,12a,13,13a-decahydro-8H-isoquino[2,1-g][1,6]naphthyridine;

(8aR,12aS,13aR)-3-fluoro-[(R)-(+)-1-phenylethylamino]carbonyl-5,6,8a,9,10,11,12,12a,13,13a-decahydro-8H-isoquino[2,1-g][1,6]naphthyridine; and (8aR,12aS,13aR)-2-fluoro-[(R)-(+)-1-phenylethylamino]carbonyl-5,6,8a,9,10,11,12,12a,13,13a-decahydro-8H-isoquino[2,1-g][1,6]naphthyridine.

PREPARATION 6

Preparation of
(8aR,12aS,13aS)-3-methoxy-5,6,8a,9,10,11,12,12a,13,-13a-decahydro-8H-isoquino[2,1-g][1,6]naphthyridine
and
(8aS,12aR,13aR)-3-methoxy-5,6,8a,9,10,11,12,12a,13,-13a-decahydro-8H-isoquino[2,1-g][1,6]naphthyridine
and Related Compounds of Formula (VIIA) and (VIIB)

A. A solution of 10.5 g of (8aR,12aS,13aS)-3-methoxy-12-[(R)-(+)-1-phenylethylamino]carbonyl-5,6,8a,9,10,11,12,12a,13,13a-decahydro-8H-isoquino[2,1-g][1,6]naphthyridine in 125 ml of 2N sodium n-butoxide in n-butanol was refluxed for 4 hours. After cooling, water was added and the solution acidified with 2N hydrochloric acid. The solution was then extracted with ethyl acetate, the aqueous portion basified with aqueous ammonium hydroxide and extracted further with methylene chloride. Solvent was then removed from the extract under reduced pressure and the residue chromatographed on silica gel, eluting with 10–20% methanol in methylene chloride, to give (8aR,12aS,13aS)-3-methoxy-5,6,8a,9,10,11,12,12a,13,-13a-decahydro-8H-isoquino[2,1-g][1,6]naphthyridine, a compound of formula (VIIA), mp 125°–127° C., $[\alpha]_D^{25} = -150.7$ (CHCl$_3$)

B. Similarly, replacing (8aR,12aS,13aS)-3-methoxy-12-[(R)-(+)-1-phenylethylamino]carbonyl-5,6,8a,9,10,11,12,12a,13,13a-decahydro-8H-isoquino[2,1-g][1,6]naphthyridine with other compounds of formula (XI) or (XII) and following the procedure in paragraph A above, the following compounds of formula (VIIA) and (VIIB) were prepared:

(8aS,12aR,13aR)-3-methoxy-5,6,8a,9,10,11,12,-12a,13,13a-decahydro-8H-isoquino [2,1-g][1,6]naphthyridine, mp 125°–127° C., $[\alpha]_D^{25} = +154.5$ (CHCl$_3$).

(8aR,12aS,13aS)-5,6,8a,9,10,11,12,12a,13,13a-decahydro-8H-isoquino[2,1-g][1,6]naphthyridine;

(8aS,12aR,13aR)-5,6,8a,9,10,11,12,12a,13,13a-decahydro-8H-isoquino[2,1-g][1,6]naphthyridine;

(8aR,12aS,13aS)-2,3-methylenedioxy-5,6,8a,9,10,11,12,-12a,13,13a-decahydro-8H-isoquino[2,1-g][1,6]naphthyridine; and (8aS,12aR,13aR)-2,3-methylenedioxy-5,6,8a,9,10,11,12,-12a,13,13a-decahydro-8H-isoquino[2,1-g][1,6]naphthyridine.

C. Similarly, replacing (8aR,12aS,13aS)-3-methoxy-12-[(R)-(+)-1-phenylethylamino]-carbonyl-5,6,8a,9,10,11,12,12a,13,13a-decahydro-8H-isoquino[2,1-g][1,6]naphthyridine with other compounds of formula (XI) or (XII) and following the procedure in paragraph A above, the following exemplary compounds of formula (VIIA) and (VIIB) are prepared:

(8aR,12aS,13aS)-2,3-dimethoxy-5,6,8a,9,10,11,12,-12a,13,13a-decahydro-8H-isoquino[2,1-g][1,6]naphthyridine;

(8aS,12aR,13aR)-2,3-dimethoxy-5,6,8a,9,10,11,12,-12a,13,13a-decahydro-8H-isoquino[2,1-g][1,6]naphthyridine;

(8aR,12aS,13aS)-1,4-dimethoxy-5,6,8a,9,10,11,12,-12a,13,13a-decahydro-8H-isoquino[2,1-g][1,6]naphthyridine;

(8aS,12aR,13aR)-1,4-dimethoxy-5,6,8a,9,10,11,12,-12a,13,13a-decahydro-8H-isoquino[2,1-g][1,6]naphthyridine;

(8aR,12aS,13aS)-2,3 (ethylene-1,2-dioxy)-5,6,8a,9,10,11,12,12a,13,13a-decahydro-8H-isoquino[2,1-g][1,6]naphthyridine;

(8aS,12aR,13aR)-2,3 (ethylene 1,2-dioxy)-5,6,8a,9,10,11,12,12a,13,13a-decahydro-8H-isoquino[2,1-g][1,6]naphthyridine;

(8aR,12aS,13aS)-1-methyl-5,6,8a,9,10,11,12,12a,13,13a-decahydro- 8H-isoquino[2,1-g][1,6]-naphthyridine;

(8aS,12aR,13aR)-1-methyl-5,6,8a,9,10,11,12,12a,13,13a-decahydro-8H-isoquino[2,1-g][1,6]-naphthyridine;

(8aR,12aS,13aS)-2-methyl-5,6,8a,9,10,11,12,12a,13,13a-decahydro-8H-isoquino[2,1-g][1,6]-naphthyridine;

(8aS,12aR,13aR)-2-methyl-5,6,8a,9,10,11,12,12a,13,13a-decahydro-8H-isoquino[2,1-g][1,6]-naphthyridine;

(8aR,12aS,13aS)-3-methyl-5,6,8a,9,10,11,12,12a,13,13a-decahydro-8H-isoquino[2,1-g][1,6]-naphthyridine;

(8aS,12aR,13aR)-3-methyl-5,6,8a,9,10,11,12,12a,13,13a-decahydro-8H-isoquino[2,1-g][1,6]-naphthyridine;

(8aR,12aS,13aS)-2,3-dimethyl-5,6,8a,9,10,11,12,12a,13,-13a-decahydro-8H-isoquino[2,1-g][1,6]naphthyridine;

(8aS,12aR,13aR)-2,3-dimethyl-5,6,8a,9,10,11,12,12a,13,-13a-decahydro-8H-isoquino[2,1-g][1,6]naphthyridine;
(8aR,12aS,13aS)-3-ethyl-5,6,8a,9,10,11,12,12a,13,13a-decahydro-8H-isoquino [2,1-g][1,6]-naphthyridine;
(8aS,12aR,13aR)-3-ethyl-5,6,8a,9,10,11,12,12a,13,13a-decahydro-8H-isoquino[2,1-g][1,6]-naphthyridine;
(8aR,12aS,13aS)-3-isobutyl-5,6,8a,9,10,11,12,12a,13,-13a-decahydro-8H-isoquino[2,1-g][1,6]naphthyridine;
(8aS,12aR,13aR)-3-isobutyl-5,6,8a,9,10,11,12,12a,13,-13a-decahydro-8H-isoquino[2,1-g][1,6]naphthyridine;
(8aR,12aS,13aS)-3-n hexyl-5,6,8a,9,10,11,12,12a,13,13a-decahydro-8H-isoquino[2,1-g][1,6]naphthyridine;
(8aS,12aR,13aR)-3-n-hexyl-5,6,8a,9,10,11,12,12a,13,13a-decahydro-8H-isoquino[2,1-g][1,6]naphthyridine;
(8aR,12aS,13aS)-1-methoxy-5,6,8a,9,10,11,12,12a,13,-13a-decahydro-8H-isoquino[2,1-g][1,6]naphthyridine;
(8aS,12aR,13aR)-1-methoxy-5,6,8a,9,10,11,12,12a,13,-13a-decahydro-8H-isoquino[2,1-g][1,6]naphthyridine;
(8aR,12aS,13aS)-2-methoxy-5,6,8a,9,10,11,12,12a,13,-13a-decahydro-8H-isoquino[2,1-g][1,6]naphthyridine;
(8aS,12aR,13aR)-2-methoxy-5,6,8a,9,10,11,12,12a,13,-13a-decahydro-8H-isoquino[2,1-g][1,6]naphthyridine;
(8aR,12aS,13aS)-4-methoxy-5,6,8a,9,10,11,12,12a,13,a-decahydro-8H-isoquino[2,1-g][1,6]naphthyridine;
(8aS,12aR,13aR)-4-methoxy-5,6,8a,9,10,11,12,12a,13,a-decahydro-8H-isoquino[2,1-g][1,6]naphthyridine;
(8aR,12aS,13aS)-3-methoxy-2-methyl-5,6,8a,9,10,11,12,12a,13,13a-decahydro-8H-isoquino[2,1-g][1,6]naphthyridine;
(8aS,12aR,13aR)-3-methoxy-2-methyl-5,6,8a,9,10,11,12,12a,13,13a-decahydro-8H-isoquino[2,1-g][1,6]naphthyridine;
(8aR,12aS,13aS)-3-ethoxy-5,6,8a,9,10,11,12,12a,13,13a-decahydro-8H-isoquino[2,1-g][1,6]-naphthyridine;
(8aS,12aR,13aR)-3-ethoxy-5,6,8a,9,10,11,12,12a,13,13a-decahydro-8H-isoquino[2,1-g][1,6]-naphthyridine;
(8aR,12aS,13aS)-3-isopropoxy-5,6,8a,9,10,11,12,12a,13,-13a-decahydro-8H-isoquino[2,1-g][1,6]naphthyridine;
(8aS,12aR,13aR)-3-isobutoxy-5,6,8a,9,10,11,12,12a,13,-13a-decahydro-8H-isoquino[2,1-g][1,6]naphthyridine;
(8aR,12aS,13aS)-3-isopropoxy-5,6,8a,9,10,11,12,12a,13,-13a-decahydro-8H-isoquino[2,1-g][1,6]naphthyridine;
(8aS,12aR,13aR)-3-isobutoxy-5,6,8a,9,10,11,12,12a,13,-13a-decahydro-8H-isoquino[2,1-g][1,6]naphthyridine;
(8aR,12aS,13aS)-3-n-hexyloxy-5,6,8a,9,10,11,12,12a,13,-13a-decahydro-8H-isoquino[2,1-g][1,6]naphthyridine;
(8aS,12aR,13aR)-3-n hexyloxy-5,6,8a,9,10,11,12,-12a,13,13a-decahydro-8H-isoquino[2,1-g][1,6]naphthyridine;
(8aR,12aS,13aS)-3-hydroxy-5,6,8a,9,10,11,12,12a,13,-13a-decahydro-8H-isoquino[2,1-g][1,6]naphthyridine;
(8aS,12aR,13aR)-3-hydroxy-5,6,8a,9,10,11,12,12a,13,-13a-decahydro-8H-isoquino[2,1-g][1,6]naphthyridine;
(8aR,12aS,13aS)-2,3-dihydroxy-5,6,8a,9,10,11,12,-12a,13,13a-decahydro-8H-isoquino[2,1-g][1,6]naphthyridine;
(8aS,12aR,13aR)-2,3-dihydroxy-5,6,8a,9,10,11,12,-12a,13,13a-decahydro-8H-isoquino[2,1-g][1,6]naphthyridine;
(8aR,12aS,13aS)-1,2-dimethoxy-5,6,8a,9,10,11,12,-12a,13,13a-decahydro- 8H-isoquino[2,1-g][1,6]naphthyridine;
(8aS,12aR,13aR)-1,2-dimethoxy-5,6,8a,9,10,11,12,-12a,13,13a-decahydro-8H-isoquino[2,1-g][1,6]naphthyridine;
(8aR,12aS,13aS)-1,4-dimethoxy-5,6,8a,9,10,11,12,-12a,13,13a-decahydro-8H-isoquino[2,1-g][1,6]naphthyridine;
(8aS,12aR,13aR)-1,4-dimethoxy-5,6,8a,9,10,11,12,-12a,13,13a-decahydro-8H-isoquino[2,1-g][1,6]naphthyridine;
(8aR,12aS,13aS)-3,4-dimethoxy-5,6,8a,9,10,11,12,-12a,13,13a-decahydro-8H-isoquino[2,1-g][1,6]naphthyridine;
(8aS,12aR,13aR)-3,4-dimethoxy-5,6,8a,9,10,11,12,-12a,13,13a-decahydro-8H-isoquino[2,1-g][1,6]naphthyridine;
(8aR,12aS,13aS)-2,3-diethoxy-5,6,8a,9,10,11,12,12a,13,-13a-decahydro-8H-isoquino[2,1-g][1,6]naphthyridine;
(8aS,12aR,13aR)-2,3-diethoxy-5,6,8a,9,10,11,12,12a,13,-13a-decahydro-8H-isoquino[2,1-g][1,6]naphthyridine;
(8aR,12aS,13aS)-2,3-di-n-butoxy-5,6,8a,9,10,11,12,-12a,13,13a-decahydro-8H-isoquino[2,1-g][1,6]naphthyridine;
(8aS,12aR,13aR)-2,3-di-n-butoxy-5,6,8a,9,10,11,12,-12a,13,13a-decahydro-8H-isoquino[2,1-g][1,6]naphthyridine;
(8aR,12aS,13aS)-1,2-methylenedioxy-5,6,8a,9,10,11,12,-12a,13,13a-decahydro-8H-isoquino[2,1-g][1,6]naphthyridine;
(8aS,12aR,13aR)-1,2-methylenedioxy-5,6,8a,9,10,11,12,-12a,13,13a-decahydro-8H-isoquino[2,1-g][1,6]naphthyridine;
(8aR,12aS,13aS)-2-chloro-5,6,8a,9,10,11,12,12a,13,13a-decahydro-8H-isoquino[2,1-g][1,6]-naphthyridine;
(8aS,12aR,13aR)-2-chloro-5,6,8a,9,10,11,12,12a,13,13a-decahydro-8H-isoquino[2,1-g][1,6]-naphthyridine;
(8aR,12aS,13aS)-3-chloro-5,6,8a,9,10,11,12,12a,13,13a-decahydro-8H-isoquino[2,1-g][1,6]-naphthyridine;
(8aS,12aR,13aR)-3-chloro-5,6,8a,9,10,11,12,12a,13,13a-decahydro-8H-isoquino[2,1-g][1,6]-naphthyridine;
(8aR,12aS,13aS)-4-chloro-5,6,8a,9,10,11,12,12a,13,13a-decahydro-8H-isoquino[2,1-g][1,6]-naphthyridine;
(8aS,12aR,13aR)-4-chloro-5,6,8a,9,10,11,12,12a,13,13a-decahydro-8H-isoquino[2,1-g][1,6]-naphthyridine;
(8aR,12aS,13aS)-3-bromo 5,6,8a,9,10,11,12,12a,13,13a-decahydro-8H-isoquino[2,1-g][1,6]-naphthyridine;
(8aS,12aR,13aR)-3 bromo-5,6,8a,9,10,11,12,12a,13,13a-decahydro-8H-isoquino[2,1-g][1,6]-naphthyridine;
(8aR,12aS,13aS)-3-fluoro-5,6,8a,9,10,11,12,12a,13,13a-decahydro-8H-isoquino[2,1-g][1,6]-naphthyridine;
(8aS,12aR,13aR)-3-fluoro-5,6,8a,9,10,11,12,12a,13,13a-decahydro-8H-isoquino[2,1-g][1,6]-naphthyridine;
(8aR,12aS,13aS)-2-fluoro-5,6,8a,9,10,11,12,12a,13,13a-decahydro-8H-isoquino[2,1-g][1,6]-naphthyridine;
(8aS,12aR,13aR)-2-fluoro-5,6,8a,9,10,11,12,12a,13,13a-decahydro-8H-isoquino[2,1-g][1,6]-naphthyridine.

D. Similarly, replacing (8aR,12aS,13aS)-3-methoxy-12-(1-R-phenethylaminocarbonyl)-5,6,8a,9,10,11,12,12a,13,13a-decahydro-8H-isoquino[2,1-g][1,6]naphthyridine with other compounds of appropriate stereochemistry, prepared as shown in Preparation 5, and following the procedure in paragraph A above, the following exemplary compounds of formula (VIIIA) were prepared (8aR,12aS,13aS)-3-methoxy-5,6,8a,9,10,11,12,12a,13,13a-decahydro-8H-isoquino[2,1-g][1,6]naphthyridine;

mp 110°–112° C., $[\alpha]_D^{25} = +101.5$ (CHCl$_3$)

(8aR,12aS,13aR)-2,3-methylenedioxy-5,6,8a,9,10,11,12,12a,13,13a-decahydro-8H-isoquino[2,1-g][1,6]naphthyridine, E. Similarly, replacing (8aR,12aS,13aS)-3-methoxy-12-(1-R-phenethylaminocarbonyl)-5,6,8a,9,10,11,12,12a,13,13a-decahydro-8H-isoquino[2,1-g][1,6]naphthyridine with other compounds of appropriate stereochemistry, prepared as shown in Preparation 5, and following the procedure in paragraph A above, the following exemplary compounds of formula (VIIIA) are prepared:

(8aR,12aS,13aR)-5,6,8a,9,10,11,12,12a,13,13a-decahydro- 8H-isoquino[2,1-g][1,6]naphthyridine, (8aR,12aS,13aR)-2,3-dimethoxy-5,6,8a,9,10,11,12,-12a,13,13a-decahydro-8H-isoquino[2,1-g][1,6]naphthyridine;

(8aR,12aS,13aR)-1,4-dimethoxy-5,6,8a,9,10,11,12,-12a,13,13a-decahydro-8H-isoquino[2,1-g][1,6]naphthyridine;

(8aR,12aS,13aR)-2,3-(ethylene 1,2-dioxy)-5,6,8a,9,10,11,12,12a,13,13a-decahydro-8H-isoquino[2,1-g][1,6]naphthyridine;

(8aR,12aS,13aR)-1-methyl-5,6,8a,9,10,11,12,12a,13,13a-decahydro-8H-isoquino[2,1-g][1,6]-naphthyridine;

(8aR,12aS,13aR)-2-methyl-5,6,8a,9,10,11,12,12a,13,13a-decahydro-8H-isoquino[2,1-g][1,6]-naphthyridine;

(8aR,12aS,13aR)-3-methyl-5,6,8a,9,10,11,12,12a,13,13a-decahydro-8H-isoquino[2,1-g][1,6]-naphthyridine;

(8aR,12aS,13aR)-2,3-dimethyl-5,6,8a,9,10,11,12,12a,13,-13a-decahydro-8H-isoquino[2,1-g][1,6]naphthyridine;

(8aR,12aS,13aR)-3-ethyl-5,6,8a,9,10,11,12,12a,13,13a-decahydro-8H-isoquino-[2,1-g][1,6]-naphthyridine;

(8aR,12aS,13aR)-3-isobutyl-5,6,8a,9,10,11,12,12a,13,-13a-decahydro-8H-isoquino[2,1-g][1,6]naphthyridine;

(8aR,12aS,13aR)-3-n-hexyl-5,6,8a,9,10,11,12,12a,13,13a-decahydro-8H-isoquino[2,1-g][1,6]naphthyridine;

(8aR,12aS,13aR)-1-methoxy-5,6,8a,9,10,11,12,12a,13,-13a-decahydro-8H-isoquino[2,1-g][1,6]naphthyridine;

(8aR,12aS,13aR)-2-methoxy-5,6,8a,9,10,11,12,12a,13,-13a-decahydro-8H-isoquino[2,1-g][1,6]naphthyridine;

(8aR,12aS,13aR)-4-methoxy-5,6,8a,9,10,11,12,12a,13,-13a-decahydro-8H-isoquino[2,1-g][1,6]naphthyridine;

(8aR,12aS,13aR)-3-methoxy-2-methyl-5,6,8a,9,10,11,12,12a,13,13a-decahydro-8H-isoquino[2,1-g][1,6]naphthyridine;

(8aR,12aS,13aR)-3-ethoxy-5,6,8a,9,10,11,12,12a,13,13a-decahydro-8H-isoquino[2,1-g][1,6]-naphthyridine;

(8aR,12aS,13aR)-3-isopropoxy-5,6,8a,9,10,11,12,-12a,13,13a-decahydro-8H-isoquino[2,1-g][1,6]-naphthyridine;

(8aR,12aS,13aR)-3-isopropoxy-5,6,8a,9,10,11,12,-12a,13,13a-decahydro-8H-isoquino[2,1-g][1,6]naphthyridine;

(8aR,12aS,13aR)-3-n-hexyloxy-5,6,8a,9,10,11,12,-12a,13,13a-decahydro-8H-isoquino[2,1-g][1,6]naphthyridine;

(8aR,12aS,13aR)-3-hydroxy-5,6,8a,9,10,11,12,12a,13,-13a-decahydro-8H-isoquino[2,1-g][1,6]naphthyridine;

(8aR,12aS,13aR)-2,3-dihydroxy-5,6,8a,9,10,11,12,-12a,13,13a-decahydro-8H-isoquino[2,1-g][1,6]naphthyridine;

(8aR,12aS,13aR)-1,2-dimethoxy-5,6,8a,9,10,11,12,-12a,13,13a-decahydro-8H-isoquino[2,1-g][1,6]naphthyridine;

(8aR,12aS,13aR)-1,4-dimethoxy-5,6,8a,9,10,11,12,-12a,13,13a-decahydro-8H-isoquino[2,1-g][1,6]naphthyridine;

(8aR,12aS,13aR)-3,4-dimethoxy-5,6,8a,9,10,11,12,-12a,13,13a-decahydro-8H-isoquino[2,1-g][1,6]naphthyridine;

(8aR,12aS,13aR)-2,3-diethoxy-5,6,8a,9,10,11,12,12a,13,-13a-decahydro-8H-isoquino[2,1-g][1,6]naphthyridine;

(8aR,12aS,13aR)-2,3-di-n-butoxy-5,6,8a,9,10,11,12,-12a,13,13a-decahydro-8H-isoquino[2,1-g][1,6]naphthyridine;

(8aR,12aS,13aR)-1,2-methylenedioxy-5,6,8a,9,10,11,12,-12a,13,13a-decahydro-8H-isoquino[2,1-g][1,6]naphthyridine;

(8aR,12aS,13aR)-2-chloro-5,6,8a,9,10,11,12,12a,13,13a-decahydro-8H-isoquino[2,1-g][1,6]-naphthyridine;

(8aR,12aS,13aR)-3-chloro-5,6,8a,9,10,11,12,12a,13,13a-decahydro-8H-isoquino[2,1-g][1,6]-naphthyridine;

(8aR,12aS,13aR)-4-chloro-5,6,8a,9,10,11,12,12a,13,13a-decahydro-8H-isoquino[2,1-g][1,6]-naphthyridine;

(8aR,12aS,13aR)-3-bromo-5,6,8a,9,10,11,12,12a,13,13a-decahydro-8H-isoquino[2,1-g][1,6]-naphthyridine;

(8aR,12aS,13aR)-3-fluoro-5,6,8a,9,10,11,12,12a,13,13a-decahydro-8H-isoquino[2,1-g][1,6]-naphthyridine; and (8aR,12aS,13aR)-2-fluoro-5,6,8a,9,10,11,12,12a,13,13a-decahydro-8H-isoquino[2,1-g][1,6]-naphthyridine.

EXAMPLE 1

Preparation of
(±)-12-N,N-Dimethylaminocarbonyl-5,6,8a$\alpha$,9,10,11,12,12a$\alpha$,13,13a$\alpha$-decahydro-8H-isoquino[2,1-g][1,6]naphthyridine hydrochloride and Related Compounds of Formula (1) and (2) where Z is —NR$^3$R$^4$ A solution of 4.5 g of (±)-5,6,8a$\alpha$,9,10,11,12,-12a$\alpha$,13,13a$\alpha$-decahydro-8H-isoquino[2,1-g][1,6]naphthyridine (VII) and 6.6 ml of triethylamine in 100 ml of methylene chloride was stirred at room temperature and 1.56 ml of dimethylcarbamyl chloride was added. The mixture was stirred at room temperature for 16 hours, then solvent removed under reduced pressure. The residue was partitioned between 200 ml of methylene chloride and 50 ml of 2N sodium carbonate. The organic phase was dried over anhydrous magnesium sulfate, the solvent removed under reduced pressure, and the residue chromatographed on silica gel, eluting with 3% methanol/methylene chloride. The product was dissolved in ethanol and acidified with ethanolic HCl. Crystallization was induced by adding a small amount of diethylether, to give (±)-12-N,N-dimethylaminocarbonyl-5,6,8aα,9,10,11,12,12aα,13,13aα-decahydro-8H-isoquino[2,1-g][1,6]naphthyridine hydrochloride, m.p. 227°-228° C.

B. Similarly, optionally replacing (±)-5,6,8aα,9,10,11,12,12aα,13,13aα-decahydro-8H-isoquino[2,1-g][1,6]naphthyridine with the appropriate compound of formula (VII), (VIII) or (VIIA) and optionally replacing dimethyl carbamyl chloride with other carbamoyl chlorides or thiocarbamyl chlorides of formula $R^3R^4C(W)Cl$, where $R^3$ and $R^4$ are as defined supra, and following the procedure in paragraph A above, the following compounds of formula (1) and (2) were prepared:

(8aR,12aS,13aS)-12-N,N-dimethylaminocarbonyl-5,6,8a,9,10,11,12,12a,13,13a-decahydro-8H-isoquino[2,1-g][1,6]naphthyridine hydrochloride, mp 262°-263° C., $[\alpha]_D^{25} = +38$ (C=0.005635, MeOH);

(±)-12-N,N-diethylaminocarbonyl-5,6,8aα,9,10,11,12,-12aα,13,13aα-decahydro-8H-isoquino[2,1-g][1,6]naphthyridine hydrochloride, m.p. 185°-187° C.;

(±)-3-methoxy-12-N,N-dimethylaminocarbonyl-5,6,8aα,9,10,11,12,12aα,13,13aα-decahydro-8H-isoquino-[2,1-g][1.6]naphthyridine hydrochloride, m.p. 228°-230° C.;

(±)-2,3-methylenedioxy-12-N,N-dimethylaminocarbonyl-5,6,8aα,9,10,11,12,12aα,13,13aα-decahydro-8H-isoquino[2,1-g][1,6]naphthyridine hydrochloride, m.p. 266°-267° C.;

(8aR,12aS,13aS)-2,3-methylenedioxy-12-N,N-dimethylaminocarbonyl-5,6,8a,9,10,11,12,12a,13,13a-decahydro-8H-isoquino[2,1-g][1,6]naphthyridine hydrochloride, mp 245°-247° C., $[\alpha]_D^{25} = +23.7$ (C=1.25, MeOH);

(±)-3-methoxy-12-(pyrrolidin-1-yl)carbonyl5,6-,8aα,9,10,11,12,12aα,13,13aα-decahydro-8H-isoquino[2,1-g][1,6]naphthyridine hydrochloride, m.p. 252°-253° C.;

(±)-3-methoxy-12-(4-methylpiperazin-1-yl)carbonyl-5,6,8aα,9,10,11,12,12aα,13,13aα-decahydro-8H-isoquino[2,1-g][1,6]naphthyridine hydrochloride, m.p. 241°-242° C.;

(±)-3 oxy-12-(morpholin-1-yl)carbonyl-5,6,8aα,9,10,11,12,12aα,13,13aα-decahydro-8H-isoquino[2,1-g][1,6]naphthyridine hydrochloride, m.p. 181°-182° C.;

(±)-3-methyl-12-N,N-dimethylaminocarbonyl-5,6,8aα,9,10,11,12,12aα,13,13aα-decahydro-8H-isoquino[2,1-g][1,6]naphthyridine hydrochloride, m.p. 256°-257° C.;

(±)-2,3-dimethoxy-12-N,N-dimethylaminocarbonyl-5,6,aα,9,10,11,12,12aα,13,13aα-decahydro-8H-isoquino[2,1-g][1,6]naphthyridine hydrochloride, m.p. 146°-147° C.; and (8aR,12aS,13aS)-12-N,N-dimethylaminothiocarbonyl-5,6,8a,9,10,11,12,12a,13,13a-decahydro-8H-isoquino[2,1-g][1,6]naphthyridine hydrochloride, mp 276°-277° C., $[\alpha]_D^{25} = -79.7$ (Free base, C=0.9, CHCl₃);

C. Similarly, optionally replacing (±)-5,6,8aα,9,10,11,12,12aα,13,13aα-decahydro-8H-isoquino[2,1-g][1,6]naphthyridine with the appropriate compound of formula (VII), (VIII), (VIIA), (VIIB), (VIIIA) or (VIIIB), optionally replacing dimethylcarbamyl chloride with other carbamoyl chlorides or thiocarbamyl chlorides of formula $R^3R^4C(W)Cl$, where W, $R^3$ and $R^4$ are as defined supra, and following the procedure in Paragraph A above, the following exemplary compounds of formula (1) and (2) are prepared. It should be understood that for the sake of brevity each name is intended to identify both of the individual enantiomers of a racemic mixture and the racemic mixture itself, obtained depending upon the starting material employed.

12-N-methyl-N-ethylaminocarbonyl-5,6,8aα,9,10,11,12,12aα,13,13aα-decahydro-8H-isoquino[2,1-g][1,6]naphthyridine hydrochloride;

12-N-methyl-N-ethylaminocarbonyl-5,6,8aα,9,10,11,12,12aα,13,13aα-decahydro-8H-isoquino[2,1-g][1,6]naphthyridine hydrochloride;

12-N-methyl-N-butylaminocarbonyl-5,6,8aα,9,10,11,12,12aα,13,13aα-decahydro-8H-isoquino[2,1-g][1,6]naphthyridine hydrochloride;

12-N-methyl-N-butylaminocarbonyl-5,6,8aα,9,10,11,12,12aα,13,13aα-decahydro-8H-isoquino[2,1-g][1,6]naphthyridine hydrochloride;

12-N,N-di-n-hexylaminocarbonyl-5,6,8aα,9,10,11,12,-12aα,13,13aα-decahydro- 8H-isoquino[2,1-g][1,6]naphthyridine hydrochloride;

12-N,N-di-n-hexylaminocarbonyl-5,6,8aβ,9,10,11,12,-12aβ,13,13aα-decahydro-8H-isoquino[2,1-g][1,6]naphthyridine hydrochloride;

12-N,N-diphenylaminocarbonyl-5,6,8aα,9,10,11,12,-12aα,13,13aα-decahydro-8H-isoquino[2,1-g][1,6]naphthyridine hydrochloride;

12-N,N-diphenylaminocarbonyl-5,6,8aβ,9,10,11,12,-12aβ,13,13aα-decahydro-8H-isoquino[2,1-g][1,6]naphthyridine hydrochloride;

12-(pyrrolidin-1-yl)carbonyl-5,6,8aα,9,10,11,12,2aα,13,-13aα-decahydro-8H-isoquino[2,1-g][1,6]naphthyridine hydrochloride;

12-(pyrrolidin-1-yl)carbonyl-5,6,8aβ,9,10,11,12, aβ,13,-13aα-decahydro-8H-isoquino[2,1-g][1,6]naphthyridine hydrochloride;

12-(4-methylpiperazin-1-yl)carbonyl-5,6,8aα,9,10,11,12,12aα,13,13aα-decahydro-8H-isoquino[2,1-g][1,6]naphthyridine hydrochloride;

12-(4-methylpiperazin-1-yl)carbonyl-5,6,8aβ,9,10,11,12,12aβ,13,13aα-decahydro-8H-isoquino[2,1-g][1,6]naphthyridine hydrochloride;

12-(morpholin-1-yl)carbonyl-5,6,8aα,9,10,11,12,-12aα,13,13aα-decahydro-8H-isoquino[2,1-g][1,6]naphthyridine hydrochloride;

12-(morpholin-1-yl)carbonyl-5,6,8aβ,9,10,11,12,aβ,13,-13aα-decahydro-8H-isoquino[2,1-g][1,6]naphthyridine hydrochloride;

3-methoxy-12-N-methyl-N-ethylaminocarbonyl-5,6,8aα,9,10,11,12,12aα,13,13aα-decahydro-8H-isoquino[2,1-g][1,6]naphthyridine hydrochloride;

3-methoxy-12-N-methyl-N-ethylaminocarbonyl-5,6,8aβ,9,10,11,12,12aβ,13,13aα-decahydro-8H-isoquino[2,1-g][1,6]naphthyridine hydrochloride;

3-methoxy-12-N-methyl-N-butylaminocarbonyl-5,6,8aα,9,10,11,12,12aα,13,13aα-decahydro-8H-isoquino[2,1-g][1,6]aphthyridine hydrochloride;

3-methoxy-12-N-methyl-N-butylaminocarbonyl-5,6,8aβ,9,10,11,12,12aβ,13,13aα-decahydro-8H-isoquino[2,1-g][1,6]naphthyridine hydrochloride;

3-methoxy-12-N,N-di-n-hexylaminocarbonyl-5,6,8aα,9,10,11,12,12aα,13,13aα-decahydro-8H-isoquino[2,1-g][1,6]naphthyridine hydrochloride;

3-methoxy-12-N,N-di-n-hexylaminocarbonyl-5,6,8aβ,9,10,11,12,12aβ,13,13aα-decahydro-8H-isoquino[2,1-g][1,6]naphthyridine hydrochloride;

3-methoxy-12-N,N-diphenylaminocarbonyl-5,6,8aα,9,10,11,12,12aα,13,13aα-decahydro-8H-isoquino[2,1-g][1,6]naphthyridine hydrochloride;

3-methoxy-12-N,N-diphenylaminocarbonyl-5,6,8aβ,9,10,11,12,12aβ,13,13aα-decahydro-8H-isoquino[2,1-g][1,6]naphthyridine hydrochloride;

2,3-methylenedioxy-12-N-methyl-N-ethylaminocarbonyl-5,6,8aα,9,10,11,12,12aα,13,13aα-decahydro-8H-isoquino[2,1-g][1,6]naphthyridine hydrochloride;

2,3-methylenedioxy-12-N-methyl-N-ethylaminocarbonyl-5,6,8aβ,9,10,11,12,12aβ,13,13aα-decahydro-8H-isoquino[2,1-g][1,6]naphthyridine hydrochloride;

2,3-ethylenedioxy-12-N,N-dimethylaminocarbonyl-5,6,8aα,9,10,11,12,12aα,13,13aα-decahydro-8H-isoquino[2,1-g][1,6]naphthyridine hydrochloride;

2,3-ethylenedioxy-12-N,N-dimethylaminocarbonyl-5,6,8aβ,9,10,11,12,12aβ,13,13aα-decahydro-8H-isoquino[2,1-g][1,6]naphthyridine hydrochloride;

2,3-methylenedioxy-12-N-methyl-N-butylaminocarbonyl-5,6,8aα,9,10,11,12,12aα,13,13aα-decahydro-8H-isoquino[2,1-g][1,6]aphthyridine hydrochloride;

2,3-methylenedioxy-12-N-methyl-N-butylaminocarbonyl-5,6,8aβ,9,10,11,12,12aβ,13,13aα-decahydro-8H-isoquino[2,1-g][1,6]naphthyridine hydrochloride;

2,3-methylenedioxy-12-N,N-di-n-hexylaminocarbonyl-5,6,8aα,9,10,11,12,12aα,13,13aα-decahydro-8H-isoquino[2,1-g][1,6]naphthyridine hydrochloride;

2,3-methylenedioxy-12-N,N-di-n-hexylaminocarbonyl-5,6,8aβ,9,10,11,12,12aβ,13,13aα-decahydro-8H-isoquino[2,1-g][1,6]naphthyridine hydrochloride;

2,3-methylenedioxy-12-N,N-diphenylaminocarbonyl-5,6,8aα,9,10,11,12,12aα,13,13aα-decahydro-8H-isoquino[2,1-g][1,6]naphthyridine hydrochloride;

2,3-methylenedioxy-12-N,N-diphenylaminocarbonyl-5,6,8aβ,9,10,11,12,12aβ,13,13aα-decahydro-8H-isoquino[2,1-g][1,6]naphthyridine hydrochloride;

2,3-methylenedioxy-12-(pyrrolidin-1-yl)carbonyl-5,6,8aα,9,10,11,12,12aα,13,13aα-decahydro-8H-isoquino[2,1-g][1,6]naphthyridine hydrochloride;

2,3-methylenedioxy-12-(pyrrolidin-1-yl)carbonyl-5,6,8aβ,9,10,11,12,12aβ,13,13aα-decahydro-8H-isoquino[2,1-g][1,6]naphthyridine hydrochloride;

2,3-methylenedioxy-12-(4-methylpiperazin-1-yl)carbonyl-5,6,8aα,9,10,11,12,12aα,13,13aα-decahydro-8H-isoquino[2,1-g][1,6]naphthyridine hydrochloride;

2,3-methylenedioxy-12-(4-methylpiperazin-1-yl)carbonyl-5,6,8aβ,9,10,11,12,12aβ,13,13aα-decahydro-8H-isoquino[2,1-g][1,6]naphthyridine hydrochloride;

2,3-methylenedioxy-12-(morpholin-1-yl)carbonyl-5,6,8aα,10,11,12,12aα,13,13aα-decahydro-8H-isoquino[2,1-g][1,6]naphthyridine hydrochloride;

2,3-methylenedioxy-12-(morpholin-1-yl)carbonyl-5,6,8aβ,10,11,12,12aβ,13,13aα-decahydro-8H-isoquino[2,1-g][1,6]naphthyridine hydrochloride;

2-methyl-12-N,N-dimethylaminocarbonyl-5,6,8aα,9,10,11,12,12aα,13,13aα-decahydro-8H-isoquino[2,1-g][1,6]naphthyridine hydrochloride;

2-methyl-12-N,N-dimethylaminocarbonyl-5,6,8aβ,9,10,11,12,12aβ,13,13aα-decahydro- 8H-isoquino[2,1-g][1,6]naphthyridine hydrochloride;

3-methyl-12-N,N-dimethylaminocarbonyl-5,6,8aα,9,10,11,12,12aβ,13,13aα-decahydro-8H-isoquino[2,1-g][1,6]naphthyridine hydrochloride;

2,3-dimethyl-12-N,N-dimethylaminocarbonyl-5,6,8aα,9,10,11,12,12aα,13,13aα-decahydro-8H-isoquino[2,1-g][1,6]naphthyridine hydrochloride;

2,3-dimethyl-12-N,N-dimethylaminocarbonyl-5,6,8aβ,9,10,11,12,12aβ,13,13aα-decahydro-8H-isoquino[2,1-g][1,6]naphthyridine hydrochloride;

3-n hexyl-12-N,N-dimethylaminocarbonyl-5,6,8aα,9,10,11,12,12aα,13,13aα-decahydro-8H-isoquino2,1-g][1,6]naphthyridine hydrochloride;

3-n-hexyl-12-N,N-dimethylaminocarbonyl-5,6,8aβ,9,10,11,12,12aβ,13,13aα-decahydro-8H-isoquino[2,1-g][1,6]naphthyridine hydrochloride;

2-methoxy-12-N,N-dimethylaminocarbonyl-5,6,8aα,9,10,11,12,12aα,13,13aα-decahydro-8H-isoquino[2,1-g][1,6]naphthyridine hydrochloride;

2-methoxy-12-N,N-dimethylaminocarbonyl-5,6,8aβ,9,10,11,12,12aβ,13,13aα-decahydro-8H-isoquino[2,1-g][1,6]naphthyridine hydrochloride;

3-ethoxy-12-N,N-dimethylaminocarbonyl-5,6,8aα,9,10,11,12,12aα,13,13aα-decahydro-8H-isoquino[2,1-g][1,6]naphthyridine hydrochloride;

3-ethoxy-12-N,N-dimethylaminocarbonyl-5,6,8aβ,9,10,11,12,12aβ,13,13aα-decahydro-8H-isoquino[2,1-g][1,6]naphthyridine hydrochloride;

3-n-hexyloxy-12-N,N-dimethylaminocarbonyl-5,6,8aα,9,10,11,12,12aα,13,13aα-decahydro-8H-isoquino[2,1-g][1,6]naphthyridine hydrochloride;

3-n-hexyloxy-12-N,N-dimethylaminocarbonyl-5,6,8aβ,9,10,11,12,12aβ,13,13aα-decahydro-8H-isoquino[2,1-g][1,6]naphthyridine hydrochloride;

3-hydroxy-12-N,N-dimethylaminocarbonyl-5,6,8aα,9,10,11,12,12aα,13,13aα-decahydro-8H-isoquino[2,1-g][1,6]naphthyridine hydrochloride;

3-hydroxy-12-N,N-dimethylaminocarbonyl-5,6,8aβ,9,10,11,12,12aβ,13,13aα-decahydro-8H-isoquino[2,1-g][1,6]naphthyridine hydrochloride;

2,3-dimethoxy-12-N,N-dimethylaminocarbonyl-5,6,8aβ,9,10,11,12,12aβ,13,13aα-decahydro-8H-isoquino[2,1-g][1,6]naphthyridine hydrochloride;

3,4-methylenedioxy-12-N,N-dimethylaminocarbonyl-5,6,8aα,9,10,11,12,12aα,13,13aα-decahydro-8H-isoquino[2,1-g][1,6]naphthyridine hydrochloride;

3,4-methylenedioxy-12-N,N-dimethylaminocarbonyl-5,6,8aβ,9,10,11,12,12aβ,13,13aα-decahydro-8H-isoquino[2,1-g][1,6]naphthyridine hydrochloride;

3-chloro-12-N,N-dimethylaminocarbonyl-5,6,8aα,9,10,11,12,12aα,13,13aα-decahydro-8H-isoquino[2,1-g][1,6]naphthyridine hydrochloride;

3-chloro-12-N,N-dimethylaminocarbonyl-5,6,8aβ,9,10,11,12,12aβ,13,13aα-decahydro-8H-isoquino[2,1-g][1,6]naphthyridine hydrochloride;

3-fluoro-12-N,N-dimethylaminocarbonyl-5,6,8aα,9,10,11,12,12aα,13,13aα-decahydro-8H-isoquino[2,1-g][1,6]naphthyridine hydrochloride;

3-fluoro-12-N,N-dimethylaminocarbonyl-5,6,8aβ,9,10,11,12,12aβ,13,13aα-decahydro-8H-isoquino[2,1-g][1,6]naphthyridine hydrochloride;

12-N,N-dimethylaminothiocarbonyl-5,6,8a,9,10,11,12,-12a,13,13a-decahydro-8H-isoquino[2,1-g][1,6]-naphthyridine hydrochloride;

3-methoxy-12-N,N-dimethylaminothiocarbonyl-5,6,8aα,9,10,11,12,12aα,13,13aα-decahydro-8H-isoquino[2,1-g][1,6]naphthyridine hydrochloride;

2,3-methylenedioxy-12-N,N-dimethylaminothiocarbonyl-5,6,8aα,9,10,11,12,12aα,13,13aα-decahydro- 8H-isoquino[2,1-g][1,6]naphthyridine hydrochloride;

3-methyl-12-N,N-dimethylaminothiocarbonyl-5,6,8aα,9,10,11,12,12aα,13,13aα-decahydro-8H-isoquino[2,1-g][1,6]naphthyridine hydrochloride; and 2,3-dimethoxy-12-N,N-dimethylaminothiocarbonyl-5,6,8aα,9,10,11,12,12aα,13,13aα-decahydro-8H-isoquino[2,1-g][1,6]naphthyridine hydrochloride.

EXAMPLE 1A

Alternative Preparation of (8aR,12aS,13aS)-2,3 methylenedioxy-12-N,N-dimethylaminocarbonyl-5,6,8a,9,10,11,12,12a,13,13a-decahydro-8H-isoquino-[2,1g][1,6]naphthyridine hydrochloride and Related Compounds of Formula (1)

A solution of 2.0 g of (8aR,12aS,13aR)-2,3-methylenedioxy-12-N,N-dimethylaminocarbonyl-5,6,8a,9,10,11,12,12a,13,13a-decahydro-8H-isoquino[2,1-g][1,6]naphthyridine (a compound of formula (2)) was dissolved in 25 ml of chloroform, cooled to 0° C. and 1.4 g of 80% m-chloroperbenzoic acid added. The solution was stirred for 1 hour at 0° C., then 3 ml of trifluoroacetic anhydride added and the mixture stirred for 30 minutes at room temperature. The solvent was removed under reduced pressure at room temperature. The residue was dissolved in 25 ml of ethanol, cooled to 0° C. and sodium borohydride slowly added until the solution was basic. Solvent was removed under reduced pressure and the residue partitioned between ethyl acetate and dilute hydrochloric acid. The aqueous solution was separated and basified with ammonium hydroxide, then extracted three times with methylene chloride. Solvent was removed from the combined extracts and the product dissolved in ethanol and acidified with ethanolic HCl. Solvent was removed from the solution, and the residue crystallized from ethanol/diethylether, giving (8aR,12aS,13aS)-2,3-methylenedioxy-12-N,N-dimethylaminocarbonyl-5,6,8a,9,10,11,12,-12a,13,13a-decahydro-8H-isoquino[2,1g][1,6]naphthyridine hydrochloride, mp 245°-247° C., $[\alpha]_D^{25} = +23.7$ (CHCl$_3$).

B. Alternatively, the conversion of a compound of formula (2) to a compound of formula (1) may be accomplished by the following procedure.

A mixture of 1.14 g of (8aR,12aS,13aR)-2,3-methylenedioxy-12-N,N-dimethylaminocarbonyl-5,6,8a,9,10,11,12,12a,13,13a-decahydro-8H-isoquino[2,1-g][1,6]naphthyridine (a compound of formula (2)) and 4.53 g of mercuric acetate in 20 ml of acetic acid and 2 ml of water is stirred at 105° C. for 1 hour. The mixture is filtered and hydrogen sulfide is bubbled through the filtrate for 5 minutes. The mixture is filtered again and the filtrate is concentrated under reduced pressure. Ethanol (50 ml) is added and the resulting solution is cooled to −20° C. and treated with 0.5 g of sodium borohydride. The solution is allowed to warm to room temperature and acidified with aqueous HCl. After washing with ethyl acetate, the aqueous layer is basified with NH$_4$OH and extracted with ethyl acetate. The ethyl acetate is washed with brine, dried over anhydrous sodium sulfate and evaporated. Chromatography of the residue on silica gel, eluting with 1% methanol in methylene chloride, affords (8aR,12aS,13aS)-2,3-methylenedioxy-12-N,N-dimethylaminocarbonyl-5,6,8a,9,10,11,12,12a,13,13a-decahydro-8H-isoquino[2,1g][1,6]naphthyridine hydrochloride.

C. Similarly, replacing (8aR,12aS,13aR)-2,3-methylenedioxy-12-N,N-dimethylaminocarbonyl-5,6,8a,9,10,11,12,12a,13,13a-decahydro-8H-isoquino[2,1-g][1,6]naphthyridine with other compounds of formula (2) and following the procedure of paragraph A or B above, the following compounds of formula (1) are prepared. It should be noted that starting with a racemic compound of formula (2) leads to a racemic compound of formula (1), but starting with a chiral compound of formula (2) gives rise to a compound of formula (1) with the same chirality as the starting material.

12-N,N-dimethylaminocarbonyl-5,6,8aα,9,10,11,12,-12aα,13,13aα-decahydro-8H-isoquino[2,1-g][1,6]naphthyridine hydrochloride;

12-N,N-dimethylaminocarbonyl-5,6,8aα,9,10,11,12,-12aα,13,13aα-decahydro-8H-isoquino[2,1-g][1,6]naphthyridine hydrochloride;

12-N,N-diethylaminocarbonyl-5,6,8aα,9,10,11,12,-12aα,13,13aα-decahydro-8H-isoquino[2,1-g][1,6]naphthyridine hydrochloride;

3-methoxy-12-N,N-dimethylaminocarbonyl-5,6,8aα,9,10,11,12,12aα,13,13aα-decahydro-8H-isoquino[2,1-g][1,6]naphthyridine hydrochloride;

3-methoxy12-(pyrrolidin-1-yl)carbonyl-5,6,8aα,9,10,11,12,12aα,13,13aα-decahydro-8H-isoquino[2,1-g][1,6]naphthyridine hydrochloride;

3-methoxy-12-(4-methylpiperazin-1-yl)carbonyl-5,6,8aα,9,10,11,12,12aα,13,13aα-decahydro-8H-isoquino[2,1-g][1,6]naphthyridine hydrochloride;

3-methoxy-12-(morpholin-1-yl)carbonyl-5,6,8aα,9,10,11,12,12aα,13,13aα-decahydro-8H-isoquino[2,1-g][1,6]naphthyridine hydrochloride;

12-N-methyl-N-ethylaminocarbonyl-5,6,8aα,9,10,11,12,12aα,13,13aα-decahydro-8H-isoquino[2,1-g][1,6]naphthyridine hydrochloride;

12-N-methyl-N-butylaminocarbonyl-5,6,8aα,9,10,11,12,12aα,13,13aα-decahydro-8H-isoquino[2,1-g][1,6]naphthyridine hydrochloride;

12-N,N-di-n-hexylaminocarbonyl-5,6,8aα,9,10,11,12,-12aα,13,13aα-decahydro-8H-isoquino[2,1-g][1,6]naphthyridine hydrochloride;

12-N,N-diphenylaminocarbonyl-5,6,8aα,9,10,11,12,-12aα,13,13aα-decahydro-8H-isoquino[2,1-g][1,6]naphthyridine hydrochloride;

12-(pyrrolidin-1-yl)carbonyl-5,6,8aα,9,10,11,12,-12aα,13,13aα-decahydro-8H-isoquino[2,1-g][1,6]naphthyridine hydrochloride;

12-(4-methylpiperazin-1-yl)carbonyl-5,6,8aα,9,10,11,12,12aα,13,13aα-decahydro-8H-isoquino[2,1-g][1,6]naphthyridine hydrochloride;

12-(morpholin-12-yl)carbonyl-5,6,8aα,9,10,11,12,-12aα,13,13aα-decahydro-8H-isoquino[2,1-g][1,6]naphthyridine hydrochloride;

3-methoxy-12-N-methyl-N-ethylaminocarbonyl-5,6,8aα,9,10,11,12,12aα,13,13aα-decahydro-8H-isoquino[2,1-g][1,6]naphthyridine hydrochloride;

3-methoxy-12-N-methyl-N-butylaminocarbonyl-5,6,8aα,9,10,11,12,12aα,13,13aα-decahydro-8H-isoquino[2,1-g][1,6]aphthyridine hydrochloride;

3-methoxy-12-N,N-di-n-hexylaminocarbonyl-5,6,8aα,9,10,11,12,12aα,13,13aα-decahydro-8H-isoquino[2,1-g][1,6]naphthyridine hydrochloride;

3-methoxy-12-N,N-diphenylaminocarbonyl-5,6,8aα,9,10,11,12,12aα,13,13aα-decahydro-8H-isoquino[2,1-g][1,6]naphthyridine hydrochloride;

2,3-methylenedioxy-12-N-methyl-N-ethylaminocarbonyl-5,6,8aα,9,10,11,12,12aα,13,13aα-decahydro-8H-isoquino[2,1-g][1,6]naphthyridine hydrochloride;

2,3-ethylenedioxy-12-N,N-dimethylaminocarbonyl-5,6,8aα,9,10,11,12,12aα,13,13aα-decahydro-8H-isoquino[2,1-g][1,6]naphthyridine hydrochloride;

2,3-methylenedioxy-12-N-methyl-N-butylaminocarbonyl-5,6,8aα,9,10,11,12,12aα,13,13aα-decahydro-8H-isoquino[2,1-g][1,6]aphthyridine hydrochloride;

2,3-methylenedioxy-12-N,N-di-n-hexylaminocarbonyl-5,6,8aα,9,10,11,12,12aα,13,13aα-decahydro-8H-isoquino[2,1-g][1,6]naphthyridine hydrochloride;

2,3-methylenedioxy-12-N,N-diphenylaminocarbonyl-5,6,8aα,9,10,11,12,12aα,13,13aα-decahydro-8H-isoquino[2,1-g][1,6]naphthyridine hydrochloride;

2,3-methylenedioxy-12-(pyrrolidin-1-yl)carbonyl-5,6,8aα,9,10,11,12,12aα,13,13aα-decahydro-8H-isoquino[2,1-g][1,6]naphthyridine hydrochloride;

2,3-methylenedioxy-12-(4-methylpiperazin-1-yl)carbonyl-5,6,8aα,9,10,11,12,12aα,13,13aα-decahydro-8H-isoquino[2,1-g][1,6]naphthyridine hydrochloride;

2,3-methylenedioxy-12-(morpholin-1-yl)carbonyl-5,6,8aα,9,10,11,12,12aα,13,13aα-decahydro-8H-isoquino[2,1-g][1,6]naphthyridine hydrochloride;

2-methyl-12-N,N-dimethylaminocarbonyl-5,6,8aα,9,10,11,12,12aα,13,13aα-decahydro-8H-isoquino[2,1-g][1,6]naphthyridine hydrochloride;

3-methyl-12-N,N-dimethylaminocarbonyl-5,6,8aα,9,10,11,12,12aα,13,13aα-decahydro-8H-isoquino[2,1-g][1,6]naphthyridine hydrochloride;

2,3-dimethyl-12-N,N-dimethylaminocarbonyl-5,6,8aα,9,10,11,12,12aα,13,13aα-decahydro-8H-isoquino[2,1-g][1,6]naphthyridine hydrochloride;

3-n-hexyl-12-N,N-dimethylaminocarbonyl-5,6,8aα,9,10,11,12,12aα,13,13aα-decahydro-8H-isoquino[2,1-g][1,6]naphthyridine hydrochloride;

2-methoxy-12-N,N-dimethylaminocarbonyl-5,6,8aα,9,10,11,12,12aα,13,13aα-decahydro-8H-isoquino[2,1-g][1,6]naphthyridine hydrochloride;

3-ethoxy-12-N,N-dimethylaminocarbonyl-5,6,8aα,9,10,11,12,12aα,13,13aα-decahydro-8H-isoquino[2,1-g][1,6]naphthyridine hydrochloride;

3-n-hexyloxy-12-N,N-dimethylaminocarbonyl-5,6,8aα,9,10,11,12,12aα,13,13aα-decahydro-8H-isoquino[2,1-g][1,6]naphthyridine hydrochloride;

3-hydroxy-12-N,N-dimethylaminocarbonyl-5,6,8aα,9,10,11,12,12aα,13,13aα-decahydro-8H-isoquino[2,1-g][1,6]naphthyridine hydrochloride;

2,3-dimethoxy-12-N,N-dimethylaminocarbonyl-5,6,8aα,9,10,11,12,12aα,13,13aα-decahydro-8H-isoquino[2,1-g][1,6]naphthyridine hydrochloride;

3,4-methylenedioxy-12-N,N-dimethylaminocarbonyl-5,6,8aα,9,10,11,12,12aα,13,13aα-decahydro-8H-isoquino[2,1-g][1,6]naphthyridine hydrochloride;

3-chloro-12-N,N-dimethylaminocarbonyl-5,6,8aα,9,10,11,12,12aα,13,13aα-decahydro-8H-isoquino[2,1-g][1,6]naphthyridine hydrochloride; and 3-fluoro-12-N,N-dimethylaminocarbonyl-5,6,8aα,9,10,11,12,12aα,13,13aα-decahydro-8H-isoquino[2,1-g][1,6]naphthyridine hydrochloride.

12-N,N-dimethylaminothiocarbonyl-5,6,8a,9,10,11,12,12a,13,13a-decahydro-8H-isoquino[2,1-g][1,6]-naphthyridine hydrochloride;

3-methoxy-12-N,N-dimethylaminothiocarbonyl-5,6,8aα,9,10,11,12,12aα,13,13aα-decahydro-8H-isoquino[2,1-g][1,6]naphthyridine hydrochloride;

2,3-methylenedioxy-12-N,N-dimethylaminothiocarbonyl-5,6,8aα,9,10,11,12,12aα,13,13aα-decahydro-8H-isoquino[2,1-g][1,6]naphthyridine hydrochloride;

3-methyl-12-N,N-dimethylaminothiocarbonyl-5,6,8aα,9,10,11,12,12aα,13,13aα-decahydro-8H-isoquino[2,1-g][1,6]naphthyridine hydrochloride; and 2,3-dimethoxy-12-N,N-dimethylaminothiocarbonyl-5,6,8aα,9,10,11,12,12aα,13,13aα-decahydro-8H-isoquino[2,1-g][1,6]naphthyridine hydrochloride.

EXAMPLE 2

Preparation of
(8aR,12aS,13aS)-12-Benzylaminocarbonyl-5,6,8a,9,10,11,12,12a,13,13a-decahydro-8H-isoquino[2,1-g][1,6]naphthyridine hydrochloride and Related Compounds of Formula (1) and (2) wherein Z is —NHR$^4$ A. A solution of 115 mg of (8aR,12aS,13aS)-5,6,8a,9,10,11,12,12a,13,13a-decahydro-8H-isoquino[2,1-g][1,6]naphthyridine (VIIA) in 15 ml of toluene was stirred at room temperature and 50 µl of benzyl isocyanate was added. The mixture was stirred at room temperature for 16 hours, then solvent removed under reduced pressure. The residue was dissolved in chloroform, acidified with ethanolic HCl and concentrated to a foam. This foam was crystallized from ethanol/diethylether to give
(8aR,12aS,13aS)-12-benzylaminocarbonyl-5,6,8a,9,10,11,12,12a,13,13a-decahydro-8H-isoquino[2,1-g][1,6]naphthyridine hydrochloride, mp 184°–186° C., $[\alpha]_D^{25} = +64$ (C=0.0106, MeOH);

B. Similarly, optionally replacing (8aR,12aS,13aS)-5,6,8a,9,10,11,12,12a,13,13a-decahydro-8H-isoquino[2,1-g][1,6]naphthyridine with the appropriate compound of formula (VII), (VIII) or (VIIA) and optionally replacing benzylisocyanate with other isocyanates or isothiocyanates of formula R$^4$NCW, where W and R$^4$ are as defined supra, and following the procedure in paragraph A above, the following compounds of formula (1) and (2) were prepared:

(±)-12-isopropylaminocarbonyl-5,6,8aα,9,10,11,12,12aα,13,13aα-decahydro-8H-isoquino[2,1-g][1,6]naphthyridine hydrochloride, m.p. 155°–157° C.;

(±)-12-n-butylaminocarbonyl-5,6,8aα,9,10,11,12,12aα,13,13aα-decahydro-8H-isoquino[2,1-g][1,6]naphthyridine hydrochloride, m.p. 125°–126° C.;

(±)-12-t-butylaminocarbonyl-5,6,8aα,9,10,11,12,12aα,13,13aα-decahydro-8H-isoquino[2,1-g][1,6]naphthyridine hydrochloride, m.p. 217°–218° C.; and (8aR,12aS,13aS)-3-methoxy-12-phenylaminocarbonyl-5,6,8a,9,10,11,12,12a,13,13a-decahydro-8H-isoquino[2,1-g][1,6]naphthyridine hydrochloride, mp 264°–266° C., $[\alpha]_D^{25} = +121$ (C=1.0, DMSO).

C. The following compounds of formula (1) were prepared as shown in Preparation 5, where they are identified as compounds of formula (XI) and (XII).

(8aR,12aS,13aS)-12-[(R)-(+)-1-phenylethylamino]carbonyl-5,6,8a,9,10,11,12,12a,13,13a-decahydro-8H-isoquino[2,1-g][1,6]naphthyridine hydrochloride, mp 211°–212° C., $[\alpha]_D^{25} = +86.33$ (C=0.0053, MeOH);

(8aS,12aR,13aR)-12-[(R)-(+)-1-phenylethylamino]carbonyl-5,6,8a,9,10,11,12,12a,13,13a-decahydro-8H-isoquino[2,1-g][1,6]naphthyridine hydrochloride, mp 193°–194° C., $[\alpha]_D^{25} = +58.86$ (C=0.01055, MeOH); and (8aR,12aS,13aS)-3-methoxy-12-[(R) (+)-1-phenylethylamino]carbonyl-5,6,8a,9,10,11,12,12a,13,13a-decahydro-8H-isoquino[2,1-g][1,6]naphthyridine hydrochloride, mp 180°–182° C., $[\alpha]_D^{25} = +73.5$ (C=0.4, MeOH).

D. Similarly, optionally replacing (8aR,12aS,13aS)-5,6,8a,9,10,11,12,12a,13,13a-decahydro-8H-isoquino[2,1-g][1,6]naphthyridine with the appropriate compound of formula (VII), (VIII), (VIIA), (VIIB), (VIIIA) or (VIIIB), optionally replacing benzyl isocyanate with other isocyanates or isothiocyanates of formula R⁴NCW, where W and R⁴ are as defined supra, and following the procedure in paragraph A above, the following exemplary compounds of formula (1) and (2) are prepared. It should be understood that for the sake of brevity each name is intended to identify both of the individual enantiomers of a racemic mixture and the racemic mixture itself, obtained depending upon the starting material employed.

12-ethylaminocarbonyl-5,6,8aα,9,10,11,12,12aα,13,-13aα-decahydro-8H-isoquino[2,1-g][1,6]naphthyridine hydrochloride;

12-ethylaminocarbonyl-5,6,8aβ,9,10,11,12,12aβ,13,-13aα-decahydro-8H-isoquino[2,1-g][1,6]naphthyridine hydrochloride;

12-n-butylaminocarbonyl-5,6,8aα,9,10,11,12,12aα,13,-13aα-decahydro-8H-isoquino[2,1-g][1,6]naphthyridine hydrochloride;

12-n-butylaminocarbonyl-5,6,8aβ,9,10,11,12,12aβ,13,-13aα-decahydro-8H-isoquino[2,1-g][1,6]naphthyridine hydrochloride;

12-n-octylaminocarbonyl-5,6,8aα,9,10,11,12,12aα,13,-13aα-decahydro-8H-isoquino[2,1-g][1,6]naphthyridine hydrochloride;

12-n-octylaminocarbonyl-5,6,8aβ,9,10,11,12,12aβ,13,-13aα-decahydro-8H-isoquino[2,1-g][1,6]naphthyridine hydrochloride;

12-phenylaminocarbonyl-5,6,8aα,9,10,11,12,12aα,13,-13aα-decahydro-8H-isoquino[2,1-g][1,6]naphthyridine hydrochloride;

12-phenylaminocarbonyl-5,6,8aβ,9,10,11,12,12aβ,13,-13aα-decahydro-8H-isoquino[2,1-g][1,6]naphthyridine hydrochloride;

3-methoxy-12-ethylaminocarbonyl-5,6,8aα,9,10,11,12,-12aα,13,13aα-decahydro-8H-isoquino[2,1-g][1,6]naphthyridine hydrochloride;

3-methoxy-12-ethylaminocarbonyl-5,6,8aβ,9,10,11,12,-12aβ,13,13aα-decahydro-8H-isoquino[2,1-g][1,6]naphthyridine hydrochloride;

3-methoxy-12-n-butylaminocarbonyl-5,6,8aα,9,10,11,12,12aα,13,13aα-decahydro-8H-isoquino[2,1-g][1,6]naphthyridine hydrochloride;

3-methoxy-12-n-butylaminocarbonyl-5,6,8aβ,9,10,11,12,12aβ,13,13aα-decahydro-8H-isoquino[2,1-g][1,6]naphthyridine hydrochloride;

3-methoxy-12-n-octylaminocarbonyl-5,6,8aα,9,10,11,12,12aα,13,13aα-decahydro-8H-isoquino[2,1-g][1,6]naphthyridine hydrochloride;

3-methoxy-12-n-octylaminocarbonyl-5,6,8aβ,9,10,11,12,12aβ,13,13aα-decahydro-8H-isoquino[2,1-g][1,6]naphthyridine hydrochloride;

3-methoxy-12-phenylaminocarbonyl-5,6,8aα,9,10,11,12,12aα,13,13aα-decahydro-8H-isoquino[2,1-g][1,6]naphthyridine hydrochloride;

3-methoxy-12-phenylaminocarbonyl-5,6,8aβ,9,10,11,12,12aβ,13,13aα-decahydro-8H-isoquino[2,1-g][1,6]naphthyridine hydrochloride;

2,3-methylenedioxy-12-ethylaminocarbonyl-5,6,8aα,9,10,11,12,12aα,13,13aα-decahydro-8H-isoquino[2,1-g][1,6]naphthyridine hydrochloride;

2,3-methylenedioxy-12-ethylaminocarbonyl-5,6,8aβ,9,10,11,12,12aβ,13,13aα-decahydro-8H-isoquino[2,1-g][1,6]naphthyridine hydrochloride;

2,3-methylenedioxy-12-n-butylaminocarbonyl-5,6,8aα,9,10,11,12,12aα,13,13aα-decahydro-8H-isoquino[2,1-g][1,6]naphthyridine hydrochloride;

2,3-methylenedioxy-12-n-butylaminocarbonyl-5,6,8aβ,9,10,11,12,12aβ,13,13aα-decahydro-8H-isoquino[2,1-g][1,6]naphthyridine hydrochloride;

2,3-methylenedioxy-12-n-octylaminocarbonyl-5,6,8aα,9,10,11,12,12aα,13,13aα-decahydro-8H-isoquino[2,1-g][1,6]naphthyridine hydrochloride;

2,3-methylenedioxy-12-n-octylaminocarbonyl-5,6,8aβ,9,10,11,12,12aβ,13,13aα-decahydro-8H-isoquino[2,1-g][1,6]naphthyridine hydrochloride;

2,3-methylenedioxy-12-phenylaminocarbonyl-5,6,8aα,9,10,11,12,12aα,13,13aα-decahydro-8H-isoquino[2,1-g][1,6]naphthyridine hydrochloride;

2,3-methylenedioxy-12-phenylaminocarbonyl-5,6,8aβ,9,10,11,12,12aβ,13,13aα-decahydro-8H-isoquino[2,1-g][1,6]naphthyridine hydrochloride;

2,3-methylenedioxy-12-benzylaminocarbonyl-5,6,8aα,9,10,11,12,12aα,13,13aα-decahydro-8H-isoquino[2,1-g][1,6]naphthyridine hydrochloride;

2,3-methylenedioxy-12-benzylaminocarbonyl-5,6,8aβ,9,10,11,12,12aβ,13,13aα-decahydro-8H-isoquino[2,1-g][1,6]naphthyridine hydrochloride;

2-methyl-12-benzylaminocarbonyl-5,6,8aα,9,10,11,12,-12aα,13,13aα-decahydro-8H-isoquino[2,1-g][1,6]naphthyridine hydrochloride;

2-methyl-12-benzylaminocarbonyl-5,6,8aβ,9,10,11,12,-12aβ,13,13aα-decahydro-8H-isoquino[2,1-g][1,6]naphthyridine hydrochloride;

3-methyl-12-benzylaminocarbonyl-5,6,8aα,9,10,11,12,-12aα,13,13aα-decahydro-8H-isoquino[2,1-g][1,6]naphthyridine hydrochloride;

3-methyl-12-benzylaminocarbonyl-5,6,8aβ,9,10,11,12,-12aβ,13,13aα-decahydro-8H-isoquino[2,1-g][1,6]naphthyridine hydrochloride;

2,3-dimethyl-12-benzylaminocarbonyl-5,6,8aα,9,10,11,12,12aα,13,13aα-decahydro-8H-isoquino[2,1-g][1,6]naphthyridine hydrochloride;

2,3-dimethyl-12-benzylaminocarbonyl-5,6,8aβ,9,10,11,12,12aβ,13,13aα-decahydro-8H-isoquino[2,1-g][1,6]naphthyridine hydrochloride;

3-n-hexyl-12-benzylaminocarbonyl-5,6,8aα,9,10,11,12,-12aα,13,13aα-decahydro-8H-isoquino[2,1-g][1,6]naphthyridine hydrochloride;

3-n-hexyl-12-benzylaminocarbonyl-5,6,8aβ,9,10,11,12,-12aβ,13,13aα-decahydro-8H-isoquino[2,1-g][1,6]naphthyridine hydrochloride;

2-methoxy-12-benzylaminocarbonyl-5,6,8aα,9,10,11,12,12aα,13,13aα-decahydro-8H-isoquino[2,1-g][1,6]naphthyridine hydrochloride;

2-methoxy-12-benzylaminocarbonyl-5,6,8aβ,9,10,11,12,12aβ,13,13aα-decahydro-8H-isoquino[2,1-g][1,6]naphthyridine hydrochloride;

3-ethoxy-12-benzylaminocarbonyl-5,6,8aα,9,10,11,12,-12aα,13,13aα-decahydro-8H-isoquino[2,1-g][1,6]naphthyridine hydrochloride;

3-ethoxy-12-benzylaminocarbonyl-5,6,8aβ,9,10,11,12,-12aβ,13,13aα-decahydro-8H-isoquino[2,1-g][1,6]naphthyridine hydrochloride;

3-n-hexyloxy-12-benzylaminocarbonyl-5,6,8aα,9,10,11,12,12aα,13,13aα-decahydro-8H-isoquino[2,1-g][1,6]naphthyridine hydrochloride;

3-n-hexyloxy-12-benzylaminocarbonyl-5,6,8aβ,9,10,11,12,12aβ,13,13aα-decahydro-8H-isoquino[2,1-g][1,6]naphthyridine hydrochloride;

3-hydroxy-12-benzylaminocarbonyl-5,6,8aα,9,10,11,12,12aα,13,13aα-decahydro-8H-isoquino[2,1-g][1,6]naphthyridine hydrochloride;
3-hydroxy-12-benzylaminocarbonyl-5,6,8aβ,9,10,11,12,12aβ,13,13aα-decahydro-8H-isoquino[2,1-g][1,6]naphthyridine hydrochloride;
2,3-dimethox-12-benzylaminocarbonyl-5,6,8aα,9,10,11,12,12aα,13,13aα-decahydro-8H-isoquino[2,1-g][1,6]naphthyridine hydrochloride;
2,3-dimethoxy-12-benzylaminocarbonyl-5,6,8aβ,9,10,11,12,12aβ,13,13aα-decahydro-8H-isoquino[2,1-g][1,6]naphthyridine hydrochloride;
3,4-methylenedioxy-12-benzylaminocarbonyl-5,6,8aα,9,10,11,12,12aα,13,13aα-decahydro-8H-isoquino[2,1-g][1,6]naphthyridine hydrochloride;
3,4-methylenedioxy-12-benzylaminocarbonyl-5,6,8aβ,9,10,11,12,12aβ,13,13aα-decahydro-8H-isoquino[2,1-g][1,6]naphthyridine hydrochloride;
3-chloro-12-benzylaminocarbonyl-5,6,8aα,9,10,11,12,-12aα,13,13aα-decahydro-8H-isoquino[2,1-g][1,6]naphthyridine hydrochloride;
3-chloro-12-benzylaminocarbonyl-5,6,8aβ,9,10,11,12,-12aβ,13,13aα-decahydro-8H-isoquino[2,1-g][1,6]naphthyridine hydrochloride;
3-fluoro-12-benzylaminocarbonyl-5,6,8aα,9,10,11,12,-12aα,13,13aα-decahydro-8H-isoquino[2,1-g][1,6]naphthyridine hydrochloride;
3-fluoro-12-benzylaminocarbonyl-5,6,8aβ,9,10,11,12,-12aβ,13,13aα-decahydro-8H-isoquino[2,1-g][1,6]naphthyridine hydrochloride;
12-benzylaminothiocarbonyl-5,6,8aβ,9,10,11,12,-12aβ,13,13aα-decahydro-8H-isoquino[2,1-g][1,6]naphthyridine hydrochloride;
12-isopropylaminothiocarbonyl-5,6,8aα,9,10,11,12,-12aα,13,13aα-decahydro-8H-isoquino[2,1-g][1,6]naphthyridine hydrochloride;
12-n-butylaminothiocarbonyl-5,6,8aα,9,10,11,12,-12aα,13,13aα-decahydro-8H-isoquino[2,1-g][1,6]naphthyridine hydrochloride;
12-t-butylaminothiocarbonyl-5,6,8aα,9,10,11,12,-12aα,13,13aα-decahydro-8H-isoquino[2,1-g][1,6]naphthyridine hydrochloride; and
3-methoxy-12-phenylaminothiocarbonyl-5,6,8aα,9,10,11,12,12aα,13,13aα-decahydro-8H-isoquino[2,1-g][1,6]naphthyridine hydrochloride.

EXAMPLE 3

Preparation of (±)-12-aminocarbonyl-5,6,8aα,9,10,11,12,12aα,13,-13aα-decahydro-8H-isoquino[2,1-g][1,6]naphthyridine hydrochloride and Related Compounds of Formula (1) and (2) where Z is —NH₂

A. A mixture of 600 mg of (±)-5,6,8aα,9,10,11,12,-12aα,13,13aα-decahydro-8H-isoquino[2,1-g][1,6]naphthyridine (VII), 750 mg of potassium isocyanate in 3 ml of water and 4 ml of acetic acid was heated on a steam bath for 1 hour. To the reaction mixture was added 100 ml of ethyl acetate, and the organic layer was separated and dried over anhydrous magnesium sulfate. The solvent was removed under reduced pressure, and the residue chromatographed on silica gel, eluting with 0.5% methanol/methylene chloride. The product was dissolved in diethylether and acidified with ethanolic HCl. The solvent was removed under reduced pressure and the residue crystallized from ethanol/diethylether mixture, to give (±)-12-aminocarbonyl-5,6,8aα,9,10,11,12,12aα,13,-13aα-decahydro-8H-isoquino[2,1-g][1,6]naphthyridine hydrochloride, m.p. 185°–188° C.

B. Similarly, replacing (±)-5,6,8aα,9,10,11,12,-12aα,13,13aα-decahydro-8H-isoquino[2,1-g][1,6]naphthyridine with the appropriate compound of formula (VII), (VIII), (VIIA), (VIIB), (VIIIA) or (VIIIB) and following the procedure in paragraph A above, the following compounds of formula (1) or (2) are prepared:
3-methoxy-12-aminocarbonyl-5,6,8aα,9,10,11,12,-12aα,13,13aα-decahydro-8H-isoquino[2,1-g][1,6]naphthyridine hydrochloride;
2,3-methylenedioxy-12-aminocarbonyl-5,6,8aα,9,10,11,12,12aα,13,13aα-decahydro-8H-isoquino[2,1-g][1,6]naphthyridine hydrochloride;
2-methyl-12-aminocarbonyl-5,6,8aα,9,10,11,12,-12aα,13,13aα-decahydro-8H-isoquino[2,1-g][1,6]naphthyridine hydrochloride;
2,3-dimethyl-12-aminocarbonyl-5,6,8aα,9,10,11,12,-12aα,13,13aα-decahydro-8H-isoquino[2,1-g][1,6]naphthyridine hydrochloride;
3-n-hexyl-12-aminocarbonyl-5,6,8aα,9,10,11,12,-12aα,13,13aα-decahydro-8H-isoquino[2,1-g][1,6]naphthyridine hydrochloride;
2-methoxy-12-N,N-aminocarbonyl-5,6,8aα,9,10,11,12,-12aα,13,13aα-decahydro-8H-isoquino[2,1-g][1,6]naphthyridine hydrochloride;
3-ethoxy-12-aminocarbonyl-5,6,8aα,9,10,11,12,-12aα,13,13aα-decahydro-8H-isoquino[2,1-g][1,6]naphthyridine hydrochloride;
3-n-hexyloxy-12-aminocarbonyl-5,6,8aα,9,10,11,12,-12aα,13,13aα-decahydro-8H-isoquino[2,1-g][1,6]naphthyridine hydrochloride;
3-hydroxy-12-aminocarbonyl-5,6,8aα,9,10,11,12,-12aα,13,13aα-decahydro-8H-isoquino[2,1-g][1,6]naphthyridine hydrochloride;
2,3-dimethoxy-12-aminocarbonyl-5,6,8aα,9,10,11,12,-12aα,13,13aα-decahydro-8H-isoquino[2,1-g][1,6]naphthyridine hydrochloride;
3,4-methylenedioxy-12aminocarbonyl-5,6,8aα,9,10,11,12,12aα,13,13aα-decahydro-8H-isoquino[2,1-g][1,6]naphthyridine hydrochloride;
3-chloro-12-aminocarbonyl-5,6,8aα,9,10,11,12,12aα,13,-13aα-decahydro-8H-isoquino[2,1-g][1,6]naphthyridine hydrochloride; and
3-fluoro-12-aminocarbonyl-5,6,8aα,9,10,11,12,12aα,13,-13aα-decahydro-8H-isoquino[2,1-g][1,6]naphthyridine hydrochloride.

EXAMPLE 4

Preparation of (±)-12-Methoxycarbonyl-5,6,8aα,9,10,11,12,12aα,13,-13aα-decahydro-8H-isoquino[2,1-g][1,6]naphthyridine hydrochloride and Related Compounds of Formula (1) and (2) where Z is —OR²

A. A mixture of 440 mg of (±)-5,6,8aα,9,10,11,12,-12aα,13,13aα-decahydro-8H-isoquino[2,1-g][1,6]naphthyridine (VII), 424 mg of sodium carbonate and 0.26 ml of methyl chloroformate in 20 ml of water and 25 ml of toluene was stirred at room temperature for 15 hours. To the reaction mixture was added 100 ml of ethyl acetate, and the organic layer was separated and dried over anhydrous magnesium sulfate. The solvent was removed under reduced pressure, and the residue chromatographed on silica gel, eluting with 0.5% methanol/methylene chloride. The product was dissolved in diethylether and a:solidified with ethanolic HCl. The solvent was removed under reduced pressure and the residue crystallized from ethanol/diethylether mixture, to give (±)-12-methoxycarbonyl-5,6,8aα,9,10,11,12,-12aα,13,13aα-decahydro-8H-isoquino[2,1-g][1,6]naphthyridine hydrochloride, m.p. 230–232.

B. Similarly, replacing methyl chloroformate with other chloroformates of formula $R^2OC(O)Cl$, where $R^2$ is as defined supra, and following the procedure in paragraph A above, the following compounds of formula (1) were prepared:

(±)-12-(2-methylprop-1-oxy)carbonyl-5,6,8aα,9,10,11,12,12aα,13,13aα-decahydro-8H-isoquino[2,1-g][1,6]naphthyridine hydrochloride, m.p. 178–180; and (±)-12-benzyloxycarbonyl-5,6,8aα,9,10,11,12,12aα,13,-13aα-decahydro8H-isoquino[2,1-g][1,6]naphthyridine hydrochloride, m.p. 19714 199.

C. Similarly, optionally replacing (±)-5,6,8aα,9,10,11,12,12aα,13,13aα-decahydro-8H-isoquino[2,1-g][1,6]naphthyridine with the appropriate compound of formula (VII), (VIII), (VIIA), (VIIB), (VIIIA) or (VIIIB), optionally replacing methyl chloroformate with other chloroformates or chlorothionoformates of formula $R^2OC(W)Cl$, where W and $R^2$ are as defined supra, and following the procedure in paragraph A above, the following exemplary compounds of formula (1) and (2) are prepared. It should be understood that for the sake of brevity each name is intended to identify both of the individual enantiomers of a racemic mixture and the racemic mixture itself, all of which may be obtained by the above procedure depending upon the starting material employed.

12-ethoxycarbonyl-5,6,8aα,9,10,11,12,12aα,13,13aα-decahydro-8H-isoquino[2,1-g][1,6]naphthyridine hydrochloride;

12-ethoxycarbonyl-5,6,8aα,9,10,11,12,12aα,13,13aα-decahydro-8H-isoquino[2,1-g][1,6]naphthyridine hydrochloride;

12-n-butoxycarbonyl-5,6,8aα,9,10,11,12,12aα,13,13aα-decahydro-8H-isoquino[2,1-g][1,6]naphthyridine hydrochloride;

12-n-butoxycarbonyl-5,6,8aβ,9,10,11,12,12aβ,13,13aα-decahydro-8H-isoquino[2,1-g][1,6]naphthyridine hydrochloride;

12-n-hexyloxycarbonyl-5,6,8aα,9,10,11,12,12aα,13,-13aα-decahydro-8H-isoquino[2,1-g][1,6]naphthyridine hydrochloride;

12-n-hexyloxycarbonyl-5,6,8aβ,9,10,11,12,12aβ,13,-13aα-decahydro-8H-isoquino[2,1-g][1,6]naphthyridine hydrochloride;

12-phenoxycarbonyl-5,6,8aβ,9,10,11,12,12aβ,13,13aα-decahydro-8H-isoquino[2,1-g][1,6]naphthyridine hydrochloride;

12-phenoxycarbonyl-5,6,8aβ,9,10,11,12,12aβ,13,13aα-decahydro-8H-isoquino[2,1-g][1,6]naphthyridine hydrochloride;

3-methoxy-12-methoxycarbonyl-5,6,8aα,9,10,11,12,-12aα,13,13aα-decahydro-8H-isoquino[2,1-g][1,6]naphthyridine hydrochloride;

3-methoxy-12-methoxycarbonyl-5,6,8aβ,9,10,11,12,-12aβ,13,13aα-decahydro-8H-isoquino[2,1-g][1,6]naphthyridine hydrochloride;

3-methoxy-12-ethoxycarbonyl-5,6,8aα,9,10,11,12,-12aα,13,13aα-decahydro-8H-isoquino[2,1-g][1,6]naphthyridine hydrochloride;

3-methoxy-12-ethoxycarbonyl-5,6,8aβ,9,10,11,12,-12aβ,13,13aα-decahydro-8H-isoquino[2,1-g][1,6]naphthyridine hydrochloride;

3-methoxy-12-n-butoxycarbonyl-5,6,8aα,9,10,11,12,-12aα,13,13aα-decahydro-8H-isoquino[2,1-g][1,6]naphthyridine hydrochloride;

3-methoxy-12-n-butoxycarbonyl-5,6,8aβ,9,10,11,12,-12aβ,13,13aα-decahydro-8H-isoquino[2,1-g][1,6]naphthyridine hydrochloride;

3-methoxy-12-n-hexyloxycarbonyl-5,6,8aα,9,10,11,12,-12aα,13,13aα-decahydro-8H-isoquino[2,1-g][1,6]naphthyridine hydrochloride;

3-methoxy-12-n-hexyloxycarbonyl-5,6,8aβ,9,10,11,12,-12aβ,13,13aα-decahydro-8H-isoquino[2,1-g][1,6]naphthyridine hydrochloride;

3-methoxy-12-phenoxycarbonyl-5,6,8aα,9,10,11,12,-12aα,13,13aα-decahydro-8H-isoquino[2,1-g][1,6]naphthyridine hydrochloride;

3-methoxy-12-phenoxycarbonyl-5,6,8aβ,9 11,12,12aβ,13,13aα-decahydro-8H-isoquino[2,1-g][1,6]naphthyridine hydrochloride;

3-methoxy-12-benzyloxycarbonyl-5,6,8aα,9,10,11,12,-12aα,13,13aα-decahydro-8H-isoquino[2,1-g][1,6]naphthyridine hydrochloride;

3-methoxy-12-benzyloxycarbonyl-5,6,8aβ,9,10,11,12,-12aβ,13,13aα-decahydro-8H-isoquino[2,1-g][1,6]naphthyridine hydrochloride;

2,3-methylenedioxy-12-methoxycarbonyl-5,6,8aα,9,10,11,12,12aα,13,13aα-decahydro-8H-isoquino[2,1-g][1,6]naphthyridine hydrochloride;

2,3-methylenedioxy-12-methoxycarbonyl-5,6,8aβ,9,10,11,12,12aβ,13,13aα-decahydro-8H-isoquino[2,1-g][1,6]naphthyridine hydrochloride;

2,3-methylenedioxy-12-ethoxycarbonyl-5,6,8aα,9,10,11,12,12aα,13,13aα-decahydro-8H-isoquino[2,1-g][1,6]naphthyridine hydrochloride;

2,3-methylenedioxy-12-ethoxycarbonyl-5,6,8aβ,9,10,11,12,12aβ,13,13aα-decahydro-8H-isoquino[2,1-g][1,6]naphthyridine hydrochloride;

2,3-methylenedioxy-12-n-butoxycarbonyl-5,6,8aα,9,10,11,12,12aα,13,13aα-decahydro-8H-isoquino[2,1-g][1,6]naphthyridine hydrochloride;

2,3-methylenedioxy-12-n-butoxycarbonyl-5,6,8aβ,9,10,11,12,12aβ,13,13aα-decahydro-8H-isoquino[2,1-g][1,6]naphthyridine hydrochloride;

2,3-methylenedioxy-12-n-hexyloxycarbonyl-5,6,8aα,9,10,11,12,12aα,13,13aα-decahydro-8H-isoquino[2,1-g][1,6]naphthyridine hydrochloride;

2,3-methylenedioxy-12-n-hexyloxycarbonyl-5,6,8aβ,9,10,11,12,12aβ,13,13aα-decahydro-8H-isoquino[2,1-g][1,6]naphthyridine hydrochloride;

2,3-methylenedioxy-12-phenoxycarbonyl-5,6,8aα,9,10,11,12,12aα,13,13aα-decahydro-8H-isoquino[2,1-g][1,6]naphthyridine hydrochloride;

2,3-methylenedioxy-12-phenoxycarbonyl-5,6,8aβ,9,10,11,12,12aβ,13,13aα-decahydro-8H-isoquino[2,1-g][1,6]naphthyridine hydrochloride;

2,3-methylenedioxy-12-benzyloxycarbonyl-5,6,8aα,9,10,11,12,12aα,13,13aα-decahydro-8H-isoquino[2,1-g][1,6]naphthyridine hydrochloride;

2,3-methylenedioxy-12-benzyloxycarbonyl-5,6,8aβ,9,10,11,12,12aβ,13,13aα-decahydro-8H-isoquino[2,1-g][1,6]naphthyridine hydrochloride;

2-methyl-12-methoxycarbonyl-5,6,8aα,9,10,11,12,-12aα,13,13aα-decahydro-8H-isoquino[2,1-g][1,6]naphthyridine hydrochloride;

2-methyl-12-methoxycarbonyl-5,6,8aβ,9,10,11,12,-12aβ,13,13aα-decahydro-8H-isoquino[2,1-g][1,6]naphthyridine hydrochloride;

3-methyl-12-methoxycarbonyl-5,6,8aα,9,10,11,12,-12aα,13,13aα-decahydro-8H-isoquino[2,1-g][1,6]naphthyridine hydrochloride;
3-methyl-12-methoxycarbonyl-5,6,8aβ,9,10,11,12,-12aβ,13,13aα-decahydro-8H-isoquino[2,1-g][1,6]naphthyridine hydrochloride;
2,3-dimethyl-12-methoxycarbonyl-5,6,8aα,9,10,11,12,-12aα,13,13aα-decahydro-8H-isoquino[2,1-g][1,6]naphthyridine hydrochloride;
2,3-dimethyl-12-methoxycarbonyl-5,6,8aβ,9,10,11,12,-12aβ,13,13aα-decahydro-8H-isoquino[2,1-g][1,6]naphthyridine hydrochloride;
3-n-hexyl-12-methoxycarbonyl-5,6,8aα,9,10,11,12,-12aα,13,13aα-decahydro-8H-isoquino[2,1-g][1,6]naphthyridine hydrochloride;
3-n-hexyl-12-methoxycarbonyl-5,6,8aβ,9,10,11,12,-12aβ,13,13aα-decahydro-8H-isoquino[2,1-g][1,6]naphthyridine hydrochloride;
2-methoxy-12-methoxycarbonyl-5,6,8aα,9,10,11,12,-12aα,13,13aα-decahydro-8H-isoquino[2,1-g][1,6]naphthyridine hydrochloride;
2-methoxy-12-methoxycarbonyl-5 6,8aβ,9,10,11,12,-12aβ,13,13aα-decahydro-8H-isoquino[2,1-g][1,6]-naphthyridine hydrochloride;
3-ethoxy-12-methoxycarbonyl-5,6,8aα,9,10,11,12,-12aα,13,13aα-decahydro-8H-isoquino[2,1-g][1,6]naphthyridine hydrochloride;
3-ethoxy-12-methoxycarbonyl-5,6,8aβ,9,10,11,12,-12aβ,13,13aα-decahydro-8H-isoquino[2,1-g][1,6]naphthyridine hydrochloride;
3-n-hexyloxy-12-methoxycarbonyl-5,6,8aα,9,10,11,12,-12aα,13,13aα-decahydro-8H-isoquino[2,1-g][1,6]naphthyridine hydrochloride;
3-n-hexyloxy-12-methoxycarbonyl-5,6,8aβ,9,10,11,12,-12aβ,13,13aα-decahydro-8H-isoquino[2,1-g][1,6]naphthyridine hydrochloride;
3-hydroxy-12-methoxycarbonyl-5,6,8aα,9,10,11,12,-12aα,13,13aα-decahydro-8H-isoquino[2,1-g][1,6]naphthyridine hydrochloride;
3-hydroxy-12-methoxycarbonyl-5,6,8aβ,9,10,11,12,-12aβ,13,13aα-decahydro-8H-isoquino[2,1-g][1,6]naphthyridine hydrochloride;
2,3-dimethoxy-12-methoxycarbonyl-5,6,8aα,9,10,11,12,12aα,13,13aα-decahydro-8H-isoquino[2,1-g][1,6]naphthyridine hydrochloride;
2,3-dimethoxy-12-methoxycarbonyl-5,6,8aβ,9,10,11,12,12aβ,13,13aα-decahydro-8H-isoquino[2,1-g][1,6]naphthyridine hydrochloride;
3,4-methylenedioxy-12-methoxycarbonyl-5,6,8aα,-9,10,11,12,12aα,13,13aα-decahydro-8H-isoquino[2,1-g][1,6]naphthyridine hydrochloride;
3,4-methylenedioxy-12-methoxycarbonyl-5,6,8aβ,9,10,11,12,12aβ,13,13aα-decahydro-8H-isoquino[2,1-g][1,6]naphthyridine hydrochloride;
3-chloro-12-methoxycarbonyl-5,6,8aα,9,10,11,12,-12aα,13,13aα-decahydro-8H-isoquino[2,1-g][1,6]naphthyridine hydrochloride;
3-chloro-12-methoxycarbonyl-5,6,8aβ,9,10,11,12,-12aβ,13,13aα-decahydro-8H-isoquino[2,1-g][1,69-naphthyridine hydrochloride;
3-fluoro-12-methoxycarbonyl-5,6,8aα,9,10,11,12,-12aα,13,13aα-decahydro-8H-isoquino[2,1-g][1,6]naphthyridine hydrochloride; and
3-fluoro-12-methoxycarbonyl-5,6,8aβ,9,10,11,12,-12aβ,13,13aα-decahydro-8H-isoquino[2,1-g][1,6]naphthyridine hydrochloride.

12-methoxythiocarbonyl-5,6,8aα,9,10,11,12,12aα,13,-13aα-decahydro-8H-isoquino[2,1-g][1,6]naphthyridine hydrochloride;
12-(2-methylprop-1-oxy)thiocarbonyl-5,6,8aα,9,10,11,12,12aα,13,13aα-decahydro-8H-isoquino[2,1-g][1,6]naphthyridine hydrochloride;
12-benzyloxythiocarbonyl-5,6,8aα,9,10,11,12,12aα,13,-13aα-decahydro-8H-isoquino[2,1-g][1,6]naphthyridine hydrochloride;
3-methoxy-12-benzyloxythiocarbonyl-5,6,8aα,9,10,11,12,12aα,13,13aα-decahydro-8H-isoquino[2,1-g][1,6]naphthyridine hydrochloride;
2,3-dimethoxy-12-benzyloxythiocarbonyl-5,6,8aα,9,10,11,12,12aα,13,13aα-decahydro-8H-isoquino[2,1-g][1,6]naphthyridine hydrochloride; and
2,3-methylenedioxy-12-benzyloxythiocarbonyl-5,6,8aα,9,10,11,12,12aα,13,13aα-decahydro-8H-isoquino[2,1-g][1,6]-naphthyridine hydrochloride.

EXAMPLE 5

Preparation of (8aR,12aS,13aS)-3-Methoxy-12-benzoyl-5,6,8a,9,10,11,12,12a,13,13a-decahydro-8H-isoquino[2,1-g][1,6]naphthyridine hydrochloride and Related Compounds of Formula (1) and (2) where Z is —$R^1$ A. To a mixture of 300 mg of (8aR,12aS,13aS)-3-methoxy-5,6,8a,9,10,11,12,12a,13,13a-decahydro-8H-isoquino[2,1-g][1,6]naphthyridine (VIIA) and 424 mg of sodium carbonate in 20 ml of water and 30 ml of toluene was added 0.162 ml of benzoyl chloride. The mixture was stirred at room temperature for 2 hours, and then diluted with 100 ml of ethyl acetate. The organic layer was separated and dried over anhydrous magnesium sulfate. The solvent was removed under reduced pressure, and the residue chromatographed on silica gel, eluting with 1.0% methanol/methylene chloride. The product was dissolved in diethylether and acidified with ethanolic HCl. The solvent was removed under reduced pressure and the residue crystallized from ethanol, to give
(8aR,12aS,13aS)-12-benzoyl-5,6,8a,9,10,11,12,-12a,13,13a-decahydro-8H-isoquino[2,1-g][1,6]naphthyridine hydrochloride,
mp 248°–250° C., $[\alpha]_D^{25} = +82$ (C=0.0139, MeOH);

B. Similarly, optionally replacing (±)-3-methoxy-5,6,8aα,9,10,11,12,12aα,13,13aα-decahydro-8H-isoquino[2,1-g][1,6]naphthyridine with the appropriate compound of formula (VII) or (VIIA) and optionally replacing benzoyl chloride with other acid chlorides of formula $R^1C(O)Cl$, where $R^1$ is as defined supra, and following the procedure in paragraph A above, the following compounds of formula (1) were prepared:
(±)-12-acetyl-5,6,8aα,9,10,11,12,12aα,13,13aα-decahydro-8H-isoquino[2,1-g][1,6]naphthyridine hydrochloride, m.p. 245–247;
(±)-3-methoxy-12-(2-methylpropanoyl)-5,6,8aα,9,10,11,12,12aα,13,13aα-decahydro-8H-isoquino[2,1-g][1,6]naphthyridine hydrochloride, m.p. 159–161;
(±)-3-methoxy-12-bromoacetyl-5,6,8aα,9,10,11,12,-12aα,13,13aα-decahydro-8H-isoquino[2,1-g][1,6]naphthyridine hydrochloride, m.p. 232–233;
(8aR,12aS,13aS)-3-methoxy-12-(2,2-dimethylpropanoyl-5,6,8a,9,10,11,12,12a,13,13a-decahydro-8H-isoquino[2,1-g][1,6]naphthyridine hydrochloride, mp 217°-219° C., $[\alpha]_D^{25} = +90.15$ (C=0.01056, MeOH) and;

(8aR,12aS,13aS)-3-methoxy-12-(furan-2-yl)formyl-5,6,8a,9,10,11,12,12a,13,13a-decahydro-8H-isoquino[2,1-g][1,6]naphthyridine hydrochloride, mp 202°-204° C., $[\alpha]_D^{25} = +117.34$ (C=0.0094, MeOH).

C. Similarly, optionally replacing (8aR,12aS,13aS)-5,6,8a,9,10,11,12,12a,13,13a-decahydro-8H-isoquino[2,1-g][1,6]naphthyridine with the appropriate compound of formula (VII), (VIII), (VIIA), (VIIB), (VIIIA) or (VIIIB), optionally replacing benzoyl chloride with other acid chlorides of formula $R^1C(W)Cl$, where W and $R^1$ are as defined supra, and following the procedure in paragraph A above, the following exemplary compounds of formula (1) and (2) are prepared. It should be understood that for the sake of brevity each name is intended to identify both of the individual enantiomers of a racemic mixture and the racemic mixture itself, obtained depending upon the starting material employed.

12-propanoyl-5,6,8aα,9,10,11,12,12aα,13,13aα-decahydro-8H-isoquino[2,1-g][1,6]naphthyridine hydrochloride;

12-propanoyl-5,6,8aα,9,10,11,12,12aα,13,13aα-decahydro-8H-isoquino[2,1-g][1,6]naphthyridine hydrochloride;

12-(2,2-dimethylpropanoyl)-5,6,8aα,9,10,11,12,12aα,13,13aα-decahydro-8H-isoquino[2,1g-][1,6]napthyridine hydrochloride;

12-(2,2-dimethylpropanoyl)-5,6,8aβ8,9,10,11,12,-12aβ,13,13aβ-decahydro-8H-isoquino[2,1-g][1,6]-naphthyridine hydrochloride;

12-bromoacetyl-5,6,8aα,9,10,11,12,12aα,13,13aα-decahydro-8H-isoquino[2,1-g][1,6]naphthyridine hydrochloride;

12-bromoacetyl-5,6,8aβ,9,10,11,12,12aβ,13,13aα-decahydro-8H-isoquino[2,1-g][1,6]naphthyridine hydrochloride;

12-fluoroacetyl-5,6,8aα,9,10,11,12,12aα,13,13aα-decahydro-8H-isoquino[2,1-g][1,6]naphthyridine hydrochloride;

12-fluoroacetyl-5,6,8aβ,9,10,11,12,12aβ,13,13aα-decahydro-8H-isoquino[2,1-g][1,6]naphthyridine hydrochloride;

12-benzoyl-5,6,8aα,9,10,11,12,12aα,13,13aα-decahydro-8H-isoquino[2,1-g][1,6]naphthyridine hydrochloride;

12-benzoyl-5,6,8aβ,9,10,11,12,12aβ,13,13aβ-decahydro-8H-isoquino[2,1-g][1,6]naphthyridine hydrochloride;

3-methoxy-12-acetyl-5,6,8aα,9,10,11,12,12aα,13,13aα-decahydro-8H-isoquino[2,1-g][1,6]naphthyridine hydrochloride;

3-methoxy-12-acetyl-5,6,8aβ, 9,10,11,12,12aβ,13,13aα-decahydro-8H-isoquino[2,1-g][1,6]naphthyridine hydrochloride;

3-methoxy-12-propanoyl-5,6,8aα, 9,10,11,12,12,aα,13,13aα-decahydro-8H-isoquino[2,1-g][1,6]naphthyridine hydrochloride;

3-methoxy-12-propanoyl-5,6,8aβ, 9,10,11,12,12,aβ,13,13aα-decahydro-8H-isoquino[2,1-g][1,6]naphthyridine hydrochloride;

3-methoxy-12-fluoroacetyl-5,6,8aα,9,10,11,12,12aα,13,13aα-decahydro-8H-isoquino[2,1-g][1,6]naphthyridine hydrochloride;

3-methoxy-12-fluoroacetyl-5,6,8aβ,9,10,11,12,12aβ,13,13aα-decahydro-8H-isoquino[2,1-g][1,6]naphthyridine hydrochloride;

2,3-methylenedioxy-12-acetyl 5,6,8aα,9,10,11,12,12β,13,13aα-decahydro-8H isoquino[2,1-g][1,6]-naphthyridine hydrochloride;

2,3-methylenedioxy-12-acetyl-5,6,8aαβ,9,10,11,12,12β,13,13aα-decahydro-8H-isoquino[2,1-g][1,6]naphthyridine hydrochloride;

2,3-methylenedioxy-12-propanoyl-5,6,8aα,9,10,11,12,-12aα,13,13aα-decahydro 8H-isoquino[2,1-g][1,6]naphthyridine hydrochloride;

2,3-methylenedioxy-12-propanoyl-5,6,8aβ,9,10,11,12,-12aβ,13,13aα-decahydro-8H-isoquino[2,1-g][1,6]naphthyridine hydrochloride;

2,3-methylenedioxy-12-(2,2 dimethylpropanoyl)-5,6,8aα,9,10,11,12,12aα,13,13aα-decahydro-8H-isoquino[2,1-g][1,6]naphthyridine hydrochloride;

2,3-methylenedioxy-12-(2,2-dimethylpropanoyl)-5,6,8,β,9,10,11,12,12aβ,13,13aα-decahydro-8H-isoquino[2,1-g][1,6]naphthyridine hydrochloride;

2,3-methylenedioxy-12-bromoacetyl 5,6,8aα,9,10,11,12,12aα,13,13aα-decahydro 8H-isoquino[2,1-g][1,6]naphthyridine hydrochloride;

2,3-methylenedioxy 12-bromoacetyl-5,6,8aβ,9,10,11,12,12aα,13,13aα-decahydro-8H isoquino[2,1-g][1,6]naphthyridine hydrochloride;

2,3-methylenedioxy-12-fluoroacetyl-5,6,8aα,9,10,11,12,12aα,13,13aα-decahydro-8H-isoquino[2,1-g][1,6]naphthyridine hydrochloride;

2,3-methylenedioxy-12-fluoroacetyl-5,6,8aβ,9,10,11,12,12aβ,13,13aα-decahydro-8H-isoquino[2,1-g][1,6] naphthyridine hydrochloride;

2,3-methylenedioxy-12-benzoyl-5,6,8aα,9,10,11,12,-12aα,13,13aα-decahydro-8H-isoquino[2,1-g][1,6]naphthyridine hydrochloride;

2,3-methylenedioxy-12-benzoyl-5,6,8aα,9,10,11,12,-12aβ,13,13aα-decahydro-8H-isoquino[2,1-g][1,6]naphthyridine hydrochloride;

2-methyl-12-benzylaminocarbonyl-5,6,8aα,9,10,11,12,-12aα,13,13aα-decahydro-8H-isoquino[2,1-g][1,6]naphthyridine hydrochloride;

2-methyl-12-(2,2-dimethylpropanoyl)-5,6,8aβ,9,10,11,12,12aβ,13,13aα-decahydro-8H-isoquino[2,1-g][1,6]naphthyridine hydrochloride;

3-methyl-12-(2,2-dimethylpropanoyl)-5,6,8aα,9,10,11,12,12aα,13,13aα-decahydro-8H-isoquino[2,1-g][1,6]naphthyridine hydrochloride;

3-methyl-12-(2,2-dimethylpropanoyl)-5,6,8aβ,9,10,11,12,12aβ,13,13aα-decahydro-8H-isoquino[2,1-g][1,6]naphthyridine hydrochloride;

2,3-dimethyl-12-(2,2-dimethylpropanoyl)-5,6,8aα,9,10,11,12,12aα,13,13aα-decahydro-8H-isoquino[2,1-g][1,6]naphthyridine hydrochloride;

2,3-dimethyl-12-(2,2-dimethylpropanoyl)-5,6,8aβ,9,10,11,12,12aβ,13,13aα-decahydro-8H-isoquino[2,1-g][1,6]naphthyridine hydrochloride;

3-n-hexyl-12-(2,2-dimethylpropanoyl) 5,6,8aα,9,10,11,12,12aα,13,13aα-decahydro-8H-isoquino[2,1-g][1,6]naphthyridine hydrochloride;

3-n-hexyl-12-(2,2-dimethylpropanoyl) 5,6,8aβ,9,10,11,12,12aβ,13,13aα-decahydro-8H-isoquino[2,1-g][1,6]naphthyridine hydrochloride;

2-methoxy-12-(2,2-dimethylpropanoyl)-5,6,8aα,9,10,11,12,12aα,13,13aα-decahydro-8H-isoquino[2,1-g][1,6]naphthyridine hydrochloride, 2-methoxy-12-(2,2-dimethylpropanoyl)-5,6,8aβ, 9,10,11,12,12aβ,13,13aα-decahydro-8H-isoquino[2,1-g][1,6]naphthyridine hydrochloride;

3-ethoxy-12-(2,2-dimethylpropanoyl)-
  5,6,8aα,9,10,11,12,12aα,13,13aα-decahydro-8H-
  isoquino[2,1-g][1,6]naphthyridine hydrochloride;
3-ethoxy-12-(2,2-dimethylpropanoyl)-
  5,6,8aβ,9,10,11,12,12aβ,13,13aα-decahydro-8H-
  isoquino[2,1-g][1,6]naphthyridine hydrochloride;
3-n-hexyloxy-12-(2,2-dimethylpropanoyl)-
  5,6,8aα,9,10,11,12,12aα,13,13aα-decahydro 8H-
  isoquino[2,1-g][1,6]naphthyridine hydrochloride;
3-n-hexyloxy-12-(2,2-dimethylpropanoyl)-
  5,6,8aβ,9,10,11,12,12aβ,13,13aα-decahydro-8H-
  isoquino[2,1-g][1,6]naphthyridine hydrochloride;
3-hydroxy-12-(2,2-dimethylpropanoyl)-
  5,6,8aα,9,10,11,12,12aα,13,13aα-decahydro-8H-
  isoquino[2,1-g][1,6]naphthyridine hydrochloride;
3-hydroxy-12-(2,2-dimethylpropanoyl)-
  5,6,8aβ,9,10,11,12,12aβ,13,13aα-decahydro-8H-
  isoquino[2,1-g][1,6]naphthyridine hydrochloride;
2,3-dimethoxy-12-(2,2-dimethylpropanoyl)-5,6,8aα,
  9,10,11,12,12aα,13,13aα-decahydro-8H-isoquino[2,1-
  g][1,6]naphthyridine hydrochloride;
2,3-dimethoxy-12-(2,2-dimethylpropanoyl)-
  5,6,8aβ,9,10,11,12,12aβ,13,13aα-decahydro-8H-
  isoquino[2,1-g][1,6]naphthyridine hydrochloride;
3,4-methylenedioxy-12-(2,2-dimethylpropanoyl)-
  5,6,8aα,9,10,11,12,12aα,13,13aα-decahydro-8H-
  isoquino[2,1-g][1,6]naphthyridine hydrochloride;
3,4-methylenedioxy-12-(2,2,-dimethylpropanoyl)-
  5,6,8aβ,9,10,11,12,12aβ,13,13aα-decahydro-8H-
  isoquino[2,1-g][1,6]naphthyridine hydrochloride;
3-chloro-12-(2,2-dimethylpropanoyl)-
  5,6,8aα,9,10,11,12,12aα,13,13aα-decahydro-8H-
  isoquino[2,1-g][1,6]naphthyridine hydrochloride;
3-chloro-12-(2,2-dimethylpropanoyl)-
  5,6,8aβ,9,10,11,12,12aβ,13,13aα-decahydro-8H-
  isoquino[2,1-g][1,6]naphthyridine hydrochloride;
3-fluoro-12-(2,2-dimethylpropanoyl)-
  5,6,8aα,9,10,11,12,12aα,13,13aα-decahydro-8H-
  isoquino[2,1-g][1,6]naphthyridine hydrochloride; and
3-fluoro-12-(2,2-dimethylpropanoyl)-5,6,8aβ,9,10,112,-
  12aβ,13,13aα-decahydro-8H-isoquino[2,1-
  g][1,6]naphthyridine hydrochloride.
12-thiobenzoyl-5,6,8aα,9,10,11-12,12aβ,13,13aα-
  decahydro-8H-isoquino[2,1-g][1,6]naphthyridine hydrochloride;
12-thioacetyl-5,6,8aα,9,10,11,12,12aα,13,13aα-decahydro-8H-isoquino[2,1-g][1,6]naphthyridine hydrochloride;
3-methoxy-12-(2-methylthiopropanoyl)-
  5,6,8aα,9,10,11,12,12aα,13,13aα-decahydro-8H-
  isoquino[2,1-g][1,6]naphthyridine hydrochloride;
3-methoxy-12-bromothioacetyl-5,6,8aα,9,10,11,12,-
  12aα,13,13aα-decahydro-8H-isoquino[2,1g][1,6-
  ]naphthyridine hydrochloride;
3-methoxy-12-(2,2-dimethylthiopropanoyl-
  5,6,8aα,9,10,11,12,12aα,13,13aα-decahydro-8H-
  isoquino[2,1g][1,6]naphthyridine hydrochloride; and
12-(2,2-dimethylthiopropanoyl)-5,6,8aα,9,10,11,12,-
  12aα,13,13aα-decahydro-8H-isoquino[2,1g][1,6-
  ]naphthyridine hydrochloride.

EXAMPLE 6

Conversion of (±)-12 (N,N-Dimethylamino)carbonyl 5,6,8aα,9,10,11,12,12,aα,13,13aα-decahydro-8H-isquino[2,1g][1,6]naphthyridine to its hydrochloride salt Excess 3% hydrogen chloride in methanol is added to a solution of (±)-12-N,N-dimethylaminocarbonyl-5,6,8aα,9,10,11,12,12aα,13,13aα-decahydro-8H-isoquino[2,1g][1,6]naphthyridine in 20 ml methanol. Diethyl ether is added until precipitation is complete. The product is filtered, washed with ether, air dried and recrystallized from methanol/acetone to yield (±)-12-N,N-dimethylaminocarbonyl-5,6,8aα,9,10,11,12,-12aα,13,13aα-decahydro-8H-isoquino[2,1g][1,6]naphthyridine hydrochloride.

In a similar manner, all compounds of formula (1) and (2) in free base form may be converted to the acid addition salts by treatment with the appropriate acid, for example, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 7

Conversion of a salt of (±)-12-(N,N-Dimethylamino)carbonyl-5,6,8aα, 9,10,11,12,12aα,13,13aα-decahydro-8H-isoquino[2,1g][1,6]naphthyridine to the free base (±)-12-N,N-dimethylaminocarbonyl-5,6,8aα,9,10,11,12,12aα,13,13aα-decahydro-8H-isoquino[2,1g][1,6]naphthyridine hydrochloride suspended in 50 ml of ether is stirred with excess dilute aqueous potassium carbonate solution until the salt is completely dissolved. The organic layer is then separated, washed twice with water, dried over magnesium sulfate and evaporated to yield (±)-12-N,N-dimethylaminocarbonyl-5,6,8aα,9,10,11,12,12aα,13,13aα-decahydro-8H-isoquino[2,1g][1,6]naphthyridine.

In a similar manner the acid addition salts of all compounds of formula (1) and (2) may be converted to the corresponding compounds in free base form.

EXAMPLE 8

Direct interchange of acid addition salts of (±)-12-(N,N-Dimethylamino)carbonyl-5,5,6,8aα, 9,10,11,12,12,aα, 13,13aα-decahydro-8H-isoquino[2,1g][1,6]naphthyridine (±)-12-N,N-dimethylaminocarbonyl-5,6 8aα,9,10,11,12,12aα,13,13aα-decahydro-8H-isoquino[2,1g][1,6]naphthyridine acetate (1,0 g) is dissolved in 50 ml 5N aqueous hydrochloric acid, and the solution evaporated to dryness. The product is suspended in ethyl acetate and filtered, air dried and recrystallized from methanol/acetone to yield
(±)-12-N,N-dimethylaminocarbonyl 5,6,8aα,9,10,11,12,12aα,13,13aα-decahydro-8H-isoquino[2,1g][1,6]naphthyridine hydrochloride.

In a similar manner, substituting for hydrochloric acid other acids, such as sulfuric acid, nitric acid, phosphoric acid and the like, other acid addition salts of all compounds of formula (1) and (2) are prepared.

In Examples 9 through 14 the active ingredient is (±)-12-N,N-dimethylaminocarbonyl-5,6,8aα,9,10,11,12,12aα,13,13aα-decahydro-8H-isoquino[2,1g][1,6]naphthyridine hydrochloride. Other compounds of formula (1) and (2) and the pharmaceutically acceptable salts thereof may be substituted therein.

EXAMPLE 9

The composition of Oral Administration

| The composition contains: | % wt./wt. |
|---|---|
| Active ingredient | 20% |
| Lactose | 80% |

The two ingredients are milled, mixed and dispensed into capsules containing 100 mg each; one capsule would approximate a total daily dosage.

EXAMPLE 10

Composition of Oral Administration

| The composition contains: | % wt./wt. |
|---|---|
| Active ingredient | 20.0% |
| Magnesium stearate | 0.9% |
| Starch | 8.6% |
| Lactose | 79.6% |
| PVP (polyvinylpyrrolidine) | 0.9% |

The above ingredients are combined and granulated using methanol as solvent. The formulation is then dried and formed into tablets (containing 20 mg of active compound) with an appropriate tableting machine.

EXAMPLE 11

Parenteral Formulation (IV)

| The composition contains: | % wt./wt. |
|---|---|
| Active ingredient | 0.25 g |
| Propylene glycol | 20. g |
| Polyethylene glycol 400 | 20. g |
| Polysorbate 80 | 1. g |
| 0.9% Saline solution qs ad | 100 ml |

The active ingredient is dissolved in propylene glycol, polyethylene glycol 400 and polysorbate 80. A sufficient quantity of 0.9% saline solution is then added with stirring to provide 100 ml. of the I.V. solution which is filtered through a 0.2 micron membrane filter and packaged under sterile conditions.

EXAMPLE 12

Suppository Formulation

| The composition contains: | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2,5 g total weight.

EXAMPLE 13

Composition for Topical Administration to the Eye

| The composition contains: | % wt/vol |
|---|---|
| Active ingredient | 0.10 |
| Benzalkonium chloride | 0.02 |
| EDTA | 0.01 |
| Phenylethanol | 0.25 |
| Boric acid | 1.62 |

-continued

| The composition contains: | % wt/vol |
|---|---|
| water qs and | to adjust pH 100 ml |

The first four ingredients are dissolved in less than the required total volume of water, and the pH adjusted to 7.4. The volume is then brought to 100 ml with additional water.

EXAMPLE 14

Assay for pre- and post-synaptic α-adrenoceptor blockade

Protocol:

(According to Caroon, J. M. et al. *J. Med. Chem.*, 1982, Vol. 25,666.)

Contralateral, prostatic and epididymal portions of the rat isolated vas deferens were suspended in separate an baths containing oxygenated Krebs—bicarbonate solution at 37° C. The test compound was added to the Krebs—bicarbonate solution bathing the epididymal and prostatic portions of vas deferens. The contralateral portions served as control tissues. All tissues were then allowed to equilibrate with the bathing solution for minutes.

Pre-synaptic α-adrenoceptor blockade was determined using the prostatic portions of vas deferens. Following the equilibration period, dose response curves for the inhibitory effect of xylazine on the contractile response of the vas deferens to single pulse nerve stimulation were obtained.

Post-synaptic α-adrenoceptor blockade was determined using the epididymal portions of rat vas deferens. Following the equilibration period, dose-response curves for the contractile effects of phenylephrine on the vas deferens were obtained.

EXAMPLE 15

Determination of Platelet Aggregation Inhibition

Protocol:

Blood platelets are collected in the standard manner, and incubated in an Aggregation Module Incubator-Cuvette in the presence of either the inhibitor to be tested, or without said inhibitor as a control. The aggregation of the platelets is observed after the addition of an inducer, and the samples are evaluated for the presence of a lag period and the slope of the aggregation curve, as well as the maximum height of the aggregation curve in comparison to the control. $IC_{50}$ values i.e. the concentration of inhibitor required for 50% inhibition can be calculated from the inflection point on the appropriate dose response curve.

EXAMPLE 16

Determination of Effect on Intraocular Pressure

Protocol:

The compound to be tested is dissolved in saline, and applied topically to the eye. The intraocular pressure is measured immediately before application, and at specified time intervals thereafter, by means of a probe which measures the force necessary to flatten a small area of corneal surface, according to the method described by Moses, R. A., *Tr. Am. Acad. Opth. and Otol.,* Jan–Feb 1962: 88–95.

EXAMPLE 17

Determination of Effect on Rat Sexual Behavior

"Sexual Behaviour in Developing Male Rats", P. Sodersten, D. A. Dammassa and E. R. Smith, *Hormones and Behavior,* Vol. 8, pp 320–334 (1977).

Protocol:

Sexually-naive male rats, weighing 200–250 g, are housed two to a cage in a normal light cycle room (lights on 5.00 a.m., lights off 7.00 p.m.). The animals are grouped according to their weight after a 10 day acclimatization period, and tested on either the 12th or 13th day. The compound to be tested is administered 30 minutes before evaluating for sexual activity.

Stimulus female Sprague-Dawley rats, housed in a reverse light-cycle room (lights off 10.00 a.m., lights on 8.00 p.m.), are brought into sexual receptivity by injection with 20 µg of estradiol benzoate in 0.1 ml of sesame seed oil 48 hours prior to the test, and with 1 mg of progesterone in 0.1 ml of sesame seed oil 4–6 hours prior to the test.

Each male rat treated with the test compound is placed in an observation cage and allowed to acclimatize for 10 minutes. A stimulus female is then introduced into the cage and the behaviour of the male recorded on an Esterline Angus event recorder. The behaviour recorded is mounts, intromissions and ejaculations. Intromission latency (time from the start of the test to the first intromission), ejaculation latency (time from the first intromission to ejaculation), and post-ejaculatory interval (time from ejaculation to the next following intromission) are also recorded. Tests are terminated if the intromission latency is longer than 15 minutes, the ejaculation latency longer than 30 minutes, or the post-ejaculatory interval in excess of 15 minutes.

EXAMPLE 18

Weight-Loss Stimulation Assay

| SPECIES: | Charles River CD Sprague Dawley Rats. |
|---|---|
| COMPOUND: | Test compound |
| DOSE AND NUMBERS: | 50 and 100 mg/kg/day, 10 males/group. |
| DURATION OF DOSING: | Two weeks. |

EXAMPLE 19

Irritable-Bowel Syndrome Assay

Protocol:

The test used is a modification of the method of Macht and Barba-Gose (Macht, D. T. and Barba-Gose, J. (1931): J. Amer. Pharm. Ass. 20, 558), which traces the transit of a charcoal meal through the intestine as an index of transit time. In the present model, intestinal transit in conscious mice (15–20 g) is accelerated with an oral dose of barium chloride (300 mg/kg) administered at the same time as the charcoal meal. The animals are sacrificed 10 min. later and the distance travelled by the charcoal measured.

The antagonist compound is given as a 15 min. oral pretreatment and its effects on barium-stimulated intestinal transit of the charcoal meal calculated.

EXAMPLE 20

Antidepressant Assay

Protocol:

Antidepressant utility is assessed by the ability of compounds of formula (1) or (2) to down-regulate β-adrenoreceptors in rat cerebral cortex after chronic dosing; down-regulation of β-adrenoreceptors may be an index of antidepressant effectiveness (Clark, Michel and Whiting, 1986, Progress in Medicinal Chemistry, Vol. 23, 1–39). The number of β-adrenoreceptors is measured using an adaptation of the method of Bylund and Snyder (1976, Molecular Pharmacology, 12, 568) and expressed as $B_{max}$ (fmol/mg protein). Chronic dosing with the test compound reduces the number of β adrenoreceptors in rat cerebral cortex without changing the affinity of the receptors (Kd).

Male Sprague-Dawley rats are dosed with 0.5 mg/kg of the test compound o.d. p.o. for 14 days. The animals are sacrificed 24 hours after the last dose.

Tris washed cortical membranes are prepared from the rat brains and incubated with [3H]-dihydroalprenolol (0.1–4.0 nM) for 30 mins. at 25° C. The incubation is terminated by rapid filtration over Whatman GF/B filters in a Brandel Cell Harvester. Bound radioactivity is defined as the amount of ligand bound in the presence of 0.5 mM isoprenaline.

EXAMPLE 21

Hypoglycaemic Assay

The test compound is administered to groups of 10 male mice (30 mg/kg, intraperitoneally). Active compounds are found to reduce blood glucose; these hypoglycaemic effects indicate potential utility as an antidiabetic agent.

EXAMPLE 22

Antihypertensive Assay

Compounds of formula (1) and (2) have antihypertensive activity when test compounds lower blood pressure in conscious spontaneously hypertensive rats when administered intravenously. The mean blood pressure is monitored by an indwelling catheter in the tail artery.

EXAMPLE 23

Anxiolytic Assay

Protocol:

The method used is that described by Crawley and Goodwin ("Preliminary behavior model for the anxiolytic effects of benzodiazepines." Pharmac. Biochem. Behavior 1980; 13:167–170). This method involves placing naive mice in a novel test environment which comprises a box divided by a partition into a dark area and a light area. Mice are allowed to shuttle between the dark and light area for a period of 10 mins. During this time the number of shuttles, total locomotor activity and total time spent in the dark are monitored. A compound of formula (1) (0.3 mg/kg) is administered ip, and the mouse behaviour observed 30 minutes later. The prescribed test parameters (number of shuttles, time spent in the dark area, and total locomotor activity) are compared to control data using a standard Student's t-test and the percent of control response calculated.

What is claimed is:

1. A compound of the formula (1) or (2):

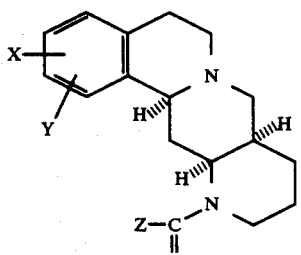

(1)

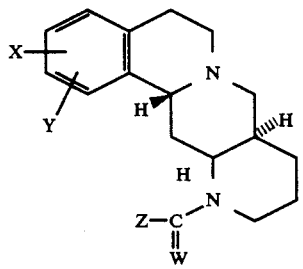

(2)

in which:

X and Y are independently hydrogen, hydroxy, lower alkyl of one to six carbon atoms, lower alkoxy of one to six carbon atoms or halo, or X and Y when adjacent and taken together is methylenedioxy or ethylene-1,2 dioxy;

W is oxygen or sulfur; and

Z is —R$^1$, —OR$^2$ or —NR$^3$R$^4$, wherein

R$^1$ is lower alkyl of one to six carbon atoms, lower haloalkyl of the formula V(CH$_2$)$_n$— in which V is bromo, chloro or fluoro and n is an integer of 1–6, cycloalkyl of 3–8 carbon atoms, heteroaryl, phenyl or phenyl lower alkyl in which any phenyl group may be optionally substituted by one or two substituents chosen from halo, lower alkyl of one to four carbon atoms and lower alkoxy of one to four carbon atoms;

R$^2$ is lower alkyl of one to six carbon atoms, phenyl or phenyl lower alkyl in which any phenyl group may be optionally substituted by one or two substituents chosen from halo, lower alkyl of one to four carbon atoms and lower alkoxy of one to four carbon atoms;

R$^3$ and R$^4$ are independently hydrogen, alkyl of one to eight carbon atoms, phenyl or phenyl lower alkyl in which any phenyl group may be optionally substituted by one or two substituents chosen from halo, lower alkyl of one to four carbon atoms and lower alkoxy of one to four carbon atoms; or R$^3$ and R$^4$ taken together with the nitrogen to which they are attached represent a heterocycle of the formula:

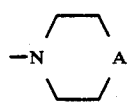

wherein A is —(CH$_2$)$_m$, —N(R$^5$)— or oxygen, in which m is an integer of 0–2 and R$^5$ is hydrogen or lower alkyl;

with the proviso that for the compound of formula (2) where X is 2-methoxy, Y is 3-methoxy and W is oxygen Z cannot be methyl;
or a pharmaceutically acceptable salt thereof.

2. The compound of claim 1 which is a compound of formula (1), or a pharmaceutically acceptable salt thereof.

3. The compound of claim 2 in which X and Y are independently hydrogen or lower alkoxy having one to four carbon atoms, or X and Y taken together is methylenedioxy, or a pharmaceutically acceptable salt thereof.

4. The compound of claim 3 in which W is oxygen and Z is —R$^1$, or a pharmaceutically acceptable salt thereof.

5. The compound of claim 4 in which —R$^1$ is lower alkyl or V(CH$_2$)$_n$—, or a pharmaceutically acceptable salt thereof.

6. The racemic compound of claim 5 in which R$^1$ is bromomethyl, X is 3-methoxy and Y is hydrogen, namely (±)-3-methoxy-12-bromoacetyl-5,6,8aα,9,10,11,12,12aα,13,13aα-decahydro-8H-isoquino[2,1g][1,6]naphthyridine, or a pharmaceutically acceptable salt thereof.

7. A single enantiomer of the compound of claim 6, namely (8aR,12aS,13aS)-3-methoxy-12-bromoacetyl-5,6,8a,9,10,11,12,12a,13,13a-decahydro-8H-isoquino[2,1-g][1,6]naphthyridine, or a pharmaceutically acceptable salt thereof.

8. The racemic compound of claim 5 in which R$^1$ is t-butyl, X is 3-methoxy and Y is hydrogen, namely (±)-3-methoxy-12-(2,2-dimethylpropanoyl)-5,6,8aα,9,10,11,12,12aα,13,13aα-decahydro-8H-isoquino[2,1g][1,6]naphthyridine, or a pharmaceutically acceptable salt thereof.

9. A single enantiomer of the compound of claim 8, namely (8aR,12aS,13aS)-3-methoxy-12-(2,2-dimethylpropanoyl-5,6,8a,9,10,11,12,12a,13,13a-decahydro-8H-isoquino[2,1-g][1,6]naphthyridine, or a pharmaceutically acceptable salt thereof.

10. The compound of claim 3 in which W is oxygen and Z is —OR$^2$, or a pharmaceutically acceptable salt thereof.

11. The compound of claim 10 in which R$^2$ is benzyl, or a pharmaceutically acceptable salt thereof.

12. The racemic compound of claim 11 in which X and Y are both hydrogen, namely (±)-12-benzyloxycarbonyl-5,6,8aα,9,10,11,12,12aα,13,13aα-decahydro-8H-isoquino[2,1g][1,6]naphthyridine, or a pharmaceutically acceptable salt thereof.

13. A single enantiomer of the compound of claim 12, namely (8aR,12aS,13aS)-12-benzyloxycarbonyl-5,6,8a,9,10,11,12,12a,13,13a-decahydro-8H-isoquino[2,1-g][1,6]naphthyridine, or a pharmaceutically acceptable salt thereof.

14. The compound of claim 3 in which W is oxygen and Z is —NR$^3$R$^4$, or a pharmaceutically acceptable salt thereof.

15. The compound of claim 14 in which R$^3$ and R$^4$ are independently hydrogen or lower alkyl, or a pharmaceutically acceptable salt thereof.

16. The compound of claim 15 in which R$^3$ and R$^4$ are both methyl, or a pharmaceutically acceptable salt thereof.

17. The compound of claim 16 in which X and Y are both hydrogen, namely (±)-12-N,N-dimethylaminocarbonyl-5,6,8aα,9,10,11,12,12-aα,13,13aα-decahydro-8H-isoquino[2,1-g][1,6]naphthyridine, or a pharmaceutically acceptable salt thereof.

18. A single enantiomer of the compound of claim 17, namely (8aR,12aS,13aS)-12-N,N-dimethylaminocarbonyl-5,6,8a,9,10,11,12,12a,13,13a-decahydro-8H-isoquino[2,1-g][1,6]naphthyridine, or a pharmaceutically acceptable salt thereof.

19. The compound of claim 16 in which X is 3-methoxy and Y is hydrogen, namely (±)-3-methoxy-12-N,N-dimethylaminocarbonyl-5,6,8aα,9,10,11,12,-12aα,13,13aα-decahydro-8H-isoquino[2,1-g][1,6]naphthyridine, or a pharmaceutically acceptable salt thereof.

20. A single enantiomer of the compound of claim 19, namely (8aR,12aS,13aS) 3-methoxy-12-N,N-dimethylaminocarbonyl 5,6,8a,9,10,11,12,12a,13,13a-decahydro-8H-isoquino[2,1-g][1,6]naphthyridine, or a pharmaceutically acceptable salt thereof.

21. The compound of claim 16 in which X and Y taken together is 2,3-methylenedioxy, namely (±)-2,3-methylenedioxy-12-N,N-dimethylaminocarbonyl-5,6,8aα,9,10,11,12,12aα,13,13aα-decahydro-8H-isoquino[2,1-g][1,6]naphthyridine, or a pharmaceutically acceptable salt thereof.

22. A single enantiomer of the compound of claim 21, namely (8aR,12aS,13aS)-2,3-methylenedioxy-12-N,N-dimethylaminocarbonyl-5,6,8a,9,10,11,12,12a,13,13a-decahydro-8H-isoquino[2,1-g][1,6]naphthyridine, or a pharmaceutically acceptable salt thereof.

23. The compound of claim 14 in which $R^3$ is phenyl, benzyl or (R) (+)-1-phenylethyl and $R^4$ is hydrogen, or a pharmaceutically acceptable salt thereof.

24. The compound of claim 23 in which $R^3$ is phenyl, X is 3-methoxy and Y is hydrogen, namely (±3-methoxy-12-phenylaminocarbonyl-5,6,8aα,9,10,11,12,-12aα,13,13aα-decahydro-8H-isoquino[2,1-g][1,6]-naphthyridine, or a pharmaceutically acceptable salt thereof.

25. A single enantiomer of the compound of claim 24, namely (8aR,12aS,13aS)-3-methoxy-12-phenylaminocarbonyl-5,6,8a,9,10,11,12,12a,13,13a-decahydro 8H-isoquino[2,1-g][1,6]naphthyridine, or a pharmaceutically acceptable salt thereof.

26. The compound of claim 23 in which $R^3$ is benzyl and X and Y are both hydrogen, namely (±)-12-benzylaminocarbonyl-5,6,8aα,9,10,11,12,12aα,13,13aα-decahydro-8H-isoquino[2,1-g][1,6]naphthyridine, or a pharmaceutically acceptable salt thereof.

27. A single enantiomer of the compound of claim 24, namely (8aR, 12aS,13aS)-12-benzylaminocarbonyl-5,6,8a,9,10,11,12,12a,13,13a-decahydro-8H-isoquino[2,1-g][1,6]naphthyridine, or a pharmaceutically acceptable salt thereof.

28. The compound of claim 23 in which $R^3$ is (R)-(+)-1-phenylethyl and X and Y are both hydrogen, namely (±)-12-[(R)-(+)-1-phenylethylamino]carbonyl-5,6,8aα,9,10,11,12,12aα,13,13aα-decahydro-8H-isoquino[2,1-g][1,6]naphthyridine, or a pharmaceutically acceptable salt thereof.

29. A single enantiomer of the compound of claim 28, namely (8aR,12aS,13aS)-12-[(R)-(+)-1-phenylethylamino]carbonyl 5,6,8a,9,10,11,12,12a,13,13a-decahydro-8H-isoquino[2,1-g][1,6]naphthyridine, or a pharmaceutically acceptable salt thereof.

30. The compound of claim 3 in which W is sulfur and Z is —$NR^3R^4$, or a pharmaceutically acceptable salt thereof.

31. The compound of claim 30 in which $R^3$ and $R^4$ are both methyl and X and Y are both hydrogen, namely (±)-12-N,N-dimethylaminothiocarbonyl 5,6,8aα,9,10,11,12,12aα,13,13aα-decahydro 8H-isoquino[2,1-g][1,6]naphthyridine, or a pharmaceutically acceptable salt thereof.

32. A single enantiomer of the compound of claim 31, namely (8aR,12aS,13aS)-12-N,N-dimethylaminothiocarbonyl-5,6,8a,9,10,11,12,12a,13,13a-decahydro-8H-isoquino[2,1-g][1,6]naphthyridine, or a pharmaceutically acceptable salt thereof.

33. The compound of claim 1 which is a compound of formula (2), or a pharmaceutically acceptable salt thereof.

34. The compound of claim 33 in which X and Y are independently hydrogen or lower alkoxy having one to four carbon atoms or X and Y taken together is methylenedioxy, or a pharmaceutically acceptable salt thereof.

35. The compound of claim 34 in which W is oxygen and Z is —$NR^3R^4$, in which $R^3$ and $R^4$ are lower alkyl having one to four carbon atoms, phenyl or benzyl, or a pharmaceutically acceptable salt thereof.

36. A composition suitable for administration to a mammal having a disease state which is alleviated by treatment with an $\alpha_2$-blocker, which composition comprises a therapeutically effective amount of a compound of the formula

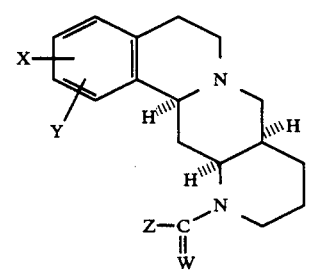

(1)

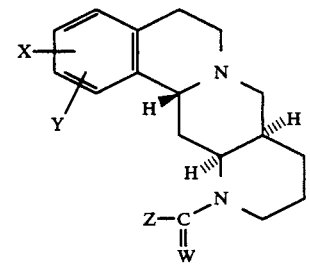

(2)

in which:
X and Y are independently hydrogen, hydroxy, lower alkyl of one to six carbon atoms, lower alkoxy of one to six carbon atoms or halo, or X and Y when adjacent and taken together is methylenedioxy or ethylene-1,2-dioxy;

W is oxygen or sulfur; and

Z is —$R^1$, —$OR^2$ or —$NR^3R^4$, wherein $R^1$ is lower alkyl of one to six carbon atoms, lower haloalkyl of the formula V(CH$_2$)$_n$— in which V is bromo, chloro or fluoro and n is an integer of 1-6, cycloalkyl of 3-8 carbon atoms, heteroaryl, phenyl or phenyl lower alkyl in which any phenyl group may be optionally substituted by one or two substituents chosen from halo, lower alkyl of one to four carbon atoms and lower alkoxy of one to four carbon atoms;

$R^2$ is lower alkyl of one to six carbon atoms, phenyl or phenyl lower alkyl in which any phenyl group may be optionally substituted by one or two substituents chosen from halo, lower alkyl of one to four carbon atoms and lower alkoxy of one to four carbon atoms;

R³ and R⁴ are independently hydrogen, alkyl of one to eight carbon atoms, phenyl or phenyl lower alkyl in which any phenyl group may be optionally substituted by one or two substituents chosen from halo, lower alkyl of one to four carbon atoms and lower alkoxy of one to four carbon atoms; or R³ and R⁴ taken together with the nitrogen to which they are attached represent a heterocycle of the formula:

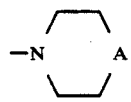

wherein A is —$(CH_2)_m$, —$N(R^5)$— or oxygen, in which m is an integer of 0–2 and R⁵ is hydrogen or lower alkyl, or a pharmaceutically acceptable salt thereof, in admixture with one or more pharmaceutically acceptable non-toxic carriers.

37. A method for treating a mammal having a disease-state which is alleviated by treatment with an $\alpha_2$-blocker, which comprises administering a therapeutically effective amount of a compound of the formula

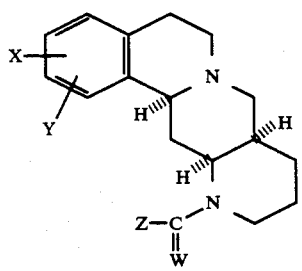 (1)

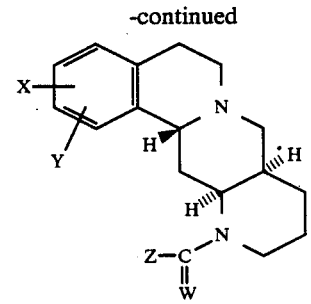 (2)

in which:
X and Y are independently hydrogen, hydroxy, lower alkyl of one to six carbon atoms, lower alkoxy of one to six carbon atoms or halo, or X and Y when adjacent and taken together is methylenedioxy or ethylene-1,2-dioxy;
W is oxygen or sulfur; and
Z is —R¹, —OR² or NR³R⁴, wherein
R¹ is lower alkyl of one to six carbon atoms, lower haloalkyl of the formula $V(CH_2)_n$— in which V is bromo, chloro or fluoro and n is an integer of 1–6, cycloalkyl of 3–8 carbon atoms, heteroaryl, phenyl or phenyl lower alkyl in which any phenyl group may be optionally substituted by one or two substituents chosen from halo, lower alkyl of one to four carbon atoms and lower alkoxy of one to four carbon atoms;
R² is lower alkyl of one to six carbon atoms, phenyl or phenyl lower alkyl in which any phenyl group may be optionally substituted by one or two substituents chosen from halo, lower alkyl of one to four Carbon atoms and lower alkoxy of one to four carbon atoms;
R³ and R⁴ are independently hydrogen, alkyl of one to eight carbon atoms, phenyl or phenyl lower alkyl in which any phenyl group may be optionally substituted by one or two substituents chosen from halo, lower alkyl of one to four carbon atoms and lower alkoxy of one to four carbon atoms; or
R³ and R⁴ taken together with the nitrogen to which they are attached represent a heterocycle of the formula:

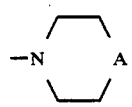

wherein A is —$(CH_2)_m$, —$N(R^5)$— or oxygen, in which m is an integer of 0–2 and R⁵ is hydrogen or lower alkyl, or a pharmaceutically acceptable salt thereof.

38. The method of claim 37, wherein said disease-state is depression, anxiety, excessive platelet aggregation, diabetes, male impotence, elevated intraocular pressure or irritable-bowel syndrome.

* * * * *